United States Patent [19]

Moore et al.

[11] Patent Number: 5,962,256
[45] Date of Patent: Oct. 5, 1999

[54] NUCLEAR THYROID HORMONE RECEPTOR-INTERACTING POLYNUCLEOTIDES AND RELATED MOLECULES AND METHODS

[75] Inventors: David D. Moore, Hingham; Jae Woon Lee, Somerville, both of Mass.

[73] Assignee: The General Hospital Corporation, Boston, Mass.

[21] Appl. No.: 08/471,613

[22] Filed: Jun. 6, 1995

Related U.S. Application Data

[60] Division of application No. 08/222,719, Apr. 4, 1994, which is a continuation-in-part of application No. 07/969,136, Oct. 30, 1992, abandoned.

[51] Int. Cl.$^6$ ............................. C12N 15/10; C12N 5/10; C12N 1/21; C12N 1/15
[52] U.S. Cl. ..................... 435/69.1; 435/325; 435/252.3; 435/254.11; 435/320.1; 536/23.5
[58] Field of Search ................................ 435/69.1, 240.2, 435/252.3, 254.11, 320.1; 530/399, 350; 536/23.51, 23.5

[56] References Cited

U.S. PATENT DOCUMENTS

| | | | |
|---|---|---|---|
| 4,833,080 | 5/1989 | Brent et al. | 435/172.3 |
| 5,240,832 | 8/1993 | Kelton et al. | 435/69.4 |
| 5,272,071 | 12/1993 | Chappel | 435/172.3 |
| 5,283,173 | 2/1994 | Fields et al. | 435/6 |

FOREIGN PATENT DOCUMENTS

| | | |
|---|---|---|
| WO 92/07072 | 4/1992 | WIPO . |
| WO 93/11235 | 6/1993 | WIPO . |
| WO 93/13129 | 7/1993 | WIPO . |

OTHER PUBLICATIONS

Meyerson et al., The EMBO Journal 11:2909–2917 (1992).
Yang et al., Science 257:680–682 (1992).
Koff et al., Cell 66:1217–1228 (1991).
Tsai et al., Nature 353:174–177 (1991).
Xiong et al., Cell 65:691–699 (1991).
Draetta, Trends in Biochem. Sci. 15:378–382 (1990).
Richardson et al., Genes & Development 4:1332–1344 (1990).
Wittenberg et al., Cell 62:225–237 (1990).
Richardson et al., Cell 59:1127–1133 (1989).
Wittenberg et al., Molecular and Cellular Biology 9:4064–4068 (1989).
Pines et al., Cell 59:833–846 (1989).
Hadwiger et al., Proc. Natl. Acad. Sci. USA 86:6255–6259 (1989).
Wittenberg et al., Cell 54:1061–1072 (1988).
Gill et al., Nature 334:721–724 (1988).
Brent et al., Nature 312:612–615 (1984).
Brent et al., 43:729–736 (1985).
Dalton and Treisman, Cell 68:597–612 (1992).
Touchette, The Journal of NIH Research 3:44–46 (1991).
Chien et al., Proc. Natl. Acad. Sci. USA 88:9578–9582 (1991).
Fields and Song, Nature 340:245–246 (1989).
PCT International Search Report, Int'l Appln No. PCT/US93/10069, mailed Jan. 26 (1994).
Fearon et al., PNAS USA 89:7958–7962 (1992).
Broach et al., Gene 8 (121–133 (1979).
Celenza et al., Science 233 (1175–1180 (1986).
Celenza et al., Molecular and Cellular Biology 9, 5045–5054 (1989).
Celenza et al., Molecular and Cellular Biology 9, 5034–5044 (1989).
Curran et al., Cell 55, 395–397 (1988).
Dang et al., Molecular and Cellular Biology 11, 954–962 (1991).
Furey et al., Science 231, 704–707 (1986).
Gill et al., Cell 51:121–126 (1987).
Goff et al., Genes & Development 6, 864–875 (1992).
Hardy et al., Genes & Development 6, 801–814 (1992).
Hope et al., Cell 46, 885–894 (1986).
Hope et al., Nature 333:635–640 (1988).
Hu et al., Science 250:1400–1403 (1990).
Johnston, Microbiological Reviews 51, 458–476 (1987).
Keegan et al., Science 231, 699–704 (1986).
Kumar et al., Cell 51:941–951 (1987).
Laughon et al., Molecular and Cellular Biology 4:260–267 (1984).
Ma et al., Cell 55:443–446 (1988).
Ma et al., Cell 48:847–853 (1987).
Martin et al., Molecular and Cellular Biology 10:1908–1914 (1990).
McKnight et al., Proc. Natl. Acad. Sci. USA 84:7061–7065 (1987).
Silver et al., Proc. Natl. Acad. Sci. USA 81:5951–5955 (1984).
Thukral et al., Molecular and Cellular Biology, 9:2360–2369 (1988).

(List continued on next page.)

*Primary Examiner*—Stephen Walsh
*Assistant Examiner*—Claire M. Kaufman
*Attorney, Agent, or Firm*—Clark & Elbing LLP

[57] ABSTRACT

Disclosed is a method for determining whether a test protein is capable of interacting with a nuclear hormone receptor protein. The method involves: (a) providing a host cell which contains (i) a reporter gene operably linked to a protein binding site; (ii) a first fusion gene which expresses a first fusion protein, the first fusion protein including a nuclear hormone receptor protein covalently bonded to a binding moiety which is capable of specifically binding to the protein binding site; and (iii) a second fusion gene which expresses a second fusion protein, the second fusion protein including the test protein covalently bonded to a weak gene activating moiety; and (b) determining whether the test protein increases expression of the reporter gene as an indication of its ability to interact with the nuclear hormone receptor protein. Such an interaction may be hormone dependent, hormone independnet, or hormone sensitive. Also disclosed is purified DNA encoding thyroid hormone receptor-interacting proteins and the polypeptides expressed from such DNA.

7 Claims, 37 Drawing Sheets

OTHER PUBLICATIONS

Wittekind et al., Molecular and Cellular Biology 8:3997–4008 (1988).

Schaufele et al., Mol. Endocrin. 6:656–665 (1992).

Ma et al., Cell 48:847–853 (1987).

Burnside et al., J. Biol. Chem. 265(5):2500–2504 (1990).

Godowski et al., Science 241:812–816 (1988).

Ma et al., Cell 51:113–119 (1987).

Beg et al., Genes & Dev. 7:2064–2070 (1993).

Ohno et al., Cell 60:991–997 (1990).

Zhang et al., "Retinoid X receptor is an auxiliary protein for thyroid hormone and retinoic acid receptors", Nature 355:441–446 (1992).

Bugge et al., "RXRα, a promiscuous partner of retinoic acid and thyroid hormone receptors", EMBO J. 11:1409–1418 (1992).

Akamizu et al., "A Microsequencing Approach to Identify Proteins which Appear to Interact with Thyrotropin in Rat FRTL–5 Thyroid Cells," Biochem. and Biophys. Res. Communications 170:351–358, 1990.

Michikawa et al., "Antigenic Protein Specific for C3H Strain Mouse is a Mitochondrial Stress–70 Protein," EMBL Sequence Database, Accession No. D17556, 1993.

Lee et al., "Two Classes or Proteins on Either the Presence or Absence of Thyroid Hormone for the Interaction with the Thyroid Hormone Receptor," Endocrinology 9:243–254, 1995.

Lee et al., "Interaction of Thyroid–Hormone Receptor with a Conserved Transcriptional Mediator," Nature:374:91–94, 1995.

Swaffield et al. (1992) Alterations in a Yeast Protein Resembling HIV Tat–binding Protein Relieve Requirement for an Acidic Activation Domains in GAL4, Nature 357:698–700.

Hallenbeck et al. (1992) Proc. Nat. Acad. Sci. 89:5572–5576.

```
JL1                                          .MALDGPEQMELEEGKAG
                                             |   . .:  ||
SUG1                                         MTAAVTSSNIVLE..THE

18  SGLRQYYLSKIEELQLIVNDKSQNLRRLQAQRNELNAKVRLLREELQLLQ
         ||::  |: .||:|  :|  :..|.:|  |||:||||  ||  |||::::||.|||
     17  SGIKPYFEQKIQETELKIRSKTENGRRLEAQRNALNDKVRFIKDELRLLQ

68  EQGSYVGEVVRAMDKKKVLVKVHPEGKFVVDVDKNIDINDVTPNCRVALR
         |  |||||||::  ...||||||||.||||::|||  |:|::.|:  ..  ||.||
     67  EPGSYVGEVIKIVSDKKVLVKVQPEGKYIVDVAKDINVKDLKASQRVCLR

118  NDSYTLHKILPNKVDPLVSLMMVEKVPDSTYEMIGGLDKQIKEIKEVIEL
         .|||  |||:|  ||  ||||||:|||||||||||:|:|||  ||||||||||||
    117  SDSYMLHKVLENKADPLVSIMMVEKVPDSTYDMVGGLTKQIKEIKEVIEL

168  PVKHPELFEALGIAQPKGVLLYGPPGTGKTLLARAVAHHTDCTFIRVSGS
         ||||||||.|||||||:||||||||||||||||||||||||||  ||||||.
    167  PVKHPELFESLGIAQPKGVILYGPPGTGKTLLARAVAHHTDCKFIRVSGA

218  ELVQKFIGEGARMVRELFVMAREHAPSIIFMDEIDSIGSSRLEGGSGGSS
         |||||:||||.|||||||||||||||||||||||||||||.|:||..||.|
    217  ELVQKYIGEGSRMVRELFVMAREHAPSIIFMDEIDSIGSTRVEGSGGGDS

268  EVQRQMLELLNQLDGFEATKNIKVIMATNRIDMLDSALLRPGRIDRKIEF
         ||||  |||||||||||..||||:||||||:|:||.||||||||||||||
    267  EVQRTMLELLNQLDGFETSKNIKIIMATNRLDILDPALLRPGRIDRKIEF

318  PPPNEEARLDILKIHSRKMNLTRGINLRKIAELMPGASGAEVKGVCTEAG
         |||.  ||  :||:|||||||||||||||||:||  |  |.|||:||||||||
    317  PPPSVAARAEILRIHSRKMNLTRGINLRKVAEKMNGCSGADVKGVCTEAG

368  MYALRERRVHVTQEDFEMAVAKVMQKDSEKNMSIKKLWK  406
         ||||||||:|||||||:||.|||.|:.|    :|:  ||:|
    367  MYALRERRIHVTQEDFELAVGKVMNKNQETAISVAKLFK  405
```

Fig. 2

1    MPGPLRGQHF YAVERRAYCE GCYVATLEKC ATCSOPILDR ILRAMGKAYH

51   PGCFTCVVCH RGLDGIPFTV DATSOIHCIE DFHRKFAPRC SVCGGAIMPE

101  PGOEETVRIV ALDRSFHIGC YKCEECGLLL SSEGECOGCY PLDGHILCKA

151  CRPGASRSSQ PPSGLTAESS MKYLLGSQFQ FPSFD*

Fig. 3A

```
JL2    30    CATCSQPILDR.ILRAMGKAYHPGCFTCVVCHRGLDGIPFTVDATSQI  76
              ||.|.||||||  ::  :||.:| .|: |  |.  :.    .|  .|
Lin11  45    CAACAQPILDRYVFTVLGKCWHQSCLRCCDCRAPMSMTCFSRD..GLI  90

77    HCIEDFHRKFAPRCSVCGGAIMPEPGQEETVRIVALDRSFHIGCYKCEEC 126
              |  || |::. ||. | |  :    .|: ||  | |: ||| |:.|. |
       91    LCKTDFSRRYSQRCAGCDGKL....EKEDLVR.RARDKVFHIRCFQCSVC 135

127    GLLLSSEGECQGCYPLDGH.ILCKAC
              ||..  :    | ::|. .:|..
      136    QRLLDTGDQ...LYIMEGNRFVCQSD
```

Fig. 3B

```
    AACCCAATTCTTACCAGTTTGTTGCAAATCACAGGGAACNGGGGGTCTACCATTGGCTCG
  1 ------------+---------+---------+---------+---------+---------+ 60
    TTGGGTTAAGAATGGTCAAACAACGTTTAGTGTCCCTTGNCCCCCAGATGGTAACCGAGC a   N  P  I  L  T  S  L  L  Q  I  T  G  N  ?  G  S  T  I  G  S  -

AGTCCGACCCCTCCTCATCACACGCCGCCACCTGTCTCTTCGATGGCCGGCAACACCAAG
 61 ------------+---------+---------+---------+---------+---------+ 120
    TCAGGCTGGGGAGGAGTAGTGTGCGGCGGTGGACAGAGAAGCTACCGGCCGTTGTGGTTC a   S  P  T  P  P  H  H  T  P  P  P  V  S  S  M  A  G  N  T  K  -

AACCACCCGATGCTCATGAACCTTCTTAAAGATAATCCTGCCCAGGATTTCTCAACCCTT
121 ------------+---------+---------+---------+---------+---------+ 180
    TTGGTGGGCTACGAGTACTTGGAAGAATTTCTATTAGGACGGGTCCTAAAGAGTTGGGAA a   N  H  P  M  L  M  N  L  L  K  D  N  P  A  Q  D  F  S  T  L  -

TATGGAAGCAGCCCTTTAGAAAGGCAGAACTCCTCTTTCGGCTCACCCCGCATGGAAATA
181 ------------+---------+---------+---------+---------+---------+ 240
    ATACCTTCGTCGGGAAATCTTTCCGTCTTGAGGAGAAAGCCGAGTGGGGCGTACCTTTAT a   Y  G  S  S  P  L  E  R  Q  N  S  S  F  G  S  P  R  M  E  I  -

TGCTCGGGGAGCAACAAGACCAAGAAAAAGAAGTCATCAAGATTACCACCTGAGAAACCA
241 ------------+---------+---------+---------+---------+---------+ 300
    ACGAGCCCCTCGTTGTTCTGGTTCTTTTTCTTCAGTAGTTCTAATGGTGGACTCTTTGGT a   C  S  G  S  N  K  T  K  K  K  K  S  S  R  L  P  P  E  K  P  -

AAACAACGCGAGGATATAATTGCCAAAACCAGGCTTGAGGTTGGTGACTCTTGAAAGATT
301 ------------+---------+---------+---------+---------+---------+ 360
    TTTGTTGCGCTCCTATATTAACGGTTTTGGTCCGAACTCCAACCACTGAGAACTTTCTAA a   K  Q  R  E  D  I  I  A  K  T  R  L  E  V  G  D  S  *  K  I  -

TTCTTTCTTCAGGCCTAGATCAGAAAATTAAGTGCAGCAATATCATGAATTCTCAGAAGC
361 ------------+---------+---------+---------+---------+---------+ 420
    AAGAAAGAAGTCCGGATCTAGTCTTTTAATTCACGTCGTTATAGTACTTAAGAGTCTTCG a   F  F  L  Q  A  *  I  R  K  L  S  A  A  I  S  *  I  L  R  S  -

CCTTTCAGGGAGCCAGTGAGTCATACAGTATCCACAGTTGAGTCACTTAAAGATGTCAGT
421 ------------+---------+---------+---------+---------+---------+ 480
    GGAAAGTCCCTCGGTCACTCAGTATGTCATAGGTGTCAACTCAGTGAATTTCTACAGTCA a   P  F  R  E  P  V  S  H  T  V  S  T  V  E  S  L  K  D  V  S  -

ATACGAAACATTATT
481 ---------+----- 495
    TATGCTTTGTAATAA a   I  R  N  I  I  -
```

Fig. 4

(SEQ ID NO: 6)

```
        CTCAAATGTAGCACCGTCGTCTGCGTGATCTGCTTGGAGAAGCCCAAATACCGCTGTCCA
      1 ---------+---------+---------+---------+---------+---------+ 60
        GAGTTTACATCGTGGCAGCAGACGCACTAGACGAACCTCTTCGGGTTTATGGCGACAGGT a       L  K  C  S  T  V  V  C  V  I  C  L  E  K  P  K  Y  R  C  P  -

GCCTGCCGCGTGCCCTACTGCTCGGTAGTCTGCTTCCGGAAGCACAAAGAACAGTGCAAC
     61 ---------+---------+---------+---------+---------+---------+ 120
        CGGACGGCGCACGGGATGACGAGCCATCAGACGAAGGCCTTCGTGTTTCTTGTCACGTTG a       A  C  R  V  P  Y  C  S  V  V  C  F  R  K  R  K  H  E  Q  C  N -

CCTGAAACTCGTCCTGTTGAGAAAAAAATAAGATCAGCTCTTCCTACCAAAACCGTAAAG
    121 ---------+---------+---------+---------+---------+---------+ 180
        GGACTTTGAGCAGGACAACTCTTTTTTTATTCTAGTCGAGAAGGATGGTTTTGGCATTTC a       P  E  T  R  P  V  E  K  K  I  R  S  A  L  P  T  K  T  V  K  -

CCTGTGGAAAACAAAGATGATGATGACTCTATAGCTGATTTTCTCAATAGTGATGAGGAA
    181 ---------+---------+---------+---------+---------+---------+ 240
        GGACACCTTTTGTTTCTACTACTACTGAGATATCGACTAAAAGAGTTATCACTACTCCTT a       P  V  E  N  K  D  D  D  D  S  I  A  D  F  L  N  S  D  E  E  -

GAAGACAGAGTTTCTTTGcagaatttaaagaatttaggggaaTctgcaacattaagaagc
    241 ---------+---------+---------+---------+---------+---------+ 300
        CTTCTGTCTCAAAGAAACgtcttaaatttcttaaatccccttAgacgttgtaattcttcg a       E  D  R  V  S  L  Q  N  L  K  N  L  G  E  S  A  T  L  R  S  - ttattgctcaatccacacctcaggcagttgatggtcaacctcgatcagggagaagacaaa
    301 ---------+---------+---------+---------+---------+---------+ 360
        aataacgagttaggtgtggagtccgtcaactaccagttggagctagtccctcttctgttt a       L  L  L  N  P  H  L  R  Q  L  M  V  N  L  D  Q  G  E  D  K  - gcaaagctcatgagagcttacatgcaagagcctttGtttgtggagtttgcaGactgctgt
    361 ---------+---------+---------+---------+---------+---------+ 420
        cgtttcgagtactctcgaatgtacgttctcggaaaCaaacacctcaaacgtCtgacgaca a       A  K  L  M  R  A  Y  M  Q  E  P  L  F  V  E  F  A  D  C  C  - ttaggaattgtggagccatcccagaatgaggagtcttaagatggattattgtgctgcttg
    421 ---------+---------+---------+---------+---------+---------+ 480
        aatccttaacacctcggtagggtcttactcctcagaattctacctaataacacgacgaac a       L  G  I  V  E  P  S  Q  N  E  E  S  *  D  G  L  L  C  C  L  - ctcaagcgtgtgcttgactcctggaacctgcctGCTCCCTCTCCCAGACCAGCTAGTTTG
    481 ---------+---------+---------+---------+---------+---------+ 540
        gagttcgcacacgaactgaggaccttggacggaCGAGGGAGAGGGTCTGGTCGATCAAAC a       L  K  R  V  L  D  S  W  N  L  P  A  P  S  P  R  P  A  S  L  -

GGGCTGGGGAGCTCAGGCAAAAGAGGTTTCCAGGATGCAGATTAGGTCATGCAGGCCTTT
    541 ---------+---------+---------+---------+---------+---------+ 600
        CCCGACCCCTCGAGTCCGTTTTCTCCAAAGGTCCTACGTCTAATCCAGTACGTCCGGAAA
```

Fig. 5A

```
a     G  L  G  S  S  G  K  R  G  F  Q  D  A  D  *  V  M  Q  A  F    -
      ACCGGCATTGATGTGGCTCATGTTTCAGGCAGACTTGGGGTCCTTAAGGTGGCAAGTCCT
601   ---------+---------+---------+---------+---------+---------+  660
      TGGCCGTAACTACACCGAGTACAAAGTCCGTCTGAACCCCAGGAATTCCACCGTTCAGGA
a     T  G  I  D  V  A  H  V  S  G  R  L  G  V  L  A  V  A  S  P    -
      TTATGGAGAGAAAACTTGACATTCAGATGATTGTTTTTAAATGTTTTACTTTTGGTACAG
661   ---------+---------+---------+---------+---------+---------+  720
      AATACCTCTCTTTTGAACTGTAAGTCTACTAACAAAAATTTACAAAATGAAAACCATGTC
a     L  W  R  E  N  L  T  F  R  *  L  F  L  N  V  L  L  L  V  Q    -
      TTGATAGACATCATAAACGATATCAAGCTTACACTTCATATGGAGTTAAACTTGGTCAGT
721   ---------+---------+---------+---------+---------+---------+  780
      AACTATCTGTAGTATTTGCTATAGTTCGAATGTGAAGTATACCTCAATTTGAACCAGTCA
a     L  I  D  I  I  N  D  I  K  L  T  L  H  M  E  L  N  L  V  S    -
      GTTAATAAAATCAAAACGTGATTCTACTGTACATTGCATTATTCATAATTTAATTGTTTG
781   ---------+---------+---------+---------+---------+---------+  840
      CAATTATTTTAGTTTTGCACTAAGATGACATGTAACGTAATAAGTATTAAATTAACAAAC
a     V  N  K  I  K  T  *  F  Y  C  T  L  M  Y  S  *  F  N  C  L    -
      AAATTACATTAAATAAATCAACTAATTAAAAAAAAAAAAAAAAAA
841   ---------+---------+---------+---------+-----  885
      TTTAATGTAATTTATTTAGTTGATTAATTTTTTTTTTTTTTTTTTT
a     K  L  H  *  I  N  Q  L  I  K  K  K  K  K  K    -
```

Fig. 5B (SEQ ID NO: 7)

```
    TCGCTCGTGCTCGCCCGCGCCTGGCCTACCGCGGCACTCCCGGCTGCACGCTCTGCTTGG
  1 ---------+---------+---------+---------+---------+---------+ 60
    AGCGAGCACGAGCGGGCGCGGACCGGATGGCGCCGTGAGGGCCGACGTGCGAGACGAACC a   S  L  V  L  A  R  A  W  P  T  A  A  L  P  A  A  R  S  A  W   -

CCTCGCATGCCGGTGGACCTCAGCAAGTGGTCCGGGCCCTTGAGCCTGCAAGAAGTGGAC
 61 ---------+---------+---------+---------+---------+---------+ 120
    GGAGCGTACGGCCACCTGGAGTCGTTCACCAGGCCCGGGAACTCGGACGTTCTTCACCTG a   P  R  M  P  V  D  L  S  K  W  S  G  P  L  S  L  Q  E  V  D   -

GAGCAGCCGCAGCACCCGCTGCATGTCACCTACGCCGGGGCGCGTGGACGAGCTGGGCAA
121 ---------+---------+---------+---------+---------+---------+ 180
    CTCGTCGGCGTCGTGGGCGACGTACAGTGGATGCGGCCCCGCGCACCTGCTCGACCCGTT a   E  Q  P  Q  H  P  L  H  V  T  Y  A  G  A  R  G  R  A  G  Q   -

CGTGCTGACGCCCACCCAGGT
181 ---------+---------+- 201
    GCACGACTGCGGGTGGGTCCA a   R  A  D  A  H  P  G   -
```

Fig. 6

(SEQ ID NO: 8)

```
    TCTCAAGAGACTGAACAGAGATGTGAATCTCTGAACACAAGAACAGTTTATTTTTCTGAA
  1 ---------+---------+---------+---------+---------+---------+  60
    AGAGTTCTCTGACTTGTCTCTACACTTAGAGACTTGTGTTCTTGTCAAATAAAAAGACTT a    S  Q  E  T  E  Q  R  C  E  S  L  N  T  R  T  V  Y  F  S  E   -

CAGTGGGTATCTTCCTTAAATGAAAGGGAACAGGAACTTCACAACTTATTGGAGGTTGTA
 61 ---------+---------+---------+---------+---------+---------+ 120
    GTCACCCATAGAAGGAATTTACTTTCCCTTGTCCTTGAAGTGTTGAATAACCTCCAACAT a    Q  W  V  S  S  L  N  E  R  E  Q  E  L  H  N  L  L  E  V  V   -

AGCCAATGTTGTGAGGCTTCAAGTTCAGACATCACTGAGAAATCAGATGGACGTAAGGCA
121 ---------+---------+---------+---------+---------+---------+ 180
    TCGGTTACAACACTCCGAAGTTCAAGTCTGTAGTGACTCTTTAGTCTACCTGCATTCCGT a    S  Q  C  C  E  A  S  S  S  D  I  T  E  K  S  D  G  R  K  A   -

GCTCATGAGAAACAGCATAACATTTTTCTTGATCAGATGACTATTGATGAAGATAAA
181 ---------+---------+---------+---------+---------+------- 237
    CGAGTACTCTTTGTCGTATTGTAAAAAGAACTAGTCTACTGATAACTACTTCTATTT a    A  H  E  K  Q  H  N  I  F  L  D  Q  M  T  I  D  E  D  K   -
```

Fig. 7

(SEQ ID NO: 9)

```
    GAAGATCAAGATACCTCAAAGAATTCTAAGCTAAACTCACACCAGAAAGTAACACTTCTT
 1  ---------+---------+---------+---------+---------+---------+  60
    CTTCTAGTTCTATGGAGTTTCTTAAGATTCGATTTGAGTGTGGTCTTTCATTGTGAAGAA a   E  D  Q  D  T  S  K  N  S  K  L  N  S  H  Q  K  V  T  L  L    -

CAATTGCTACTTGGCCATAAGAATGAAGAAAATGTAGAAAAAAACACCAGCTGCAGGTGA
 61 ---------+---------+---------+---------+---------+---------+  120
    GTTAACGATGAACCGGTATTCTTACTTCTTTTACATCTTTTTTTGTGGTCGACGTCCACT a   Q  L  L  L  G  H  K  N  E  E  N  V  E  K  N  T  S  C  R  *    -

TGATGA
121 ------ 126
    ACTACT a    *  *   -
```

Fig. 8

(SEQ ID NO: 10)

```
    CTTACCTTAGAAAACCAAATTAAAGAAGAAAGAGAACAAGACAACTCTGAATCTCCAAAT
  1 ------------+---------+---------+---------+---------+---------+ 60
    GAATGGAATCTTTTGGTTTAATTTCTTCTTTCTCTTGTTCTGTTGAGACTTAGAGGTTTA a   L  T  L  E  N  Q  I  K  E  E  R  E  Q  D  N  S  E  S  P  N  -

GGCAGAACATCACCTCTTGTGTCCCAGAATAATGAACAAGGCTCAACCTTACGGGATTTG
 61 ------------+---------+---------+---------+---------+---------+ 120
    CCGTCTTGTAGTGGAGAACACAGGGTCTTATTACTTGTTCCGAGTTGGAATGCCCTAAAC a   G  R  T  S  P  L  V  S  Q  N  N  E  Q  G  S  T  L  R  D  L  -

CTGACTACAACAGCTGGAAAGCTACGTGTGGGGTCTACAGATGCTGGCATTGCCTTTGCC
121 ------------+---------+---------+---------+---------+---------+ 180
    GACTGATGTTGTCGACCTTTCGATGCACACCCCAGATGTCTACGACCGTAACGGAAACGG a   L  T  T  T  A  G  K  L  R  V  G  S  T  D  A  G  I  A  F  A  -

CCAGTATATGCAATGGGAGCCCCAAGTAGCAAAAGTGGACGGACTATGCCTAACATTCTT
181 ------------+---------+---------+---------+---------+---------+ 240
    GGTCATATACGTSACCCTCGGGGSTCATCGSSTTCACC~GCCT&ATACGGATSGTAAGAA a   P  V  Y  A  M  G  A  P  S  S  K  S  G  R  T  M  P  N  I  L  -

GATGACATAATTGCTTCAGTTGTTGAAAACAAAATTCCACCAAGTAAAACCTCCAAGATA
241 ------------+---------+---------+---------+---------+---------+ 300
    CTACTGTATTAACGAAGTCAACAACTTTTGTTTSAAGGTGGTTCATTTTGGAGGTTCTAT a   D  D  I  I  A  S  V  V  E  N  K  I  P  P  S  K  T  S  K  I  -

AATGTAAAACCAGAGCTTAAAGAAGAGCCTGAAGAAAGCATAATATCTGCAGTGGATGAA
301 ------------+---------+---------+---------+---------+---------+ 360
    TTACATTTTGGTCTCGAATTTCTTCTCGGACTTCTTTCGTATTATAGACGTCACCTACTT a   N  V  K  P  F  L  K  E  E  P  E  E  S  I  I  S  A  V  D  E  -

AATAATAAATTATACAGTGATATACCACATTCTTGGATCTGTGAGAAGCATATTTTATGG
361 ------------+---------+---------+---------+---------+---------+ 420
    TTATTATTTAATATGTCACTATATGGTGTAAGAACCTAGACACTCTTCGTATAAAATACC a   N  N  K  L  Y  S  D  I  P  H  S  W  I  C  E  K  H  I  L  W  -

CTTAGGATTATAAGAATAGCAGTAATTGGAAGCTTTTCAAAGAATGTTGGAAACAACGAC
421 ------------+---------+---------+---------+---------+---------+ 480
    GAATCCTAATATTCTTATCGTCATTAACCTTCGAAAAGTTTCTTACAACCTTTGTTGCTG a   L  R  I  I  R  I  A  V  I  G  S  F  S  K  N  V  G  N  K  D  -

AGCCTGCAGTGGTTTCTGGTGTGCATAAGAAAATGAACATTAGCCTATGGAAGGCGGAAT
481 ------------+---------+---------+---------+---------+---------+ 540
    TCGGACGTCACCAAAGACCACACGTATTCTTTTACTTGTAATCGGATACCTTCCGCCTTA a   S  L  Q  W  F  L  V  C  I  R  K  *  T  L  A  Y  G  R  R  N  -

CAATTAGTCTTGATTTTGGAGACCACCAAG
541 ------------+---------+--------+ 570
    GTTAATCAGAACTAAAACCTCTGGTGGTTC a   Q  L  V  L  I  L  E  T  T  K  -
```

Fig. 9

(SEQ ID NO: 11)

```
     AACCATACCCCTGGCGCCTTGTACCCCGATTCCGACTTGGAGAAGGAAGAAGAGGAGAGT
   1 ---------+---------+---------+---------+---------+---------+  60
     TTGGTATGGGGACCGCGGAACATGGGGCTAAGGCTGAACCTCTTCCTTCTTCTCCTCTCA a    N  H  T  P  G  A  L  Y  P  D  S  D  L  E  K  E  E  E  S      -

GAGGAGGACTGGAAGCTGCAGCTGGAGGCTGAAAACTACGAGGGCCACACCCCACTCCAC
  61 ---------+---------+---------+---------+---------+---------+ 120
     CTCCTCCTGACCTTCGACGTCGACCTCCGACTTTTGATGCTCCCGGTGTGGGGTGAGGTG a    E  E  D  N  K  L  Q  L  E  A  E  N  Y  E  G  H  T  P  L  H   -

GTGGCCGTTATCCACAAAGATGTGGAGATGGTCCGGCTGCTCCGAGATGCTGGAGCTGAC
 121 ---------+---------+---------+---------+---------+---------+ 180
     CACCGGCAATAGGTGTTTCTACACCTCTACCAGGCCGACGAGGCTCTACGACCTCGACTG a    V  A  V  I  H  K  D  V  E  M  V  R  L  L  R  D  A  G  A  D   -

CTTGACAAACCGGAGCCCACGTGCGGCCGGAGCCCCTTCATTTGGCAGTGGAGGCCAGGC
 181 ---------+---------+---------+---------+---------+---------+ 240
     GAACTGTTTGGCCTCGGGTGCACGCCGGCCTCGGGGAAGTAAACCGTCACCTCCGGTCCG a    L  D  K  P  E  P  T  C  G  R  S  P  F  I  W  Q  W  R  P  G   -

AGCCGATGTGCTGGAGCTTCTCTGAGGGCAGGCGCGAACCCTGCTGCCCGCATGTACGGT
 241 ---------+---------+---------+---------+---------+---------+ 300
     TCGGCTACACGACCTCGAAGAGACTCCCGTCCGCGCTTGGGACGACGGGCGTACATGCCA a    S  R  C  A  G  A  S  L  R  A  G  A  N  P  A  A  R  M  Y  G   -

GGCCGCACCCCACTCGGCAGTGCCATGCTCCGGCCCAACCCCATCCTCGCCCGCCTCCTC
 301 ---------+---------+---------+---------+---------+---------+ 360
     CCGGCGTGGGGTGAGCCGTCACGGTACGAGGCCGGGTTGGGGTAGGAGCGGGCGGAGGAG a    G  R  T  P  L  G  S  A  M  L  R  P  N  P  I  L  A  R  L  L   -

CGTGCACACGGAGCCCCTGAGCCCGAGGGGAAGGACGAGAAATCCGGCCCCTGCAGCAGC
 361 ---------+---------+---------+---------+---------+---------+ 420
     GCACGTGTGCCTCGGGGACTCGGGCTCCCCTTCCTGCTCTTTAGGCCGGGGACGTCGTCG a    R  A  H  G  A  P  E  P  E  G  K  D  E  K  S  G  P  C  S  S   -

AGTAGCGAGCACGACNAGAGANGACGAgggcGATGAATACGACGACATTGTGGTTCACAG
 421 ---------+---------+---------+---------+---------+---------+ 480
     TCATCGCTCGTGCTGNTCTCTNCTGCTcccgCTACTTATGCTGCTGTAACACCAAGTGTC a    S  S  E  H  D  ?  R  ?  R  G  R  *  I  R  R  H  C  G  S  Q   -

CAGCCGCAGCCAAACCCGGCTGCCTCCCACCCCAGCCTCAAAACCTCTTCCTGACGACCC
 481 ---------+---------+---------+---------+---------+---------+ 540
     GTCGGCGTCGGTTTGGGCCGACGGAGGGTGGGGTCGGAGTTTTGGAGAAGGACTGCTGGG a    Q  P  Q  P  N  P  A  A  S  H  P  S  L  K  T  S  S  *  R  P   -

CCGCCCCGTGTGATTTGTTTCATTGTTAATATAATTTCCAGTTTAATAAACAAAACCCTA
```

Fig. 10A

```
541 ---------+---------+---------+---------+---------+---------+ 600
    GGCGGGGCACACTAAACAAAGTAACAATTATATTAAAGGTCAAATTATTTGTTTTGGGAT
a    P  P  R  V  I  C  F  I  V  N  I  I  S  S  L  I  N  K  T  L

GTTCTGACAACCAGAAAAAAAAAA
601 ---------+---------+---- 624
    CAAGACTGTTGGTCTTTTTTTTTT
a    V  L  T  T  R  K  K  K  -
```

Fig. 10B (SEQ ID NO. 12)

```
    AGACACCCGCTGATCAGAGACATGCTTCGACGAATTAAGGAAGAAGAGGATCTGGGTAAA
1   ---------+---------+---------+---------+---------+---------+ 60
    TCTGTGGGCGACTAGTCTCTGTACGAAGCTGCTTAATTCCTTCTTCTCCTAGACCCATTT a    R  H  P  L  I  R  D  M  L  R  R  I  K  E  E  E  D  L  G  K  -

AGTAGAGAAGGATCAAGGACGGATGATGAAGTAGTACAG
61   ---------+---------+---------+--------- 99
     TCATCTCTTCCTAGTTCCTGCCTACTACTTCATCATGTC a    S  R  E  G  S  R  T  D  D  E  V  V  Q   -
```

Fig. 11

(SEQ ID NO. 13)

```
    CAGGTGGAAGAAAACACCCCGTACTGGCAGGCATGGAGCCAACAAGGAGAACCTGGAGCT
  1 ---------+---------+---------+---------+---------+---------+ 60
    GTCCACCTTCTTTTGTGGGGCATGACCGTCCGTACCTCTGTTGTTCCTCTTGGACCTCCA a   Q  V  E  E  N  T  P  Y  W  Q  A  W  S  Q  Q  G  E  P  G  A  -

CAACGGCAGCATCCTGAGTGCGAGAACTTTCAAAGGCTTCCAAATCTGATGCTACTTCTG
 61 ---------+---------+---------+---------+---------+---------+ 120
    GTTGCCGTCGTAGGACTCACGCTCTTGAAAGTTTCCGAAGGTTTAGACTACGATGAAGAC a   Q  R  Q  H  P  E  C  E  N  F  Q  R  L  P  N  L  M  L  L  L  -

GAATCCTCAATTCAACCAACATCCAGTCCTGAGAAGCCCTGATCAGTCAACCAGCTGTGG
121 ---------+---------+---------+---------+---------+---------+ 180
    CTTAGGAGTTAAGTTGGTTGTAGGTCAGGACTCTTCGGGACTAGTCAGTTGGTCGACACC a   E  S  S  I  Q  P  T  S  S  P  E  K  P  *  S  V  N  Q  L  W  -

CTTCCTGTGCCTAGACTGGACCTAATTATATGGGGG
181 ---------+---------+---------+------ 216
    GAAGGACACGGATCTGACCTGGATTAATATACCCCC a   L  P  V  P  R  L  D  L  I  I  W  G  -
```

Fig. 12

(SEQ ID NO. 14)

```
      TGCCGCTGCAGCAGCGCAGTTCCAGTCCGTTGCTTTACTTTTTGCTTCACCGACATAGTC
   1  ------------+---------+---------+---------+---------+---------+  60
      ACGGCGACGTCGTCGCGTCAAGGTCAGGCAACGAAATGAAAAACGAAGTGGCTGTATCAG a     C  R  C  S  S  A  V  P  V  R  C  F  T  F  C  F  T  D  I  V  -

ATTATGCCGAAGAGAAAGTCTCCAGAGAATACAGAGGGCAAAGATGGATCCAAAGTAACT
  61  ------------+---------+---------+---------+---------+---------+  120
      TAATACGGCTTCTCTTTCAGAGGTCTCTTATGTCTCCCGTTTCTACCTAGGTTTCATTGA a     I  M  P  K  R  K  S  P  E  N  T  E  G  K  D  G  S  K  V  T  -

AAACAGGAGCCCACAAGACGGTCTGCCAGATTGTCAGCGAAACCTGCTCCACCAaaacct
 121  ------------+---------+---------+---------+---------+---------+  180
      TTTGTCCTCGGGTGTTCTGCCAGACGGTCTAACAGTCGCTTTGGACGAGGTGGTtttgga a     K  Q  E  P  T  A  R  R  A  R  L  S  A  K  P  A  P  P  K  P  - gaacccaaaccaagaaaaacatctgctaagaaagaacctGGAGCAAAGATTAGCAGAGGT
 181  ------------+---------+---------+---------+---------+---------+  240
      cttgggtttggttcttttgtagacgattctttcttggaCCTCGTTTCTAATCGTCTCCA a     E  P  K  P  A  R  T  S  A  K  K  E  P  G  A  K  I  S  R  G  -

GCTAAAGGGAGGAAGGAGGAAAAGCAGGAAGCTGGAAAGGAAGGTACTGCACCATCTGAA
 241  ------------+---------+---------+---------+---------+---------+  300
      CGATTTCCCTCCTTCCTCCTTTTCGTCCTTCGACCTTTCCTTCCATGACGTGGTAGACTT a     A  K  G  R  K  E  E  K  Q  E  A  G  K  E  G  T  A  P  S  E  -

AATGGTGAAACTAAAGCTGAAGAGGCACAGAAAACTGAATCTGTAGATAACGAGGGAGAA
 301  ------------+---------+---------+---------+---------+---------+  360
      TTACCACTTTGATTTCGACTTCTCCGTGTCTTTTGACTTAGACATCTATTGCTCCCTCTT a     N  G  E  T  K  A  E  E  A  Q  K  T  E  S  V  D  N  E  G  E  -

TGAATTGTCATGAAAAATTGGGGTTGATTTTATGTATCTCTTGGGACAACTTTTAAAAGC
 361  ------------+---------+---------+---------+---------+---------+  420
      ACTTAACAGTACTTTTTAACCCCAACTAAAATACATAGAGAACCCTGTTGAAAATTTTCG a     *  I  V  M  K  N  W  G  *  F  Y  V  S  L  G  T  T  F  K  S  -

TATTTTTACCAAGTATTTTGTAAATGCTAATTTTTTAGGACTCTACTAGTTGGCATACGA
 421  ------------+---------+---------+---------+---------+---------+  480
      ATAAAAATGGTTCATAAAACATTTACGATTAAAAAATCCTGAGATGATCAACCGTATGCT a     Y  F  Y  Q  V  F  C  K  C  *  F  F  R  T  L  L  V  G  I  R  -

AAATATATAAGGATGGACATTTATCGTCTCATAGTCATGCTTTTTGGAATTTNNNNNNNN
 481  ------------+---------+---------+---------+---------+---------+  540
      TTTATATATTCCTACCTGTAAATAGCAGAGTATCAGTACGAAAAACCTTAAANNNNNNNN a     K  Y  I  R  M  D  I  Y  R  L  I  V  M  L  F  G  I  ?  ?  ?  -

NNNNNNNNNNNNNNNNNNNNNNNCAGGAAGTTTGCCCCAAGATGCTCAGTGTGCCGTGGGGCCA
 541  ------------+---------+---------+---------+---------+---------+  600
      NNNNNNNNNNNNNNNNNNNNNNNGTCCTTCAAACGGGGTTCTACGAGTCACACGGCACCCCGGT
```

Fig. 13A

```
a       ? ? ? ? ? ? ? G S L P Q D A Q C A V G P   -
        TAACTGCCTGAGCCAGGTCAGGAGGAGACTGCTG
   601  ---------+---------+---------+----  634
        ATTGACGGACTCGGTCCAGTCCTCCTCTGACGAC a       * L P E P G Q E E T A   -
```

Fig. 13B (SEQ ID NO. 15)

```
     AAACATCCTATCATCTGTAGGCTCATTCATTTCTCTAACAGCAGCAGCAACAGCGCATCA
   1 ---------+---------+---------+---------+---------+---------+  60
     TTTGTAGGATAGTAGACATCCGAGTAAGTAAAGAGATTGTCGTCGTCGTTGTCGCGTAGT a     K  H  P  I  I  C  R  L  I  H  F  S  N  S  S  S  N  S  A  S   -

CAGGACACCAAGGAGAGCTCTGAAGAGCCTCCCTCAGAAGAGAGCCAGGACACCCCCATT
  61 ---------+---------+---------+---------+---------+---------+ 120
     GTCCTGTGGTTCCTCTCGAGACTTCTCGGAGGGAGTCTTCTCTCGGTCCTGTGGGGGTAA a     Q  D  T  K  E  S  S  E  E  P  P  S  E  E  S  Q  D  T  P  I   -

TACACGGAGTTTGATGAGGATTTCGAGGAGGAACCCACATCCCCCATAGGTCACTGTGTG
 121 ---------+---------+---------+---------+---------+---------+ 180
     ATGTGCCTCAAACTACTCCTAAAGCTCCTCCTTGGGTGTAGGGGGTATCCAGTGACACAC a     Y  T  E  F  D  E  D  F  E  E  E  P  T  S  P  I  G  H  C  V   -

GCCATCTACCACTTTGAAGGGTCCAGCGAGGGCACTATCTCTATGGCCGAGGGTGAAGAC
 181 ---------+---------+---------+---------+---------+---------+ 240
     CGGTAGATGGTGAAACTTCCCAGGTCGCTCCCGTGATAGAGATACCGGCTCCCACTTCTG a     A  I  Y  H  F  E  G  S  S  E  G  T  I  S  M  A  E  G  E  D   -

CTCAGTCTTATGGAAGAAGACAAAGGGGACGGCTGGACCCGGGTCAGGCGGAAAGAGGGA
 241 ---------+---------+---------+---------+---------+---------+ 300
     GAGTCAGAATACCTTCTTCTGTTTCCCCTGCCGACCTGGGCCCAGTCCGCCTTTCTCCCT a     L  S  L  M  E  E  D  K  G  D  G  W  T  R  V  R  R  K  E  G   -

GGCGAGGGCTACGTGCCCACCTCCTACCTCCGAGTCACGCTCAATTGAACCCTGCCAGAG
 301 ---------+---------+---------+---------+---------+---------+ 360
     CCGCTCCCGATGCACGGGTGGAGGATGGAGGCTCAGTGCGAGTTAACTTGGGACGGTCTC a     G  E  G  Y  V  P  T  S  Y  L  R  V  T  L  N  *  T  L  P  E   -

ACGGGAAGAGGGGGGCTGTCGGCTGCTGCTTCTGGGCCACGGGGAGCCCCAGGACCTATG
 361 ---------+---------+---------+---------+---------+---------+ 420
     TGCCCTTCTCCCCCCGACAGCCGACGACGAAGACCCGGTGCCCCTCGGGGTCCTGGATAC a     T  G  R  G  G  L  S  A  A  A  S  G  P  R  G  A  P  G  P  M   -

CACTTTATTTCTGACCCCGTGGCTTCGGCTGAGACCTGTGTAACCTGCTGCCCCCTCCAC
 421 ---------+---------+---------+---------+---------+---------+ 480
     GTGAAATAAAGACTGGGGCACCGAAGCCGACTCTGGACACATTGGACGACGGGGGAGGTG a     H  F  I  S  D  P  V  A  S  A  E  T  C  V  T  C  C  P  L  H   -

CCCCAACCCAGTCCTACCTGTCACACCGGACGGACCCGCTGTGCCTTCTACCATCGTTCC
 481 ---------+---------+---------+---------+---------+---------+ 540
     GGGGTTGGGTCAGGATGGACAGTGTGGCCTGCCTGGGCGACACGGAAGATGGTAGCAAGG a     P  Q  P  S  P  T  C  H  T  G  R  T  R  C  A  F  Y  H  R  S   -

ACCATTGATGTACATACTCATGTTTTACATCTTTTCTTTCTGCGCTCGGCTCCGGCCATT
 541 ---------+---------+---------+---------+---------+---------+ 600
     TGGTAACTACATGTATGAGTACAAAATGTAGAAAAGAAAGACGCGAGCCGAGGCCGGTAA
```

Fig. 14A

```
a     T  I  D  V  H  T  H  V  L  H  L  F  F  L  R  S  A  P  A  I   -
      TTGTTTTATACAAAAATGGGAAAAAAAAAAAAAAAAAA
601   ----------+---------+---------+-------- 638
      AACAAAATATGTTTTTACCCTTTTTTTTTTTTTTTTTT a     L  F  Y  T  K  M  G  K  K  K  K         -
```

Fig. 14B (SEQ ID NO. 16)

```
      GGCACGAGGCGTGACGTCCGACAAGAAATGCTGGATGATGTACAAAAGAAATTGATGAGC
   1  ---------+---------+---------+---------+---------+---------+ 60
      CCGTGCTCCGCACTGCAGGCTGTTCTTTACGACCTACTACATGTTTTCTTTAACTACTCG a     G  T  R  R  D  V  R  Q  E  M  L  D  D  V  Q  K  K  L  M  S  -

TTAGCAAACAGCTCAGAAGGAAAAGTAGACAAAGTCCTAATGAGAAACCTCTTCATTGGT
  61  ---------+---------+---------+---------+---------+---------+ 120
      AATCGTTTGTCGAGTCTTCCTTTTCATCTGTTTCAGGATTACTCTTTGGAGAAGTAACCA a     L  A  N  S  S  E  G  K  V  D  K  V  L  M  R  N  L  F  I  G  -

CATTTCCACACACCGAAAAATCAGCGTCATGAAGTGTTACGGTTAATGGGGAGCATCCTG
 121  ---------+---------+---------+---------+---------+---------+ 180
      GTAAAGGTGTGTGGCTTTTTAGTCGCAGTACTTCACAATGCCAATTACCCCTCGTAGGAC a     H  F  H  T  P  K  N  Q  R  H  E  V  L  R  L  M  G  S  I  L  -

GGCGTCAGAAGGGAGGAGATGGAGCAGTTGTTTCATGACGATCAGGGCAGTGTTACCAGG
 181  ---------+---------+---------+---------+---------+---------+ 240
      CCGCAGTCTTCCCTCCTCTACCTCGTCAACAAAGTACTGCTAGTCCCGTCACAATGGTCC a     G  V  R  R  E  E  M  E  Q  L  F  H  D  D  Q  G  S  V  T  R  -

TGGATGACTGGGTGGCTTGGAGGAGGATCAAAAAGTGTTCCCAACACACCTTTGAGACCA
 241  ---------+---------+---------+---------+---------+---------+ 300
      ACCTACTGACCCACCGAACCTCCTCCTAGTTTTTCACAAGGGTTGTGTGGAAACTCTGGT a     W  M  T  G  W  L  G  G  G  S  K  S  V  P  N  T  P  L  R  P  -

AATCAGCAATCTGTGGTTAATAGTTCTTTTTCAGAACTTTTTGTTAAATTTCTAGAAACA
 301  ---------+---------+---------+---------+---------+---------+ 360
      TTAGTCGTTAGACACCAATTATCAAGAAAAAGTCTTGAAAAACAATTTAAAGATCTTTGT a     N  Q  Q  S  V  V  N  S  S  F  S  E  L  F  V  K  F  L  E  T  -

GAATCTCATCCATCCATTCCACCACCAAAGCTTTCTGTTCATGATATGAAACCTCTGGAT
 361  ---------+---------+---------+---------+---------+---------+ 420
      CTTAGAGTAGGTAGGTAAGGTGGTGGTTTCGAAAGACAAGTACTATACTTTGGAGACCTA a     E  S  H  P  S  I  P  P  P  K  L  S  V  H  D  M  K  P  L  D  -

TCACCAGGAAGAAGAAAAAGAGATACAAATGCACCAGAAAGTTTTAAAGATACAGCAGAA
 421  ---------+---------+---------+---------+---------+---------+ 480
      AGTGGTCCTTCTTCTTTTTCTCTATGTTTACGTGGTCTTTCAAAATTTCTATGTCGTCTT a     S  P  G  R  R  K  R  D  T  N  A  P  E  S  F  K  D  T  A  E  -

TCCAGGTCTGGTAGAAGAACAGATGTAAATCCGTTTTTGGCTCCTcgctcggcagctgta
 481  ---------+---------+---------+---------+---------+---------+ 540
      AGGTCCAGACCATCTTCTTGTCTACATTTAGGCAAAAACCGAGGAgcgagccgtcgacat a     S  R  S  G  R  R  T  D  V  N  P  F  L  A  P  R  S  A  A  V  - cctcttattaacccagctggacttggacttggtgggccgggcatcttcttctgaaaccca
 541  ---------+---------+---------+---------+---------+---------+ 600
      ggagaataattgggtcgacctgaacctggaccacccggcccgtagaagaagactttgggt
```

Fig. 15A

```
a     P  L  I  N  P  A  G  L  G  P  G  G  P  G  I  F  F  *  N  P  -
      tctcagatgttttgcccacatttacacctttgccagcgttacctgacaacagtgctgggg
  601 ---------+---------+---------+---------+---------+---------+ 660
      agagtctacaaaacgggtgtaaatgtggaaacggtcgcaatggactgttgtcacgacccc a     S  Q  M  F  C  P  H  L  H  L  C  Q  R  Y  L  T  T  V  L  G  -
      ttgtgctgaaagccttttaaagcaatagatgattctcaagccagagacaatctagcactt
  661 ---------+---------+---------+---------+---------+---------+ 720
      aacacgactttcggaaaatttcgttatctactaagagttcggtctctgttagatcgtgaa a     L  C  *  K  P  F  K  A  I  D  D  S  Q  A  R  D  N  L  A  L  -
      taaagaaaccatgaacactatatgtatgtactttatcacaaagtggcctttggggagaaa
  721 ---------+---------+---------+---------+---------+---------+ 780
      atttctttggtacttgtgatatacatacatgaaatagtgtttcaccggaaacccctcttt a     *  R  N  H  E  H  Y  M  Y  V  L  Y  H  K  V  A  F  G  E  K  -
      gtcatgtatttgttcgcaattatgctttctctgaatttaataaaaatattcctaatgctt
  781 ---------+---------+---------+---------+---------+---------+ 840
      cagtacataaacaagcgttaatacgaaagagacttaaattattttataaggattacgaa a     V  M  Y  L  F  A  I  M  L  S  L  N  L  I  K  I  F  L  M  L  -
      ttagaaaaaaaaaaaaaaaaaa
  841 ---------+---------+-- 862
      aatctttttttttttttttttt a     L  E  K  K  K  K  K     -
```

Fig. 15B (SEQ ID NO: 17)

```
    GGCACGAGGCGAGTTCTCCCACCTGAGCAGAAATATGACCATGCAGCGCACCATGAAGCT
  1 ---------+---------+---------+---------+---------+---------+ 60
    CCGSGCTCCGCTCAAGAGGGUGGACSCGTCT$TATACTGG$ACGTCGCGTGGTAC$$CGA a   G  T  R  R  V  L  P  P  E  Q  K  Y  D  H  A  A  H  H  E  A   -

CTACCGACTGCCAGAGACTCCCAAGACAGCTGGGCTGCGACCAATGGAAACAAAGGACAT
 61 ---------+---------+---------+---------+---------+---------+ 120
    GATGGCTGACGGTCTCTGAGGGTTCTGTCGACCCGACGCTGGTTACCTTTGTTTCCTGTA a   L  P  T  A  R  D  S  Q  D  S  W  A  A  T  N  G  N  K  G  H   -

TCCAGTAGTGCACCAGCTCCTCACCAGGTACTTGAAGCAATTTCACCTTACGCCCGTCAT
121 ---------+---------+---------+---------+---------+---------+ 180
    AGGTCATCACGTGGTCGAGGAGTGGTCCATGAACTTCGTTAAAGTGGAATGCGGGCAGTA a   S  S  S  A  P  A  P  H  Q  V  L  E  A  I  S  P  Y  A  R  H   -

GAGCCAGGAGGAGGTGGAGCACTGGTTCTACCCCCAGGAGAATATCATCGACACTTTCGT
181 ---------+---------+---------+---------+---------+---------+ 240
    CTCGGTCCTCCTCCACCTCGTGACCAAGATGGGGGTCCTCTTATAGTAGCTGTGAAAGCA a   E  P  G  G  G  A  L  V  L  P  P  G  E  Y  H  R  H  F  R   -

GGSGGAG
241 ------- 247
    CCACCTC a   G  G   -
```

Fig. 16

(SEQ ID NO: 18)

```
    agggcgcacctggagctgTTCTGGTCTAGAGTGAATATCCCCAAGGTGCTAAGAGCTGCA
 1  ---------+---------+---------+---------+---------+---------+ 60
    tcccgcgtggacctcgacAAGACCAGATCTCACTTATAGGGGTTCCACGATTCTCGACGT a    R  A  H  L  E  L  F  W  S  R  V  N  I  P  K  V  L  R  A  A   -

GAACAAGCTCATCTTTGGGCAGACTGGTGTTTTTGTATGACA
 61 ---------+---------+---------+---------+-- 102
    CTTGTTCGAGTAGAAACCCGTCTGACCACAAAAACATACTGT a    E  Q  A  H  L  W  A  D  W  C  F  C  M  T   -
```

Fig. 17

(SEQ ID NO: 19)

```
    GTTAGCTCTAGAGGCCATTCTTTTGCTGATCCTGCCAGTAATCTTGGGCTGGAAGACATT
  1 ---------+---------+---------+---------+---------+---------+ 60
    CAATCGAGATCTCCGGTAAGAAAACGACTAGGACGGTCATTAGAACCCGACCTTCTGTAA a   V  S  S  R  G  H  S  F  A  D  P  A  S  N  L  G  L  E  D  I  -

ATCAGGAAGGCTCTCATGGGAAGCTTTGATGACAAAGTTGAGGATCATGGAGTTGTCATG
 61 ---------+---------+---------+---------+---------+---------+ 120
    TAGTCCTTCCGAGAGTACCCTTCGAAACTACTGTTTCAACTCCTAGTACCTCAACAGTAC a   I  R  K  A  L  M  G  S  F  D  D  K  V  E  D  H  G  V  V  M  -

TCCCAGCCTATGGGAGTAGTGCCTGGTACTGCCAACACCGATTGCATGTGCTCCCTCTGC
121 ---------+---------+---------+---------+---------+---------+ 180
    AGGGTCGGATACCCTCATCACGGACCATGACGGTTGTGGCTAACGTACACGAGGGAGACG a   S  Q  P  M  G  V  V  P  G  T  A  N  T  D  C  M  C  S  L  C  -

GGTGAACCAAGCAGCTCCTCACCAACAGAACAGGATCTG
181 ---------+---------+---------+--------- 219
    CCACTTGGTTCGTCGAGGAGTGGTTGTCTTGTCCTAGAC a   G  E  P  S  S  S  S  P  T  E  Q  D  L  -
```

Fig. 18

(SEQ ID NO: 20)

```
    AATATCGAACTGAAGAAAGGAGGGAAGGATATACCAGTCACTATCCACAATTTAGAGGAG
  1 ---------+---------+---------+---------+---------+---------+ 60
    TTATAGCTTGACTTCTTTCCTCCCTTCCTATATGGTCAGTGATAGGTGTTAAATCTCCTC a   N  I  E  L  K  K  G  G  K  D  I  P  V  T  I  H  N  L  E  E    -

TATCTAAGACTGGTTATATTCTGGGCACTAAATGAAGGCGTTTCTAGGCAATTTGATTCG
 61 ---------+---------+---------+---------+---------+---------+ 120
    ATAGATTCTGACCAATATAAGACCCGTGATTTACTTCCGCAAAGATCCGTTAAACTAAGC a   Y  L  R  L  V  I  F  W  A  L  N  E  G  V  S  R  Q  F  D  S    -

TTCAGAGATGGATTTGAATCAGTCTTCCCACTCAGTCATCTTCAGTACTTCTACCCGGAG
121 ---------+---------+---------+---------+---------+---------+ 180
    AAGTCTCTACCTAAACTTAGTCAGAAGGGTGAGTCAGTAGAAGTCATGAAGATGGGCCTC a   F  R  D  G  F  E  S  V  F  P  L  S  H  L  Q  Y  F  Y  P  E    -

GAACTGGATCAGCTCCTTTGTGGCAGTAAAGCAGACACTTGGGATGCAAAGACACTGATG
181 ---------+---------+---------+---------+---------+---------+ 240
    CTTGACCTAGTCGAGGAAACACCGTCATTTCGTCTGTGAACCCTACGTTTCTGTGACTAC a   E  L  D  Q  L  L  C  G  S  K  A  D  T  W  D  A  K  T  L  M    -

GAATGCTGTAGGCCTGATCATGGTTATACTCATGACAGTCGGGCTGTGAAGTTTTTGTTT
241 ---------+---------+---------+---------+---------+---------+ 300
    CTTACGACATCCGGACTAGTACCAATATGAGTACTGTCAGCCCGACACTTCAAAAACAAA a   E  C  C  R  P  D  H  G  Y  T  H  D  S  R  A  V  K  F  L  F    -

GAGATTCTCAGTAGTTTTGATAATGAGCAGCAGAGGTTATTTCTCCAGTTTGTGACTGGT
301 ---------+---------+---------+---------+---------+---------+ 360
    CTCTAAGAGTCATCAAAACTATTACTCGTCGTCTCCAATAAAGAGGTCAAACACTGACCA a   E  I  L  S  S  F  D  N  E  Q  Q  R  L  F  L  Q  F  V  T  G    -

AGCCCAAGATTGCCTGTTGGAGGATTCCGGAGTTTGAATCCACCTTTGACAATTGTCCGA
361 ---------+---------+---------+---------+---------+---------+ 420
    TCGGGTTCTAACGGACAACCTCCTAAGGCCTCAAACTTAGGTGGGAAACTGTTAACAGCT a   S  P  R  L  P  V  G  G  F  R  S  L  N  P  P  L  T  I  V  R    -

AAGACGTTTGAATCAACAGAAAACCCAGATGACTTCTTGCCCTCTGTAATGACTTGTGTG
421 ---------+---------+---------+---------+---------+---------+ 480
    TTCTGCAAACTTAGTTGTCTTTTGGGTCTACTGAAGAACGGGAGACATTACTGAACACAC a   K  T  F  E  S  T  E  N  P  D  D  F  L  P  S  V  M  T  C  V    -

AACTATCTTAAGTTGCCGGACTATCAAGCATTGAGATATGCGTGAAAAACTGTTGATAGC
481 ---------+---------+---------+---------+---------+---------+ 540
    TTGATAGAATTCAACGGCCTGATAGTTCGTAACTCTATACGCACTTTTTGACAACTATCG a   N  Y  L  K  L  P  D  Y  Q  A  L  R  Y  A  *  K  T  V  D  S    -

AGCAAGAGAAGGG
541 ---------+--- 553
    TCGTTCTCTTCCC a   S  K  R  R    -
```

Fig. 19

(SEQ ID NO. 21)

```
     GAAGCAAAAAACGAGCCCTGGAAGAAGAAAAACCACGCCGGGAAATCCTGGAAAAACGAT
  1  ------------+---------+---------+---------+---------+---------+  60
     CTTCGTTTTTTGCTCGGGACCTTCTTCTTTTTGGTGCGGCCCTTTAGGACCTTTTTGCTA a    E  A  K  N  E  P  W  K  K  K  N  H  A  G  K  S  W  K  N  D   -

TACAGGAAGAAACTAGCCAGAGGAGAAGTTAATAGAAAAGGAAGTAAAAATAAGGGAGAG
 61  ------------+---------+---------+---------+---------+---------+ 120
     ATGTCCTTCTTTGATCGGTCTCCTCTTCAATTATCTTTTCCTTCATTTTTATTCCCTCTC a    Y  R  K  K  L  A  R  G  E  V  N  R  K  G  S  K  N  G  E   -

AGAAAGGGCACAGGCTCGTCCTTTGACACGCTACCTGCCTGTCCGGAAGAAGACTTTGAT
121  ------------+---------+---------+---------+---------+---------+ 180
     TGTTTCCCGTGTCCGAGCAGGAAACTGTGCGATGGACGGACAGGCCTTCTTCTGAAACTA a    T  K  G  T  G  S  S  F  D  T  L  P  A  C  P  E  E  D  F  D   -

TSGCGG
181  ------ 186
     AACGCC a    L  R   -
```

Fig. 20

(SEQ ID NO. 22)

```
    AGGGTACgGGAAGCTGCTGAAAAGGCTAAGTCTGAACTCTCCTCATCTGTGCAGACTGAC
 1  ---------+---------+---------+---------+---------+---------+ 60
    TCCCATGcCCTTCGACGACTTTTCCGATTCAGACTTGAGAGGAGTAGACACGTCTGACTG a   R  V  R  E  A  A  E  K  A  K  S  E  L  S  S  S  V  Q  T  D  -

ATCAAT
 61 ------ 66
    TAGTTA a   I  N  -
```

Fig. 21

(SEQ ID NO. 23)

```
      CATTTGAATATGAAGTTGACCCGTGCTCAATTTGAAGGGATTGTCACTGATCTAATCAGA
    1 ---------+---------+---------+---------+---------+---------+ 60
      GTAAACTTATACTTCAACTGGGCACGAGTTAAACTTCCCTAACAGTGACTAGATTAGTCT a     H  L  N  M  K  L  T  R  A  Q  F  E  G  I  V  T  D  L  I  R   -

AGGACTATCGCTCCATGCCAAAAAGCTATGCAAGATGCAGAAGTCAGCAAGAGTGACATA
   61 ---------+---------+---------+---------+---------+---------+ 120
      TCCTGATAGCGAGGTACGGTTTTTCGATACGTTCTACGTCTTCAGTCGTTCTCACTGTAT a     R  T  I  A  P  C  Q  K  A  M  Q  D  A  E  V  S  K  S  D  I   -

GGAGAAGTGATTCTTGTGGGTGGCATGACTAGGATGCCCAAGGTTCAGCAGACTGTACAG
  121 ---------+---------+---------+---------+---------+---------+ 180
      CCTCTTCACTAAGAACACCCACCGTACTGATCCTACGGGTTCCAAGTCGTCTGACATGTC a     G  E  V  I  L  V  G  G  M  T  R  M  P  K  V  Q  Q  T  V  Q   -

GACTTTTTGGCA
  181 ---------+-- 192
      CTGAAAAACCGT a     D  F  L  A   -
```

Fig. 22

(SEQ ID NO. 24)

```
      GGGGGCAGTGGACGAGGCCGTGGCGACCTGAAGCAGGCGCTTCCCTGTGTGGCCGAGTCG
   1  ------------+---------+---------+---------+---------+---------+  60
      CCCCCGTCACCTGCTCCGGCACCGCTGGACTTCGTCCGCGAAGGGACACACCGGCTCAGC a     G  G  S  G  R  G  R  G  D  L  K  Q  A  L  P  C  V  A  E  S   -

CCAACGGTCCACGTGGAGGTGCATCAGCGCGGCAGCAGCACTGCAAAGAAAGAAGACATA
  61  ------------+---------+---------+---------+---------+---------+  120
      GGTTGCCAGGTGCACCTCCACGTAGTCGCGCCGTCGTCGTGACGTTTCTTTCTTCTGTAT a     P  T  V  H  V  E  V  H  Q  R  G  S  S  T  A  K  K  E  D  I   -

AACCTGAGTGTTAGAAAGCTACTCAACAGACATAATATTGTGTTTGGCGATTACACATGG
 121  ------------+---------+---------+---------+---------+---------+  180
      TTGGACTCACAATCTTTCGATGAGTTGTCTGTATTATAACACAAACCGCTAATGTGTACC a     N  L  S  V  R  K  L  L  N  R  H  N  I  V  F  G  D  Y  T  W   -

ACTGAGTTTGATGAACCTTTTTTGACCAGAAATGTGCAGTCTGTGTCTATTATTGACACA
 181  ------------+---------+---------+---------+---------+---------+  240
      TGACTCAAACTACTTGGAAAAAACTGGTCTTTACACGTCAGACACAGATAATAACTGTGT a     T  E  F  D  E  P  F  L  T  R  N  V  Q  S  V  S  I  I  D  T   -

GAATTAAAGGTTAAAGACTCACAGCCCATCGATTTGAGTGCATGCACTGTTGCACTTCAC
 241  ------------+---------+---------+---------+---------+---------+  300
      CTTAATTTCCAATTTCTGAGTGTCGGGTAGCTAAACTCACGTACGTGACAACGTGAAGTG a     E  L  K  V  K  D  S  Q  P  I  D  L  S  A  C  T  V  A  L  H   -

ATTTTCCAGCTGAATGAAGATGGCCCCAGCAGTGAAAATCTGGAGGAAGAGACAGAAAAC
 301  ------------+---------+---------+---------+---------+---------+  360
      TAAAAGGTCGACTTACTTCTACCGGGGTCGTCACTTTTAGACCTCCTTCTCTGTCTTTTG a     I  F  Q  L  N  E  D  G  P  S  S  E  N  L  E  E  E  T  E  N   -

ATAATTGCAGCAAATCACTGGGTTCTACCTGCAGCTGAATTCCATGGGCTTTGGGACAGC
 361  ------------+---------+---------+---------+---------+---------+  420
      TATTAACGTCGTTTAGTGACCCAAGATGGACGTCGACTTAAGGTACCCGAAACCCTGTCG a     I  I  A  A  N  H  W  V  L  P  A  A  E  F  H  G  L  W  D  S   -

TTGGTATACGATGTGGAAGTCAAATCCCATCTCCTCGATTATGTGATGACAACTTTACTG
 421  ------------+---------+---------+---------+---------+---------+  480
      AACCATATGCTACACCTTCAGTTTAGGGTAGAGGAGCTAATACACTACTGTTGAAATGAC a     L  V  Y  D  V  E  V  K  S  H  L  L  D  Y  V  M  T  T  L  L   -

TTTTCAGACAAGAACGTCAACAGCAACCTCATCACCATAGAGGGGTTCCTCCAGGCCCTG
 481  ------------+---------+---------+---------+---------+---------+  540
      AAAAGTCTGTTCTTGCAGTTGTCGTTGGAGTAGTGGTATCTCCCCAAGGAGGTCCGGGAC a     F  S  D  K  N  V  N  S  N  L  I  T  I  E  G  F  L  Q  A  L   -

TCTCTGGCAGTGGACAAGCAGTTTGAAGAGAGAAAGAAGCTT
 541  ------------+---------+---------+---------+---  582
      AGAGACCGTCACCTGTTCGTCAAACTTCTCTCTTTCTTCGAA a     S  L  A  V  D  K  Q  F  E  E  R  K  K  L   -
```

Fig. 23

(SEQ ID NO. 25)

```
      TTCACCACTGTGATGGACCTCCTCCTGGAGTATGAAGTCATCTGTATCTACTGGACCAAG
   1  ------------+---------+---------+---------+---------+---------+  60
      AAGTGGTGACACTACCTGGACGAGGACCTCATACTTCAGTAGACATAGATGACCTGGTTC a     F  T  T  V  M  D  L  L  L  E  Y  E  V  I  C  I  Y  W  T  K   -

TACTACACACTCCACAATGCAATCATTGAGGATTGTGTCAGAAAACAGCTCAAAAAAGAG
  61  ------------+---------+---------+---------+---------+---------+  120
      ATGATGTGTGAGGTGTTACGTTAGTAACTCCTAACACAGTCTTTTGTCGAGTTTTTTCTC a     Y  Y  T  L  H  N  A  I  I  E  D  C  V  R  K  Q  L  R  K  E   -

AGGCCCATCATCCTGGATCCGGCCGACCCCACCCTCAACGTGGCAGAAGGGTACAGATGG
 121  ------------+---------+---------+---------+---------+---------+  180
      TCCGGGTAGTAGGACCTAGGCCGGCTGGGGTGGGAGTTGCACCGTCTTCCCATGTCTACC a     R  P  I  I  L  D  P  A  D  P  T  L  N  V  A  E  G  Y  R  W   -

GACATCGTTGCTCAGAGGGCCTCCCAGTGCCTGAAACAGGACTGTTGCTATGACAACAGG
 181  ------------+---------+---------+---------+---------+---------+  240
      CTGTAGCAACGAGTCTCCCGGAGGGTCACGGACTTTGTCCTGACAACGATACTGTTGTCC a     D  I  V  A  Q  R  A  S  Q  C  L  K  Q  D  C  C  Y  D  N  R   -

GAGAAGGGGATCTCCAGCTGGAACGTGAAGAGGGCACGAGACATCCACTTGACAGTGGAG
 241  ------------+---------+---------+---------+---------+---------+  300
      CTCTTCCCCTAGAGGTCGACCTTGCACTTCTCCCGTGCTCTGTAGGTGAACTGTCACCTC a     Q  R  G  Y  P  D  F  N  L  I  V  N  P  Y  E  P  I  R  K  V   -

CAGAGGGGTTACCCAGATTTCAACCTCATCGTGAACCCTTATGAGCCCATAAGGAAGGTT
 301  ------------+---------+---------+---------+---------+---------+  360
      GTCTCCCCAATGGGTCTAAAGTTGGAGTAGCACTTGGGAATACTCGGGTATTCCTTCCAA a     Q  R  G  Y  P  D  F  N  L  I  V  N  P  Y  E  P  I  R  K  V   -

AAAGACAAAATCCGGAGACCAGGGGCTACTCTGGCCTGCAGCGTCTGTCCTTCCAGGTTC
 361  ------------+---------+---------+---------+---------+---------+  420
      TTTCTGTTTTAGGCCTCTGGTCCCCGATGAGACCGGACGTCGCAGACAGGAAGGTCCAAG a     K  E  I  I  R  R  P  G  A  T  L  A  C  S  V  C  P  S  R  F   -

CTGGCAGTGAGAGGCAGCTTCTCAGCAGCAGGTGCTCCTTAGCCAAATATGGGATCTTCT
 421  ------------+---------+---------+---------+---------+---------+  480
      GACCGTCACTCTCCGTCGAAGAGTCGTCGTCCACGAGGAATCGGTTTATACCCTAGAAGA a     L  A  V  R  G  S  F  S  A  A  G  A  P  *  P  N  M  G  S  S   -

CCCACAC
 481  -------  487
      GGGTGTG a     P  T   -
```

Fig. 24

(SEQ ID NO. 26)

```
      ATGGAGGATGATTTCATGTGCGATGATGAGGAGGACTACGACCTGGAATACTCTGAAGAT
  1   ---------+---------+---------+---------+---------+---------+  60
      TACCTCCTACTAAAGTACACGCTACTACTCCTCCTGATGCTGGACCTTATGAGACTTCTA a     M  E  D  D  F  M  C  D  D  E  E  D  Y  D  L  E  Y  S  E  D   -

AGTAACTCCGAGCCAAATGTGGATTTGGAAAATCAGTACTATAATTCCAAAGCATTAAAA
 61   ---------+---------+---------+---------+---------+---------+ 120
      TCATTGAGGCTCGGTTTACACCTAAACCTTTTAGTCATGATATTAAGGTTTCGTAATTTT a     S  N  S  E  P  N  V  D  L  E  N  Q  Y  Y  N  S  K  A  L  K   -

GAAGATGACCCAAAAGCGGCATTAAGCAGTTTCCAAAAGGTTTTGGAACTTGAAGGTGAA
121   ---------+---------+---------+---------+---------+---------+ 180
      CTTCTACTGGGTTTTCGCCGTAATTCGTCAAAGGTTTTCCAAAACCTTGAACTTCCACTT a     E  D  D  P  K  A  A  L  S  S  F  Q  K  V  L  E  L  E  G  E   -

AAAGGAGAATGGGGATTTAAAGCACTGAAACAAATGATTAAGATTAACTTCAAGTTGACA
181   ---------+---------+---------+---------+---------+---------+ 240
      TTTCCTCTTACCCCTAAATTTCGTGACTTTGTTTACTAATTCTAATTGAAGTTCAACTGT a     K  G  E  W  G  F  K  A  L  K  Q  M  I  K  I  N  F  K  L  T   -

AACTTTCCAGAAATGATGAATAGATATAAGCAGCTATTGACCTATATTCGGAGTGCAGTC
241   ---------+---------+---------+---------+---------+---------+ 300
      TTGAAAGGTCTTTACTACTTATCTATATTCGTCGATAACTGGATATAAGCCTCACGTCAG a     N  F  P  E  M  M  N  R  Y  K  Q  L  L  T  Y  I  R  S  A  V   -

ACAAGAAATTATTCTGAAAAATCCATTAATTCTATTCTTGATTATATCTCTACTTCTAAA
301   ---------+---------+---------+---------+---------+---------+ 360
      TGTTCTTTAATAAGACTTTTTAGGTAATTAAGATAAGAACTAATATAGAGATGAAGATTT a     T  R  N  Y  S  E  K  S  I  N  S  I  L  D  Y  I  S  T  S  K   -

CAGATGGATTTACTGCAGGAATTCTATGAAACAACACTGGAAGCTTTGAAAGATGCTAAG
361   ---------+---------+---------+---------+---------+---------+ 420
      GSCSACCSAAATGACG?CCSSAAGASACSSSGSSGTGACCrTCGAAACSSSCTAC5ASTC a     Q  M  D  L  L  Q  E  F  Y  E  T  T  L  E  A  L  K  D  A  K   -

AATGATAGACTGTGGTTTAAGACAAACACAAAGCTTGGAAAATTATATTTAGAACGAGAG
421   ---------+---------+---------+---------+---------+---------+ 480
      TTACTATCTGACACCAAATTCTGTTTGTGTTTCGAACCTTTTAATATAAATCTTGCTCTC a     N  D  R  L  W  F  K  T  N  T  K  L  G  K  L  Y  L  E  R  E   -

GAATATGGAAAGCTTCAAAAAATTTTACGCCAGTTACATCAGTCGTGCCAGACTGATGAT
481   ---------+---------+---------+---------+---------+---------+ 540
      CTTATACCTTTCGAAGTTTTTTAAAATGCGGTCAATGTAGTCAGCACGGTCTGACTACTA a     E  Y  G  K  L  Q  K  I  L  R  Q  L  H  Q  S  C  Q  T  D  D   -

GGAGAAGATGATCTGAAAAAAGGTACACAGTTATTAGAAATATATGCTTTGGAAATTCAA
541   ---------+---------+---------+---------+---------+---------+ 600
      CCTCTTCTACTAGACTTTTTTCCATGTGTCAATAATCTTTATATACGAAACCTTTAAGTT
```

Fig. 25A

```
a       G  E  D  D  L  K  K  G  T  Q  L  L  E  I  Y  A  L  E  I  Q   -
        ATGTACACAGCACAGAAAAATAACAAAAAACTTAAAGCACTCTATGAACAGTCACTTCAC
   601  ---------+---------+---------+---------+---------+---------+ 660
        TACATGTGTCGTGTCTTTTTATTGTTTTTTGAATTTCGTGAGATACTTGTCAGTGAAGTG a       M  Y  T  A  Q  K  N  N  K  K  L  K  A  L  Y  E  Q  S  L  H   -
        ATCAAGTCTGCCATCCCTCATCCACTGATTATGGGAGTTATCAGAGAATGTGGTGGTAAA
   661  ---------+---------+---------+---------+---------+---------+ 720
        TAGTTCAGACGGTAGGGAGTAGGTGACTAATACCCTCAATAGTCTCTTACACCACCATTT a       I  K  S  A  I  P  H  P  L  I  M  G  V  I  R  E  C  G  G  K   -
        ATTGCACTTGGGGGAGGTGAATTTGAAAAGGCACACACTGATTTTTTT
   721  ---------+---------+---------+---------+-------- 768
        TAACGTGAACCCCCTCCACTTAAACTTTTCCGTGTGTGACTAAAAAAA a       I  A  L  G  G  G  E  F  E  K  A  H  T  D  F  F   -
```

Fig. 25B (SEQ ID NO. 27)

```
    1 GCAGAGGTTAAAACACCTTTTGATTTGGCCAAGGCACAAGAGAACAGCAACTCCGTAAAG
      ---------+---------+---------+---------+---------+---------+  60
      CGTCTCCAATTTTGTGGAAAACTAAACCGGTTCCGTGTTCTCTTGTCGTTGAGGCATTTC a       A  E  V  K  T  P  F  D  L  A  K  A  Q  E  N  S  N  S  V  K   -

61 AAGAAGACAAAGTTTGTCAATTTATACACAAGAGAAAGACAGGACAGGCTTGCAGTCCTG
      ---------+---------+---------+---------+---------+---------+ 120
      TTCTTCTGTTTCAAACAGTTAAATATGTGTTCTCTTTCTGTCCTGTCCGAACGTCAGGAC a       K  K  T  K  F  V  N  L  Y  T  R  E  R  Q  D  R  L  A  V  L   -

121 CTCCCTGGTCGTCACCCTTGTGATTGCCTGGGCCAGAAGCACAAGCTCATCAATAACTGT
      ---------+---------+---------+---------+---------+---------+ 180
      GAGGGACCAGCAGTGGGAACACTAACGGACCCGGTCTTCGTGTTCGAGTAGTTATTGACA a       L  P  G  R  H  P  C  D  C  L  G  Q  K  H  K  L  I  N  N  C   -

181 CTGATCTGTGGGCGCATTGTCTGTGAACAAGAAGGCTCAGGCCCTTGCTTATTCTGTGGC
      ---------+---------+---------+---------+---------+---------+ 240
      GACTAGACACCCGCGTAACAGACACTTGTTCTTCCGAGTCCGGGAACGAATAAGACACCG a       L  I  C  G  R  I  V  C  E  Q  E  G  S  G  P  C  L  F  C  G   -

241 ACTCTGGTGTGTACTCATGAGGAACAAGATATTTTACAGCGTGACTCAAACAAGAGCCAG
      ---------+---------+---------+---------+---------+---------+ 300
      TGAGACCACACATGAGTACSCCSSGSSCSATAkAASGSCGCACTSAGSSSGTTCTCGGSC a       T  L  V  C  T  H  E  E  Q  D  I  L  Q  R  D  S  N  K  S  Q   -

301 AAACTGCTAAAGAAACTCATGTCAGGAGTGGAGAATTCTGGAAAGGTGGACATCTCTACC
      ---------+---------+---------+---------+---------+---------+ 360
      TTTGACGATTTCTTTGAGTACAGTCCTCACCTCTTAAGACCTTTCCACCTGTAGAGATGG a       K  L  L  K  K  L  M  S  G  V  E  N  S  G  K  V  D  I  S  T   -

361 AAGGACCTTCTTCCTCATCAAGAATTGCGAATTAAGTCTGGTCTGGAGAAGGCTATCAAG
      ---------+---------+---------+---------+---------+---------+ 420
      TTCCTGGAAGAAGGAGTAGTTCTTAACGCTTAATTCAGACCAGACCTCTTCCGATAGTTC a       K  D  L  L  P  H  Q  E  L  R  I  K  S  G  L  E  K  A  I  K   -

421 CATAAAGACAAACTGTTAGAGTTTGACAGAACTAGTATTCGAAGGACCCAAGTCATTGAT
      ---------+---------+---------+---------+---------+---------+ 480
      GTATTTCTGTTTGACAATCTCAAACTGTCTTGATCATAAGCTTCCTGGGTTCAGTAACTA a       H  K  D  K  L  L  E  F  D  R  T  S  I  R  R  T  Q  V  I  D   -

481 GATGAGTCAGATTACTTTGCCAGTGATTCTAACCAATGGTTGTCCAAACTTGAGCGGGAA
      ---------+---------+---------+---------+---------+---------+ 540
      CTACTCAGTCTAATGAAACGGTCACTAAGATTGGTTACCAACAGGTTTGAACTCGCCCTT a       D  E  S  D  Y  F  A  S  D  S  N  Q  W  L  S  K  L  E  R  E   -

541 ACCTTGCAGAAGCGAGAGGAGGAGCTGAGAGAACTTCGACACGCCTCTCGACTTTCTAAG
      ---------+---------+---------+---------+---------+---------+ 600
      TGGAACGTCTTCGCTCTCCTCCTCGACTCTCTTGAAGCTGTGCGGAGAGCTGAAAGATTC
```

AAGGTCACCATTGACTTTGCAGGAAGGAAGATCCTGGAAGAAGAAAATTCACTAGCAGAG
601   ------------+---------+---------+---------+---------+--------+  660
      TTCCAGTGGTAACTGAAACGTCCTTCCTTCTAGGACCTTCTTCTTTTAAGTGATCGTCTC a     K  V  T  I  D  F  A  G  R  K  I  L  E  E  E  N  S  L  A  E    -

TATCATAGCAGACTAGATGAGACAATACAGGCCATTGCCAATGGAACCTTGAACCAGCCA
661   ---------+---------+---------+---------+---------+---------+  720
      ATAGTATCGTCTGATCTACTCTGTTATGTCCGGTAACGGTTACCTTGGAACTTGGTCGGT a     Y  H  S  R  L  D  E  T  I  Q  A  I  A  N  G  T  L  N  Q  P    -

CTGACCAAATTGGATAGATCTTCTGAAGAGCCTTTGGGAGTTCTGGTAAATCCCAACATG
721   ---------+---------+---------+---------+---------+---------+  780
      GACTGGTTTAACCTATCTAGAAGACTTCTCGGAAACCCTCAAGACCATTTAGGGTTGTAC a     L  T  K  L  D  R  S  S  E  E  P  L  G  V  L  V  N  P  N  M    -

TACCAGTCCCCTCCCCAGTGGTTGACCACACAGGTGCAGCCTCACAGAAGAAGGCTTTCC
781   ---------+---------+---------+---------+---------+---------+  840
      ATGGTCAGGGGAGGGGTCACCAACTGGTGTGTCCACGTCGGAGTGTCTTCTTCCGAAAGG a     Y  Q  S  P  P  Q  W  L  T  T  Q  V  Q  P  H  R  R  R  L  S    -

GTTCTTCAGGATTTGGACTAGAGTTCAACTCATTTCAGCACCAGTTGCGAATCCAGGATC
841   ---------+---------+---------+---------+---------+---------+  900
      CAAGAAGTCCTAAACCTGATCTCAAGTTGAGTAAAGTCGTGGTCAACGCTTAGGTCCTAG a     V  L  Q  D  L  D  *  S  S  T  H  F  S  T  S  C  E  S  R  I    -

AAGAATTTCAGGAAGGCTTTGATGGTGGCTGGTGCCTCTCTGTACATCAGCCCTGGGTTC
901   ---------+---------+---------+---------+---------+---------+  960
      TTCTTAAAGTCCTTCCGAAACTACCACCGACCACGGAGAGACATGTAGTCGGGACCCAAG a     K  N  F  R  K  A  L  M  V  A  G  A  S  L  Y  I  S  P  G  F    -

TCTGCTTGTCAGAGGGATTAAAAGGGTGGAGGGCAGATCCTGGTACACCCCCCACAGAGG
961   ---------+---------+---------+---------+---------+---------+  1020
      AGACGAACAGTCTCCCTAATTTTCCCACCTCCCGTCTAGGACCATGTGGGGGTGTCTCC a     S  A  C  Q  R  D  *  K  G  G  G  Q  I  L  V  H  P  P  Q  R    -

ACGACTTTGGATAGCAGCCACAGCTAAAAAATCCCTCCCCTCAAGAAGTCTCAGAACTCC
1021  ---------+---------+---------+---------+---------+---------+  1080
      TGCTGAAACCTATCGTCGGTGTCGATTTTTTAGGGAGGGGAGTTCTTCAGAGTCTTGAGG a     T  T  L  D  S  S  H  S  *  K  I  P  P  L  K  K  S  Q  N  S    -

AGGCTACATATCGTCTTCTTCGTTGGGAAGATGTGGAATTT
1081  ---------+---------+---------+--------+-  1121
      TCCGATGTATAGCAGAAGAAGCAACCCTTCTACACCTTAAA a     R  L  H  I  V  F  F  V  G  K  M  W  N            -
```

Fig. 26B (SEQ ID NO. 28)

```
        GAAAGGGCCCTGACAGCACACACACTTAAACACAGTTTTCTGATAACTTTGGAATTCACA
     1  ---------+---------+---------+---------+---------+---------+ 60
        CTTTCCCGGGACTGTCGTGTGTGTGAATTTGTGTCAAAAGACTATTGAAACCTTAAGTGT a        E  R  A  L  T  A  H  T  L  K  H  S  F  L  I  T  L  E  F  T   -

CCGTTGGACTAGTTAAAAACTTCTAAAATAATTTTTTAAAATCTAATA
    61  ---------+---------+---------+---------+-------- 108
        GGCAACCTGATCAATTTTTGAAGATTTTATTAAAAAATTTTAGATTAT a        P  L  D  *  L  K  T  S  K  I  I  F  *  N  L  I   -
```

Fig. 27

(SEQ ID NO. 29)

```
      CCAGGAACTGAGATCTTTAATCTGCCAGCAGTTACTACGTCAGGCTCAGTTAGCTCTAGA
    1 ---------+---------+---------+---------+---------+---------+ 60
      GGTCCTTGACTCTAGAAATTAGACGGTCGTCAATGATGCAGTCCGAGTCAATCGAGATCT a     P  G  T  E  I  F  N  L  P  A  V  T  T  S  G  S  V  S  S  R   -

GGCCATTCTTTTGCTGATCCTGCCAGTAATCTTGGGCTGGAAGACATTATCAGGAAGGCT
   61 ---------+---------+---------+---------+---------+---------+ 120
      CCGGTAAGAAAACGACTAGGACGGTCATTAGAACCCGACCTTCTGTAATAGTCCTTCCGA a     G  H  S  F  A  D  P  A  S  N  L  G  L  E  D  I  I  R  K  A   -

CTCATGGGAAGCTTTGATGACAAAGTTGAGGATCATGGAGTTGTCATGTCCCAGCCTATG
  121 ---------+---------+---------+---------+---------+---------+ 180
      GAGTACCCTTCGAAACTACTGTTTCAACTCCTAGTACCTCAACAGTACAGGGTCGGATAC a     L  M  G  S  F  D  D  K  V  E  D  H  G  V  V  M  S  Q  P  M   -

GGAGTAGTGCCTGGTACTGCCAACACCTCAGTTGTGACC
  181 ---------+---------+---------+--------- 219
      CCTCATCACGGACCATGACGGTTGTGGAGTCAACACTGG a     G  V  V  P  G  T  A  N  T  S  V  V  T   -
```

Fig. 28

(SEQ ID NO. 30)

H  B  Pl  Lu  Li  SM  K  Pa
JL1 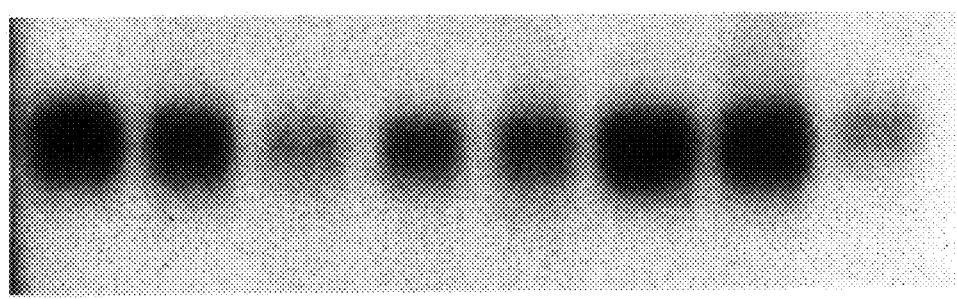
JL2 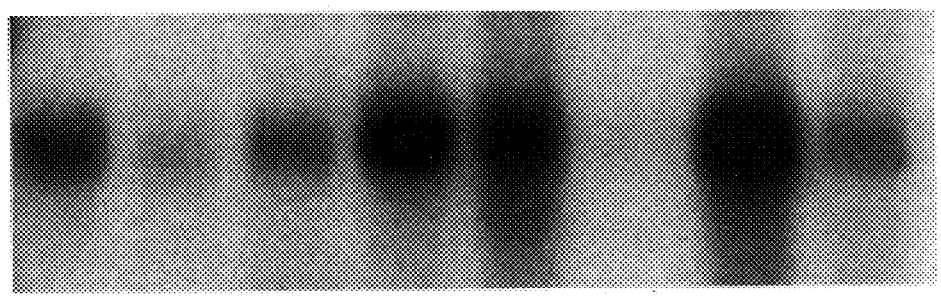
Fig. 29

```
351a    26 LQLEAENYEGHTPLHVAVIHKDVEMVRLLRDAGADLDKPEPTCGRSPFIW 75
           | ||| || | | |||||   | | ||   ||| |      ||||| |
BCL3   225 LDLEARNYDGLTALHVAVNTECQETVQLLLERGADIDVDIKSGRSPLIH 274

351a    76 QWRPGS.RCAGASLRAGANPAARMYGGRTPLGSAMLRPNPILARLLR 121
           |      |    ||| |||| |  |  ||| |    | |    ||
BCL3   275 AVENNSLSMVQLLLQHGANVNAQMSGSSALHSASGRGLLPLVRTLV 321

351a   122 AHGAPEPEGKDEKSGP 137
              ||           |
BCL3   322 RSGADSSLKNCHNDTP 337
```

Fig. 30

NUCLEAR THYROID HORMONE RECEPTOR-INTERACTING POLYNUCLEOTIDES AND RELATED MOLECULES AND METHODS

This is a divisional of copending application Ser. No. 08/222,719, filed Apr. 4, 1994, which is a continuation-in-part of application Ser. No. 07/969,136 filed on Oct. 30, 1992 now abandoned.

BACKGROUND OF THE INVENTION

This invention relates to receptor proteins.

The diverse physiological and developmental effects of thyroid hormone receptor (for example, T3) are mediated by the three hormone-binding isoforms of the T3 receptor: TRα1, TRβ1, and TRβ2. The effects of the hormone are the consequences of changes in expression of a wide range of target genes that result from T3 binding to these receptors. While it is unknown how binding of the ligand to the receptor actually causes such changes in gene expression, the basic effects on the rate of transcription are believed to be a consequence of direct or indirect protein-protein contacts between the TRs and components of basic transcriptional apparatus, such as RNA polymerase or associated proteins. In addition, interactions of TRs with other transcription factors are thought to result in a variety of complex combinatorial regulatory effects.

In recent years there has been very rapid progress in unravelling the most basic aspects of the mechanism of T3 action in the control of gene expression (see Brent et al., Ann. Rev. Physiol. 53:17–35, 1991 for recent review). It is now clear that the T3 receptors are transcription factors that belong to a related superfamily of nuclear hormone receptors. This family of proteins interacts not only with diverse ligands but also with a complex array of similar DNA binding sites. Like other DNA binding transcription factors, the TRs function by increasing (or, in some cases, decreasing) the rate of transcription initiation from a linked promoter.

Other details of the mechanisms that cause such alterations remain unclear and are the focus of intense study in a number of systems (see Lewin, Cell 61:1161–1164, 1990; Ptashne, Sci. Am. 260:40–47, 1989; Ptashne, and Gann, Nature 346:329–331, 1990, for reviews). However, two broad themes are evident. The first is that transcription factors in general are frequently modular, composed of distinct domains with separate DNA binding and transcriptional regulatory functions. With TRs, for example, it is apparent that the DNA binding and ligand binding domains are quite separate, and experiments with chimeric receptors make it clear that the T3 dependent activation of gene expression can be transferred to heterologous DNA binding domains (see, e.g., Holloway, Proc. Natl. Acad. Sci. USA 87:8160–8164, 1990; Thompson and Evans, Proc. Natl. Acad. Sci. USA 86:3494–3498, 1989).

A second theme is that the functions of transcription factors are believed to be a consequence of protein-protein interactions with the basic transcriptional apparatus. It is thought that these interactions are mediated by proteins called coactivators or adaptors (see Ptashne and Gann, Nature 346:329–331, 1990). These poorly characterized proteins act as bridges between the transcriptional activation domain that is tethered to the DNA by the transcription factor and the RNA polymerase complex bound at the initiation site. Via unknown mechanisms, this interaction leads to an increase in promoter activity.

Protein-protein contacts are also essential for a surprisingly diverse array of positive and negative interactions between transcription factors. Recent results in several systems indicate that this mechanism leads to complex regulatory networks that allow cross talk between various signalling pathways. In the case of TRs, three such interactions have been described to date. The first is the heterodimeric interaction of TRs with the related RXRs (Bugge et al., EMBO J 11:1409–1418, 1992; Kliewer et al., Nature 355:446–449, 1992; Lied et al., Cell 68:377–395, 1992; Marks et al., EMBO J 11:1419–1435, 1992; Yu et al., Cell 67:1251–1266, 1991; Zhang et al., Nature 355:441–446, 1992). TR/RXR heterodimers show higher DNA binding affinity to thyroid hormone response elements (i.e., T3RE sites) initially characterized as binding TR homodimers (see, e.g., Williams et al., J. Biol. Chem. 266:19636–19644, 1991), but heterodimerization does not appear to alter site specificity.

A second, less direct interaction is reflected in the mutually antagonistic effects of the TRs and the c-jun and c-fos protooncogenes (Desbois et al., Cell 67:731–740, 1991; Zhang et al., Mol. Cell. Biol. 11:6016–6025, 1991). The heterodimeric complex of these two leucine zipper transcription factors is frequently referred to as AP-1, although the jun-jun homodimers and other complexes containing related but less well characterized proteins can also bind the consensus AP-1 site. Such sites are also referred to as TPA response elements (i.e., TREs) (here distinguished from T3REs) because the induction of protein kinase C activity by TPA or other phorbol esters results in a very rapid induction of AP-1 activity (reviewed in (Curran and Franza, Cell 55:395–397, 1988). The activity of the TRs is antagonized by coexpression of active jun or fos, and the TRs exert a complimentary inhibition of jun and fos activity. Although the mechanism of this interaction is unknown, it does not require the presence of overlapping DNA binding sites. Thus, TRs can antagonize TPA response on a promoter that does not contain a T3RE, and jun and fos can antagonize T3 response on a promoter that does not include a TRE. Interestingly, although TRs are always nuclear and are able to bind T3REs whether or not hormone is present, the antagonistic function is only observed when T3 is present.

The antagonistic interaction with jun and fos is also observed with other members of the superfamily, including RARs (Desbois et al., Cell 67:731–740, 1991; Schule et al., Proc. Natl. Acad. Sci. USA 88:6092–6096, 1991) and GRs (Jonat et al., Cell 62:1189–1204; Schule et al., Cell 62:1217–1226, 1990; Yang-Yen et al., Cell 62:1205–1215, 1990). The GR interaction was the first described and has been the best characterized, but the biochemical basis for the effect remains uncertain (see Ponta et al., Acta 1129:255–261, 1992 for a review). Despite the potential importance of this apparent cross-talk between nuclear hormone receptors and the protein kinase C signalling pathway, its physiologic impact also remains unclear.

Finally, TRs have also been reported to interact both functionally and biochemically with the cell-type specific transcriptional activator Pit-1 (Schaufele et al., Mol. Endocrinol. 6:656–665, 1992). In contrast to the antagonistic effects of TRs and AP-1, this interaction apparently leads to synergistic activation.

These distinct mechanisms for the modulation of transcriptional activation remain quite unclear. It is apparent that the identification and characterization of proteins capable of interacting specifically with the TRs could provide important clues to these processes and other potential functions of the receptors, such as regulation of cell proliferation (Halperin et al., Endocrinology 126:2321–2326, 1990). In addition, interacting proteins provide a means of controlling and modulating thyroid hormone receptor function.

SUMMARY OF THE INVENTION

In a first aspect, the invention generally features a method for determining whether a test protein is capable of interacting with a nuclear hormone receptor protein. The method involves: (a) providing a host cell which contains (i) a reporter gene operably linked to a protein binding site; (ii) a first fusion gene which expresses a first fusion protein, the first fusion protein including a nuclear hormone receptor protein covalently bonded to a binding moiety which is capable of specifically binding to the protein binding site; and (iii) a second fusion gene which expresses a second fusion protein, the second fusion protein including the test protein covalently bonded to a weak gene activating moiety; and (b) determining whether the test protein increases expression of the reporter gene as an indication of its ability to interact with the nuclear hormone receptor protein.

In a preferred embodiment, the method further involves treating the host cell with a ligand which binds the nuclear hormone receptor and identifying a hormone-dependent interacting protein by its ability to increase expression of the reporter gene only upon treatment of the cell by the ligand. In another preferred embodiment, the method further involves treating the host cell with a ligand which binds the nuclear hormone receptor and identifying a hormone-independent interacting protein by its ability to increase expression of the reporter gene both in the presence and in the absence of ligand treatment. In yet another preferred embodiment, the method further involves treating the host cell with a ligand which binds the nuclear hormone receptor and identifying a ligand-sensitive interacting protein by its ability to increase expression of the reporter gene in the absence but not in the presence of the ligand treatment. Preferably, the ligand is a thyroid hormone.

In other preferred embodiments, the weak gene activating moiety is the gene activating moiety of B42 or a gene activating moiety of lesser activation potential; and the nuclear hormone receptor is a thyroid hormone receptor.

In a second aspect, the invention features a substantially pure preparation of a thyroid hormone receptor (TR)-interacting protein. Preferably, the TR-interacting protein is JL1 or JL2; includes an amino acid sequence substantially identical to an amino acid sequence shown in any of FIGS. 2–28 (SEQ ID NOS: 1, 3, 6–30); and is derived from a mammal, for example, a human.

In a related aspect, the invention features purified DNA (for example, cDNA) which includes a sequence encoding a TR-interacting protein, preferably encoding a human TR-interacting protein, for example, the TR-interacting proteins JL1 or JL2.

In other related aspects, the invention features a vector and a cell which includes a purified DNA of the invention; a purified antibody which specifically binds a TR-interacting protein of the invention; and a method of producing a recombinant TR-interacting protein involving providing a cell transformed with DNA encoding a TR-interacting protein positioned for expression in the cell; culturing the transformed cell under conditions for expressing the DNA; and isolating the recombinant TR-interacting protein. The invention further features recombinant TR-interacting protein produced by such expression of a purified DNA of the invention.

In yet another aspect, the invention features a therapeutic composition which includes as an active ingredient a TR-interacting protein of the invention, the active ingredient being formulated in a physiologically-acceptable carrier. Such therapeutic compositions are useful in a method of treating thyroid disorders in a mammal, involving administering the therapeutic composition to the mammal in a dosage effective to increase thyroid function (in the case of hypothyroidism) or decrease thyroid function (in the case of hyperthyroidism).

As used herein, "reporter gene" is meant a gene whose expression may be assayed; such genes include, without limitation, lacZ, amino acid biosynthetic genes, e.g. the yeast LEU2 gene, or the mammalian chloramphenicol transacetylase (CAT) gene. Reporter genes may be integrated into the chromosome or may be carried on autonomously replicating plasmids (e.g., yeast 2μ plasmids).

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By a "binding moiety" is meant a stretch of amino acids which is capable of directing specific polypeptide binding to a particular DNA sequence (i.e., a "protein binding site"). LexA represents a preferred DNA binding moiety in the invention. However, any other transcriptionally-inert or essentially transcriptionally-inert DNA binding domain may be substituted. The GAL4 DNA binding domain represents a somewhat less preferred DNA binding moiety for the system described herein.

By "weak gene activating moiety" is meant a stretch of amino acids which is capable of weakly inducing the expression of a gene to whose control region it is bound. As used herein, "weakly" is meant below the level of activation effected by GAL4 activation region II (Ma and Ptashne, Cell 48:847, 1987) and is preferably at or below the level of activation effected by the B42 activation domain of Ma and Ptashne (Cell 51:113, 1987). Levels of activation may be measured using any downstream reporter gene system and comparing, in parallel assays, the level of expression stimulated by the GAL4- or B42-polypeptide with the level of expression stimulated by the polypeptide to be tested.

By "TR-interacting protein" is meant a polypeptide which directly or indirectly physically interacts with a thyroid hormone receptor in the in vivo protein interaction assay described herein. Such an interaction may be thyroid hormone dependent or independent or may be thyroid hormone sensitive; it may also be transient in nature. Preferably, such a polypeptide has an amino acid sequence which is at least 80%, preferably 90%, and most preferably 95% or even 99% homologous to the amino acid sequence of an interacting protein described herein (e.g., JL1 or JL2) at the point of interaction with the thyroid hormone receptor, or at least 80% and preferably 90% homologous overall. A "TR-interacting protein", as used herein, does not include any of the RXR proteins or Pit-1.

By "thyroid hormone" is meant T3, triac, or T4, and less preferably reverse T3.

By "substantially pure" is meant a preparation which is at least 60% by weight (dry weight) the compound of interest, i.e., a TR-interacting protein. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 80%, more preferably 90%, and most preferably 95% homologous to one of the sequences of FIGS. 2–28 (SEQ ID NOS: 1, 3, 6–30). A "substantially identical" nucleic acid sequence codes for a substantially identical amino acid sequence as defined above.

By "transformed cell" is meant a cell into which (or into an ancestor of which) has been introduced, by means of recombinant DNA techniques, a DNA molecule encoding (as used herein) a TR-interacting protein.

By "positioned for expression" is meant that the DNA molecule is positioned adjacent to a DNA sequence which directs transcription and translation of the sequence (i.e., facilitates the production of, e.g., a TR-interacting protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., TR-interacting protein-specific antibody. A purified TR-interacting protein antibody may be obtained, for example, by affinity chromatography using recombinantly-produced TR-interacting protein and standard techniques.

By "specifically binds" is meant an antibody which recognizes and binds TR-interacting protein but which does not substantially recognize and bind other molecules in a sample, e.g., a biological sample, which naturally includes TR-interacting protein.

Other features and advantages of the invention will be apparent from the following detailed description thereof, and from the claims.

BRIEF DESCRIPTION OF THE DRAWINGS

The drawings are first briefly described.

FIG. 1A shows that in cells expressing a fusion protein consisting of the B42 transactivation (TA) domain fused to a protein that does not interact specifically with the lexA/TR chimera, the LEU2 gene is not expressed, and the cells require supplemental leucine for growth. FIG. 1B shows that in cells expressing a TA fusion to a protein capable of binding the lexA/TR chimera, the TA domain is brought specifically to the promoter LEU2 expression is increased, and the cells do not require supplemental leucine.

FIG. 2 shows the complete amino acid sequence of JL1 (SEQ ID NO:1), aligned with the recently identified S. cerevisiae transcriptional coactivator SUG1 (Swaffield et al., Nature 357:698–700, 1992) (SEQ ID NO:2). Identities and conservative substitutions are indicated. The overall sequence identity is 73%. The boxed and bold residues from 190 to 197 (JL1) represent a potential ATP binding site that is conserved in all members of this family. The boxed residues from 45 to 66 (JL1) are a putative leucine zipper, extended by 1 heptad toward the N-terminus in this full length sequence, which appears to be unique to JL1 and SUG1. The N-terminal portion of the JL1 sequence (1–49) was derived from subcloned PCR products corresponding to the 5' end of the JL1 mRNA. Independent clones with identical sequence were isolated using internal JL1 and vector primers with a HeLa cell cDNA library as template. The methionine residue assigned as the start codon is preceded by a stop codon only 9 nucleotides upstream.

FIG. 3 shows the amino acid sequence of JL2 (SEQ ID NO:3); the two LIM domains are underlined and the consensus C/D and H residues are bold. This sequence represents the human portion of the fusion protein isolated as an activator of the lexA/TRβ chimera. FIG. 3B shows the alignment of the LIM domains of JL2(SEQ ID NO:4) with those of Lin11 (SEQ ID NO:5). These domains in both proteins include matches to all consensus positions; the overall sequence identity is 35%.

FIG. 4 (SEQ ID NO:6) shows a partial nucleic acid sequence and deduced amino acid sequence of the TR-interacting protein S112a-.

FIG. 5 (SEQ ID NO:7) shows a partial nucleic acid sequence and deduced amino acid sequence of the TR-interacting protein S103a.

FIG. 6 (SEQ ID NO:8) shows a partial nucleic acid sequence and deduced amino acid sequence of the TR-interacting protein S203a.

FIG. 7 (SEQ ID NO:9) shows a partial nucleic acid sequence and deduced amino acid sequence of the TR-interacting protein S204b.

FIG. 8 (SEQ ID NO:10) shows a partial nucleic acid sequence and deduced amino acid sequence of the TR-interacting protein S205a.

FIG. 9 (SEQ ID NO:11) shows a partial nucleic acid sequence and deduced amino acid sequence of the TR-interacting protein S249a.

FIG. 10 (SEQ ID NO:12) shows a partial nucleic acid sequence and deduced amino acid sequence of the TR-interacting protein S351a.

FIG. 11 (SEQ ID NO:13) shows a partial nucleic acid sequence and deduced amino acid sequence of the TR-interacting protein S101a.

FIG. 12 (SEQ ID NO:14) shows a partial nucleic acid sequence and deduced amino acid sequence of the TR-interacting protein S223a.

FIG. 13 (SEQ ID NO:15) shows a partial nucleic acid sequence and deduced amino acid sequence of the TR-interacting protein S239a.

FIG. 14 (SEQ ID NO:16) shows a partial nucleic acid sequence and deduced amino acid sequence of the TR-interacting protein S410a.

FIG. 15 (SEQ ID NO:17) shows a partial nucleic acid sequence and deduced amino acid sequence of the TR-interacting protein S418a.

FIG. 16 (SEQ ID NO:18) shows a partial nucleic acid sequence and deduced amino acid sequence of the TR-interacting protein S419a.

FIG. 17 (SEQ ID NO:19) shows a partial nucleic acid sequence and deduced amino acid sequence of the TR-interacting protein S107a-.

FIG. 18 (SEQ ID NO:20) shows a partial nucleic acid sequence and deduced amino acid sequence of the TR-interacting protein S213a-.

FIG. 19 (SEQ ID NO:21) shows a partial nucleic acid sequence and deduced amino acid sequence of the TR-interacting protein S113a-.

FIG. 20 (SEQ ID NO:22) shows a partial nucleic acid sequence and deduced amino acid sequence of the TR-interacting protein S116a-.

FIG. 21 (SEQ ID NO:23) shows a partial nucleic acid sequence and deduced amino acid sequence of the TR-interacting protein S309a-.

FIG. 22 (SEQ ID NO:24) shows a partial nucleic acid sequence and deduced amino acid sequence of the TR-interacting protein S227b-.

FIG. 23 (SEQ ID NO:25) shows a partial nucleic acid sequence and deduced amino acid sequence of the TR-interacting protein S215a-.

FIG. 24 (SEQ ID NO:26) shows a partial nucleic acid sequence and deduced amino acid sequence of the TR-interacting protein S223a-.

FIG. 25 (SEQ ID NO:27) shows a partial nucleic acid sequence and deduced amino acid sequence of the TR-interacting protein S240a-.

FIG. 26 (SEQ ID NO:28) shows a partial nucleic acid sequence and deduced amino acid sequence of the TR-interacting protein S139a.

FIG. 27 (SEQ ID NO:29) shows a partial nucleic acid sequence and deduced amino acid sequence of the TR-interacting protein S110a-.

FIG. 28 (SEQ ID NO:30) shows a partial nucleic acid sequence and deduced amino acid sequence of the TR-interacting protein S243b.

FIG. 29 shows a Northern analysis of JL1 and JL2 expression in various human tissues. Specifically, 2 μg of poly A$^+$ mRNA from the indicated tissues (H, heart; B, brain; Pl, placenta; Lu, lung; Li, liver; SM, skeletal muscle; K, kidney; Pa, pancreas; all obtained from Clontech, Palo Alto, Calif.) was hybridized to JL1 and JL2 probes by standard techniques and washed at high stringency (see Ausubel et al., infra). Equivalent loading of RNA was verified by hybridization with a human actin cDNA probe.

FIG. 30 shows the amino acid comparison of polypeptide 351a SEQ ID NO:12 and a portion of BCL3 SEQ ID NO:31. Identical amino acids are indicated, and approximate positions of ankyrin repeats are underlined in BCL3. The first ankyrin repeat of BCL3 in the comparison corresponds to the 4th of 7 total in the full-length sequence.

There now follows a description of the use of an in vivo interaction trap system for the isolation of proteins which physically associate with thyroid hormone receptor and a description of exemplary interacting proteins (termed, TR-interacting proteins). This system may be used generally to isolate proteins which interact with any nuclear hormone receptor. Because the system has such general application for the isolation of nuclear hormone receptor-interacting proteins, this example is designed to illustrate, not limit, the invention.

DETAILED DESCRIPTION

Applicants have used an in vivo interaction trap system (developed in the laboratory of Dr. Roger Brent) to identify and isolate proteins that physically interact with nuclear hormone receptors and, in particular, with the ligand binding domain of the rat receptor TRβ. This system, based on the modular nature of transcription factors, allows direct genetic selection for proteins capable of interacting with a desired protein.

Figure 1A:
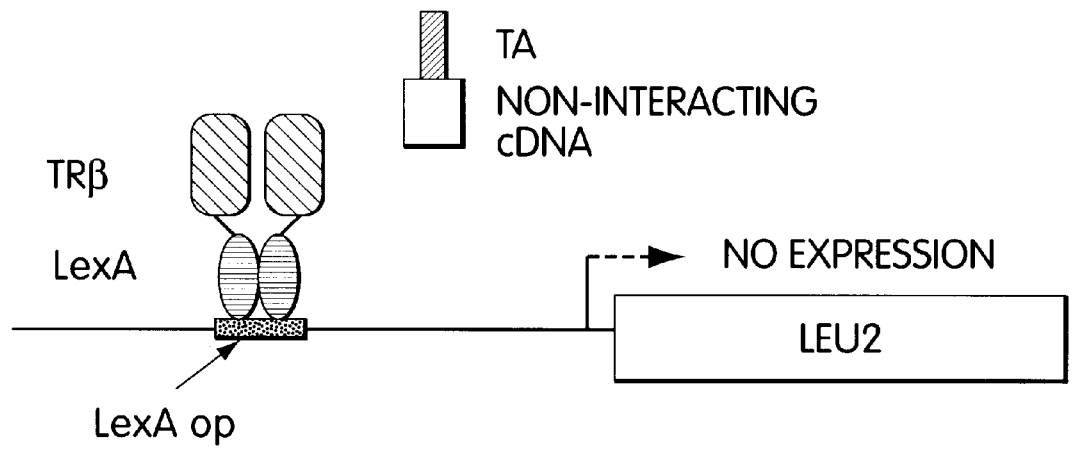
FIGS. 1A and 1B show a genetic selection in yeast for the isolation of TR-interacting protein-encoding cDNAs. The LexA/TRβ chimeras bind to the lexA binding site (lexA op) upstream of the LEU2 gene.
Figure 1B:
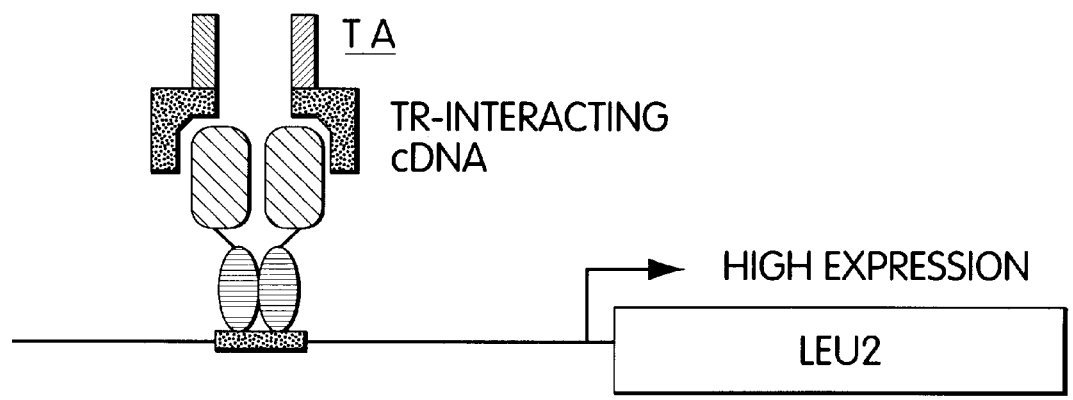

In general, DNA encoding the desired protein is fused to DNA encoding the C-terminus of a DNA binding domain, for example, the DNA binding domain of the bacterial repressor LexA protein, to generate a chimeric transcription factor, which can be tested for function in yeast. In the instant case, a lexA/TR chimera consisting of intact lexA fused to the hinge, ligand binding, and C terminal (D, E and F) domains of TRβ was found to be completely unable to activate transcription in either the presence or absence of T3 ligand. This lack of transcriptional activation by the lexA/TR chimera provided the basis for applicants' genetic selection. As shown in FIG. 1, a yeast strain in which expression of the LEU2 gene is dependent on binding of an activator to upstream lexA binding sites (i.e., operators) is unable to grow in the absence of added leucine when this chimera is expressed. However, if such a strain expresses a second chimeric protein which includes a relatively weak transcriptional activation domain (e.g., the B42 activation domain of Ma and Ptashne, Cell 51:113, 1987) fused to a protein capable of interacting specifically with lexA/TR, LEU2 gene expression is activated, and leucine is not required for growth.

Using this system, a number of proteins which interact with thyroid hormone receptor were isolated as follows. A plasmid cDNA library was produced by standard techniques from HeLa cell mRNA and had approximately 10$^6$ original members. Each of these cDNA inserts was fused to the B42 transcriptional activation domain (Ma and Ptashne, Cell 51:113, 1987), and expression of the fusion protein was placed under the control of the inducible yeast GAL10 promoter. In addition to the B42 activating domain, this expression construct also carried, amino to carboxy terminal, an ATG for protein expression, an optional nuclear localization sequence, and an optional epitope tag for rapid immunological detection of fusion protein synthesis. The plasmid also included replication origins for yeast and *E. coli* as well as selectable markers for both.

The fusion protein library was introduced into a yeast strain that expressed the lexA/TRβ chimera and also contained two reporter genes: a lexAop/LEU2 selection construct and a lexAop/β-galactosidase indicator construct. Approximately 10$^7$ initial transformants were generated under nonselective conditions, representing a several fold redundancy relative to the original number of clones in the library. These transformants were recovered and replated under selective (leu$^-$) conditions in the presence or absence of thyroid hormone; based on the results of a functional analysis of intact TRs in yeast (Privalsky et al., Cell 63:1277–1286, 1990), a high concentration of triac (10$^{-5}$M) was added directly to the plates. A number of leucine-independent colonies that contained candidate TR-interacting cDNAs were obtained under both conditions.

The specificity of an interaction between TR and a candidate TR-interacting protein can be checked in several ways. For example, clones which do not activate expression of the lexA/β-galactosidase construct can be eliminated. These clones generally include yeast mutants that activate the LEU2 promoter or mammalian cDNAs that activate by some means other than through the lexA binding sites. Since the expression of the cDNA library fusion protein is under the control of an inducible promoter, the dependence of reporter gene expression on this chimera can also be tested by this criterion.

cDNA library plasmids were recovered from those yeast strains which passed the above tests. Each was reintroduced into the original lexA/TR strain, and their ability to specifically activate expression was confirmed. This step was included because yeast transformants frequently contain one or more plasmids, in addition to the one that allows survival under the selective conditions. To confirm their specificity for TRβ interaction, the rescued plasmids were also introduced into strains containing other lexA chimeras generated in Dr. Brent's laboratory; these included lexA/myc and lexA/cdc2. All of the clones were found to be specific for TRβ by this criterion. cDNA clones that passed all of the above tests were concluded to encode proteins that could specifically interact with the lexA/TR chimera.

Based on restriction mapping, these clones were sorted into distinct classes. Members of each class were sequenced across the fusion junction with the transcriptional activation domain. Sequences of many of these proteins are shown in FIGS. 2–28 (SEQ ID NOS: 1, 3, 6–30).

Although some clones have shown no significant similarities in searches of the sequence databases, most have shown some relationship to known proteins. As described below, two classes showed strong matches over limited domains to nuclear transcription factors. One clone unexpectedly appeared to encode a fragment of the human clathrin heavy chain. Since cell biology considerations argue that TRβ is quite unlikely to have a biologically relevant interaction with clathrin in mammalian cells, it can be assumed that the sensitivity of the selection system allows isolation of fragments of proteins that show some affinity for TR based solely on simple chemical interactions. Interacting proteins of this sort are useful for the production of peptides which interfere with thyroid hormone receptor function (see below).

Because RXRβ interacts with TR and is expressed in HeLa cells (Lied et al., Cell 68:377–395, 1992), RXR fusions would be expected to activate reporter gene expression and be isolated in this selection. To test this prediction, a fragment encoding the RXRα hinge and ligand binding domains was inserted in frame into the transcriptional activation domain fusion vector used to generate the original cDNA library. As expected, this RXR fusion construct allowed the lexA/TR tester strain, but not strains expressing other lexA chimeras, to survive in the absence of leucine and also activated expression of the lexA/β-galactosidase reporter gene (see Table 2). RXR, however, was not identified in the original screen. This is most likely explained by the fact that, although the original library was large, it was extensively amplified, which can decrease representation of rare cDNAs. Moreover, the fusion to the transcriptional activation domain must be in the correct frame and may be functional if the fusion occurs in only a relatively limited number of positions. Since members of the nuclear hormone receptor superfamily are generally expressed at extremely low levels, it is most likely that appropriate RXR clones were simply not present in the amplified library originally screened.

Unexpectedly, nearly all of the lexA/TR interacting cDNAs showed very strong dependence on hormone for activation. Two proteins, JL1 and JL2, which were isolated in the initial selection in the presence of triac, both interacted with the lexA/TR chimera much more strongly when triac was present, as judged by level of expression of β-galactosidase. This hormone$^+$ group constituted the majority of isolated clones (>10 different classes), although there were a smaller number in a hormone- group that interacted only when triac was absent. These classes are shown in Table 1.

TABLE 1

| Class 1 | |
|---|---|
| JL1; | homologous to HIV/TAT interacting proteins MSS1 (Nature 357:700–702, 1992), and to yeast SUG1 (Nature 357:698–700, 1992) |
| JL2; | contains LIM domain (Nature 344:876–879, 1992) |
| 112a-; | no significant homology to any known gene in current databank |
| 103a; | homology to homeobox protein CUT (Nature 333:629–635, 1988) |
| 203a; | homologous to bovine phosphatidylethanolamine-binding protein (EUR. J. BIOCHEM. 166, 333–338, 1987) |
| 204b; | homologous to kinesin-related protein (Mol. Cell. Biol. 11:3395–3398, 1991) |
| 205a; | no significant homology to any known gene in current databank |
| 249a; | no significant homology to any known gene in current databank |
| 351a; | homology to BCL3 (Cell 60:991–997, 1990) |
| 101a; | homology to GRP94 (J. Biol. Chem. 262: 8875–8883, 1987) |
| 223a; | no significant homology to any known gene in current databank |
| 239a; | contains HMG box (Nature 357:282–283, 1992) |
| 410a; | contains SH3 domain (Science 252:668–674, 1991) |
| 417a; | identical to human dUTP pyrophosphatase (Proc. Natl. Acad. Sci. U.S.A. 89:8020–8024, 1992) |
| 418a; | no significant homology to any known gene in current databank |
| 419a; | homology to yeast N-myristoyltransferase (Science 243:796–800, 1989) |
| Class 2 | |
| 107a-; | homologous to rat clathrin heavy chain (Proc. Natl. Acad. Sci. U.S.A. 84: 8805–8809, 1987) |
| 213a-; | no significant homology to any known gene in current databank |
| 113a-; | no significant homology to any known gene in current databank |
| 116a-; | no significant homology to any known gene in current databank |
| 309a-; | homologous to mouse perforin (Proc. Natl. Acad. Sci. U.S.A. 86:247–251, 1989) |
| 227b-; | homologous to mitochondrial hsp70 (DNA 8:233–243, 1989) |
| 224a-; | identical to human ferritin heavy chain (EMBO J. 3:23–27, 1984) |
| 312b-; | identical to human hnRNP C1/2 (Proc. Natl. Acad. Sci. U.S.A. 86:9788–9792, 1989) |
| 215a-; | no significant homology to any known gene in current databank |
| 223a-; | homology to (2'–5') oligoadenylate synthetase (EMBO J. 4:2249–2256, 1985) |
| 240a-; | no significant homology to any known gene in current databank |
| Class 3 | |
| 139a; | homology to possible transcription factor VAC1 (J. Biol. Chem. 267:618–623, 1992) |
| 110a-; | no significant homology to any known gene in current databank |

The fact that virtually all of the isolated clones were specific for one hormone state or the other was surprising.

The genetic properties of sample TR-interacting proteins and RXR fusion proteins are summarized in Table 2.

TABLE 2

| TA fusion | | Lex A fusion | | |
|---|---|---|---|---|
| | | lexA | lexA/TR | lexA/c-myc |
| B42 (vector) | −T3 | leu⁻,W | leu⁻,W | leu⁻,W |
| | +T3 | " | " | " |
| JL1/JL2 | −T3 | leu⁻,W | leu⁻,W | leu⁻,W |
| | +T3 | " | leu⁺,B | " |
| RXR | −T3 | leu⁻,W | leu⁺,B | leu⁻,W |
| | +T3 | " | leu⁺,B | " |

Each of the strains shown in Table 2 contained both the lexAop/LEU2 and the lexAop/β-galactosidase reporter constructs, along with the indicated transcriptional activation (TA) domain fusion proteins; the cDNA cloning vector expressed the B42 transcriptional activation domain alone (Ma and Ptashne, Cell 51:113–119, 1987). Cells containing the indicated TA fusion proteins were transformed with each of the indicated lexA fusion vectors, and phenotypes were tested under various conditions. +/−T3 indicates the presence or absence of $10^{-5}$M triac in the plates (Privalsky et al., Cell 63:1277–1286, 1990); $leu^{-/+}$ denotes the ability of the transformed cells to grow on plates lacking leucine; W/B indicates formation of white or blue colonies on indicator plates containing the indicator X-gal. As expected, the activation conferred by the JL1, JL2, and RXR fusion proteins was dependent on the specific induction of the GAL10 promoter that controls their expression.

JL1 and JL2

The largest class of lexA/TR interacting cDNAs (17 individual isolates) encoded JL1 (also called thyroid hormone receptor-interacting protein 1, or TRIP1). All of the members of the class exhibited the properties summarized above, although some variations in the levels of expression of β-galactosidase in the presence or absence of hormone was observed for clones that varied in position of the junction to the B42 transactivation domain. JL1 is quite similar to several previously identified proteins, particularly TBP1, as indicated in FIG. 2. The functions of this family of proteins are diverse: TBP1 is a nuclear protein that has a poorly understood but apparently important role in transcriptional regulation of HIV (Nelbock et al., Science 248:1650–1653, 1990), while the mammalian protein VCP (Koller and Brownstein, Nature 325:542–545, 1987) and its apparent yeast homolog CDC48 (Frohlich et al., J. Cell. Biol. 114:443–453, 1991) are cytoplasmic proteins of unknown function. TBP1 was isolated by using labeled HIV TAT protein to screen a lambda gt11 expression library and has been found to interact directly with that important viral regulator but not with DNA. Although initially described as an inhibitor of TAT function in cotransfections, a more recent report indicates that TBP1 may act to stimulate TAT activity and may have a direct transcriptional activation function in its own right (Rosen, Abstract. Cold Spring Harbor Symp. Quant. Biol. 57:267, 1992). On these grounds, TBP could be considered a candidate transcriptional coactivator. JL1 is even more homologous to SUG1 (74%, see FIG. 2), a yeast gene recently isolated as a suppressor of a defective version of the GAL4 activator (Swaffield et al., Nature 357:698, 1992). By genetic analysis, SUG1 appears to be a coactivator capable of specifically interacting with GAL4, and JL1 similarly encodes a thyroid hormone-dependent coactivator protein. Functionally, they are at least partially homologous, with expression of JL1 able to rescue a SUG1 temperature-sensitive lethal mutant in a yeast system in a similar manner to wild-type SUG1 (Swaffield et al., manuscript submitted). This interchangeability indicates that the SUG1 and JL1 transcriptional function has been highly conserved, most likely within the conserved ATPase-containing domain common to the superfamily. Thus, they are likely to bind the same activation domains and exert transcriptional control in a similar manner.

JL2, encoded by a single recovered cDNA, includes two copies of the LIM domain originally identified as a conserved motif in three putative transcription factors: Lin-11 (Freyd et al., Nature 344:876–879, 1990), Isl-1 (Karlsson et al., Nature 344:879–882, 1990) and Mec-3 (Way, and Chalfie, Cell 54:5–16, 1988). In the context of endocrine control of gene expression, isl-1 is particularly interesting since it is an activator of the insulin enhancer. It is expressed in both developing and mature islet cells and is thought to be involved in the initial differentiation of the islet cells, in addition to its presumed role in regulating insulin expression. Isl-1 is also expressed in a subset of neurons in the adult and, recently has been shown to be expressed at very early stages of embryonic motor neuron differentiation. The pattern of this early expression suggests that isl-1 may play a primary role in the initial determination of motor neuron cell fate in response to inductive signals from the notochord and floor plate (Ericson et al., Science 256:155–1560, 1992). Consistent with this possibility, lin-11 and mec-3 are both C. elegans developmental regulators, associated with cell lineage determination in mechanosensory neurons and a vulval precursor cell, respectively.

Lin-11, isl-1, and mec-3 contain a homeobox-type DNA binding domain in addition to two copies of the LIM domain, as do other recently identified members of this family (see, e.g., Cohen et al., Genes & Dev. 6:715–729, 1992; Taira et al., Genes & Dev. 6:356–366, 1992). However, a homeodomain is absent in a three related LIM domain-containing proteins called rhombotins 1–3, at least two of which are the products of putative oncogenes (Rosen, Abstract, Cold Spring Harbor Symp. Quant. Biol. 57:267, 1992). The LIM domain consensus sequence contains conserved cysteine and histidine residues, and it has recently been demonstrated that at least the lin-11 version binds metal ions (2 atoms of Zn and 4 of Fe; Li et al., Proc. Natl. Acad. Sci. USA 88:9210, 1991). As indicated in FIG. 3, JL2 has a good match with the LIM consensus in lin-11; it does not, however, include a homeobox. In this regard, JL2 appears to be more like the rhombotins than it is like the transcription factors lin-11, isl-1, and mec-3.

An initial determination of the pattern of expression of JL1 and JL2 has begun. As indicated in FIG. 29, the approximately 2.1 kb JL1 mRNA is expressed at various levels in all the human tissues examined. The slightly smaller 1.8 kb JL2 mRNA is expressed in a somewhat narrower range of tissues. Based on the amount of time required to visualize the bands, both mRNAs are present at very low levels, consistent with a regulatory role. As judged by exposure time, the JL1 mRNA appears to be expressed at an approximately 6 fold higher level than that of JL2, as would be expected from the higher number of JL1 clones isolated.

S351a

The isolated polypeptide 351a was found to have some homology (about 40% identity at the amino acid level) to BCL3. The BCL3 gene product is characterized by seven 30 amino acid ankyrin repeats (Ohno et al., Cell 60:991–997, 1990), so named because of their initial identification in the erythrocyte membrane protein ankyrin. There are now many examples of related proteins, which share the repeated structure consisting of a loosely conserved, approximately 30 amino acid motif (the ankyrin repeat). These related proteins have diverse functions, but one subgroup, including BCL3, IκB, and others have specific functions in the regulation of transcription. These proteins bind specifically to the family of related proteins that form a dimeric transcription factor generically known as NFκB. The interaction of IκB with NFκB inhibits its ability to activate transcription of target genes because the complex is retained in the cytoplasm. This retention is possibly due to IκB binding to and masking NFκB's nuclear localization signals. The interaction with BCL3, in contrast, apparently occurs in the nucleus and leads to a stimulation of transcriptional activity by unknown mechanisms. This family of proteins thus appears to have a modulatory effect on transcription, which allows regulation of a variety of gene products involved in numerous cellular responses. Hence, members of this subgroup can have either inhibitory or stimulatory effects on transcription, and it is unclear what function in this regard the 351a peptide has in its interactions with TR. FIG. 30 shows the similarity between 351a and the relevant portion of BCL3. The ankyrin repeats of BCL3 are underlined. The similarity is clearly greatest over the N-terminal portion of the sequence shown, in the stretch which corresponds to the 4th of the 7 repeats in BCL3. Overall, the relationship is not particularly strong, and may account for the observation the BCL3 does not interact with either TR or RXR in the interaction trap of this invention, while 351a does. 351a clearly has a ligand dependent TR and RXR interaction function not shared by its closest relative within the family of proteins containing ankyrin repeats.

Experiments in yeast have shown that although both the lexA-TR chimera used in the interaction trap and TR alone activate transcription in yeast very poorly in the presence or absence of thyroid hormone, coexpression of the TR heterodimer partner RXR restores hormone dependent transcriptional activation of both (on lexA operators and TR binding sites, respectively). Adding the lexA-351a construct to the intact TR+RXR strongly inhibits this latter activation. This inhibition could be a consequence of a direct inhibition associated with 351a binding, or could be an indirect effect associated with the fact that the lexA-351a chimera is missing essential sequences necessary for a co-stimulatory function analogous to that of BCL3. In an additional series of experiments, lexA-351a alone was also found to be transcriptionally inactive in yeast. However, coexpression of intact TR causes lexA-351a to become a T3-dependent transcriptional activator. This indicates that the interaction of 351a with TR does not result in a complex that is inherently inactive, resolution of the larger question of whether the native 351-TR interaction is stimulatory or inhibitory will require analysis of the function of the full length 351a protein.

From a practical point of view, the inhibitory effect of the lexA-351a chimera provides a direct demonstration of a potentially useful function of the truncated protein, namely inhibition of TR function. Liposomes or other delivery systems known in the art could be employed to deliver this truncated protein or the minimum biologically active fragment thereof for therapeutic uses. The direct demonstration of the negative effect provides a clear demonstration of the general concept of using 351a to block TR action. 351a could provide a therapeutically useful antagonist of TR function analogous to, for instance, the anti-steroid effects of RU486, a drug that inhibits transcription in members of the nuclear hormone receptor family. The mechanism of action of RU486 is distinct from 351a, and does not exert effects on thyroid hormone receptors, and thus the inhibitory effect of 351a on transcriptional regulation in the thyroid hormone receptor system is of potentially major significance.

To determine whether a TR-interacting protein has a positive or a negative effect on TR function, cotransfections of the TR-interacting protein expression vector and a TRβ or TRα expression vector are carried out by standard techniques, preferably, in a host cell line that does not express significant levels of the TR-interacting protein (see, e.g., Ausubel et al., *Current Protocols in Molecular Biology*, John Wiley & Sons, 1989). A TR-interacting protein which acts as a positive regulator (e.g., a coactivator), is indicated by increased TR activity in such an assay. Conversely, a TR-interacting protein which acts as a negative regulator is indicated by reduced TR activity. Cotransfection assays of this sort are generally described in Ausubel et al. (supra).

In one particular example, the TR-interacting protein-encoding cDNA is inserted into the CDM8 vector (Seed, B., Nature 329:840, 1987), and increasing doses of this plasmid are cotransfected with a TRβ expression vector (Brent et al., J. Biol. Chem. 264:178, 1989) plus one of several different reporter genes containing various T3REs linked, e.g., to the herpes virus thymidine kinase (TK) gene (Brent supra). In these transfections, the level of total expression vector is maintained at a constant level by addition of CDM8, as necessary. To control for variations in transfection efficiency and for effects of the TR-interacting protein on the TK promoter, transfections also include pTKGH (Selden et al., Moll. Cell. Biol. 6:3173, 1986), a plasmid which directs expression of human growth hormone under the control of the same TK promoter. As controls for regulatory effects, Pit-1, c-fos and c-jun may also be cotransfected with TRβ and the T3RE reporters.

Since the relative and absolute levels of expression of TRβ and its potential partners may be crucial for observation of any effect, a negative result is first confirmed at a variety of doses of each vector. Several cell lines are also examined. If however, no evidence for a specific effect of a TR-interacting protein on TR function is observed after these steps, it will be concluded that the interaction with TRβ is likely to be an artifact of the sensitivity of the genetic selection originally used to isolate them.

If, on the other hand, the TR-interacting protein alters TR function, the specificity of the effect is examined. Simple cotransfections of the TR-interacting protein expression vector with RSVCAT or TKCAT vectors is used to confirm that any negative effect is not a consequence of squelching (Ptashne and Gann, Nature 346:329–331, 1990). Cotransfections of appropriate reporters with the TR-interacting protein expression vectors plus vectors expressing TRα, the RARs, VDR, GR, ER or others may also be carried out.

The portions of any particular TR-interacting protein required for functional interaction may be determined initially by standard deletion analysis, with mutant proteins tested by the above cotransfection assay. The results of such mapping may be confirmed and extended by testing the effect of the same mutations on the lexA/TR dependent activation of expression in yeast, and by the following biochemical interaction assays.

To determine directly whether a TR-interacting protein can interact with thyroid hormone receptor, antiserum directed against one of the potential partners is tested for its ability to coimmunoprecipitate the other. This may be assayed directly using bacterially-produced TR proteins and antiserum or monoclonal antibodies that recognize some region of the TRβ protein. In one particular example of such an assay, in vitro translated, $^{35}S$ labeled TR-interacting protein is mixed with TRβ protein in the presence or absence of T3, and the mixture is immunoprecipitated with an antiserum that recognizes the N-terminus of the TR. Similarly labeled RXRβ protein, which is known to interact strongly with TRβ in such procedures, is used as a positive control. The immunoprecipitated material is resolved by SDS PAGE, and the presence of the TR-interacting protein or RXR in such immunoprecipitates is assessed by autoradiography. The observation of T3-dependent coimmunoprecipitation of the potential TR binding proteins with the TR provides strong evidence for a direct interaction with the receptor. A general description of in vitro translation of proteins is described in Hope and Struhl, Cell 43:177–188, 1985. Labelling proteins with $^{35}S$, production of antibodies (including monoclonal antibodies), and immunoprecipitation procedures are described in Ausubel (infra).

Lack of such a coimmunoprecipitation may suggest that the interaction of a particular protein with TR is too transient to be detected by this approach. This can be tested by addition of various crosslinking reagents to the binding reactions, as described in the analysis of the interactions of GR with AP-1, for example (Yang-Yen et al., Cell 62:1205–1215, 1990). It is important to control for the variety of artifactual associations that may complicate interpretation of such studies. If crosslinking does not reveal an interaction between a TR-interacting protein and TRβ, even in the presence of extracts that might supply additional cofactors required, it may be that their interaction in yeast is artifactual.

Truncated versions of TR-interacting proteins can also be tested using this method to identify specific portions of each protein required for TR interaction. This is of particular importance from the point of view of potential pharmacologic intervention with the interaction, since such fragments may facilitate the production of specific inhibitors of TR function.

TR-Interacting Proteins and Antibodies
Polypeptide Expression

In general, polypeptides according to the invention may be produced by transformation of a suitable host cell with all or part of a TR-interacting protein-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The TR-interacting protein may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, MD; also, see, e.g., Ausubel et al., *Current Protocols in Molecular Biology*, John Wiley & Sons, New York, 1989). The method of transformation or transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in *Cloning Vectors: A Laboratory Manual* (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a TR-interacting protein would be inserted into the pMAMneo vector in an orientation designed to allow expression. The recombinant TR-interacting protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, a TR-interacting protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the TR-interacting protein is cloned into an expression vector which includes the dihydrofolate reductase (DHFR) gene. Integration of the plasmid and, therefore, the TR-interacting protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV (A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

Once the recombinant TR-interacting protein is expressed, it is isolated, e.g., using affinity chromatography. In one example, an anti-TR-interacting protein antibody (e.g., produced as described herein) may be attached to a column and used to isolate the TR-interacting protein. Lysis and fractionation of TR-interacting protein-harboring cells prior to affinity chromatography may be performed by standard methods (see, e.g., Ausubel et al., supra). Alternatively, a TR-interacting protein fusion protein, for example, a TR-interacting protein-maltose binding protein, a TR-interacting protein-β-galactosidase, or a TR-interacting protein-trpE fusion protein, may be constructed and used for TR-interacting protein isolation (see, e.g., Ausubel et al., supra; New England Biolabs, Beverly, Mass.).

Once isolated, the recombinant protein can, if desired, be further purified, e.g., by high performance liquid chromatography (see, e.g., Fisher, Laboratory *Techniques In Biochemistry And Molecular Biology*, eds., Work and Burdon, Elsevier, 1980).

Polypeptides of the invention, particularly short TR-interacting protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful TR-interacting protein fragments or analogs (described herein).

Anti-TR-Interacting Protein Antibodies

Human TR-interacting protein (or immunogenic fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may also be prepared using the TR-interacting proteins described above and standard hybridoma technology (see, e.g., Kohler et al., Nature 256:495, 1975; Kohler et al., *Eur. J. Immunol.* 6:511, 1976; Kohler et al., *Eur. J. Immunol.* 6:292, 1976; Hammerling et al., In *Monoclonal Antibodies and T Cell Hybridomas*, Elsevier, NY, 1981; Ausubel et al., supra).

Once produced, polyclonal or monoclonal antibodies are tested for specific TR-interacting protein recognition by Western blot or immunoprecipitation analysis (by the methods described in Ausubel et al., supra). Antibodies which specifically recognize a TR-interacting protein are considered to be useful in the invention; such antibodies may be used, e.g., in an immunoassay to monitor the level of TR-interacting protein produced by a mammal or to determine the subcellular location of any of these thyroid hormone receptor modulatory proteins.

Preferably, antibodies of the invention are produced using fragments of the TR-interacting protein which lie outside highly conserved regions and appear likely to be antigenic, by criteria such as high frequency of charged residues. In one specific example, such fragments are generated by standard techniques of PCR and cloned into the pGEX expression vector (Ausubel, F. M. et al., *Current Protocols in Molecular Biology* (Greene Pub. Assoc., New York, 1992). Fusion proteins are expressed in *E. coli* and purified using a glutathione agarose affinity matrix as described in (Ausubel, F. M. et al., *Current Protocols in Molecular Biology* (Greene Pub. Assoc., New York, 1992)). To attempt to minimize the potential problems of low affinity or specificity of antisera, two or three such fusions are generated for each protein, and each fusion is injected into two rabbits. Antisera are raised by injections in a series including at least three booster injections. This approach has been successfully used by applicants to generate antibodies capable of discriminating between the different TR isoforms.

Antisera is cleared of anti-GST antibodies using GST immobilized on a glutathione column, and the antisera are checked by ELISA for titer and specificity, using GST fusion proteins as controls. Antisera is also checked for its ability to immunoprecipitate in vitro translated TR-interacting proteins or control proteins, such as Pit-1 or RARα. Western blots of total or nuclear vs. cytoplasmic fractionated HeLa cell proteins are also probed with the antisera to assess specificity and to characterize subcellular compartmentalization. In these and other immunologic assays, specificity is confirmed by the specific competition with the GST fusion protein.

Once the specificity of an antiserum is confirmed, it may be used in any standard indirect immunofluorescence procedure to determine the subcellular distribution of the TR-interacting protein in a particular cell type. Based on their similarity to nuclear transcriptional regulators and their interaction with TRs, TR-interacting proteins are likely to be nuclear localized.

Use

The proteins described herein interact with thyroid hormone receptor and are thus likely to mediate or modulate TR function. Because of their effects on thyroid receptor activity, such proteins (or peptides derived from these proteins, particularly, short peptides which are capable of TR interaction), may facilitate the production of pharmacologic modifiers of receptor function.

In particular, TR-interacting proteins of the invention which positively regulate TR function in vivo or in vitro (e.g., as assayed in cotransfections as described above) may be used to produce therapeutic peptides which include a TR interaction domain but which lack a TR activity-enhancing domain, for example, a domain which interacts with the transcriptional apparatus; the efficacy of such peptides may also, e.g., as assayed as described above. Such peptides would bind TR, interfering with receptor binding by the native TR-interacting protein, and thereby reducing TR activity. Peptides of this sort would be useful in the treatment of hyperthyroidism.

Conversely, interacting peptides derived from TR-interacting proteins which negatively regulate TR function, as assayed in vivo or in vitro (again, e.g., by the assays described above) may be used to produce therapeutic peptides which block the normal interaction between the receptor and the negatively acting TR-interacting protein. These peptides may similarly be administered to a mammal to treat thyroid disorders.

Such therapeutic polypeptides of the invention may be administered by any appropriate route, e.g., intravenously, at a dosage which is effective to increase or decrease thyroid function. Treatment may be repeated as necessary for alleviation of disease symptoms.

The polypeptides of the invention are also useful for identifying those compartments of mammalian cells which contain proteins important to the function of the thyroid hormone receptor. Antibodies specific for a particular TR-interacting protein (or any nuclear hormone receptor-interacting protein) may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

Antibodies specific for TR-interacting proteins also find diagnostic use in the detection or monitoring of thyroid disorders. Levels of a TR-interacting protein in a sample may be assayed by any standard technique. For example, its expression may be monitored by standard Northern blot analysis or may be aided by PCR (see, e.g., Ausubel et al., supra; *PCR Technology: Principles and Applications for DNA Amplification*, ed., H. A. Ehrlich, Stcokton Press, NY). These techniques are enabled by the provision of the TR-interacting protein sequences described herein. Alternatively, standard immunological or immunohistochemical procedures (e.g., those described above) may also be used with the antibodies described herein for TR-interacting protein detection.

Other Embodiments

In other embodiments, the invention includes any protein which is substantially homologous to a human TR-interacting protein (FIGS. 2–28, SEQ ID NOS: 1, 3, 6–30); such homologs include other substantially pure naturally occurring mammalian TR-interacting protein proteins as well as allelic variants; natural mutants; induced mutants; proteins encoded by DNA that hybridizes to the TR-interacting protein sequence of any of FIGS. 2–28 (SEQ ID NOS: 1, 3, 6–30) under high stringency conditions or low stringency conditions (e.g., washing at 2× SSC at 40° C. with a probe length of at least 40 nucleotides); and polypeptides or proteins specifically bound by antisera directed to a TR-interacting protein, especially by antisera to the TR binding domain of the TR-interacting protein. The term also includes chimeric polypeptides that include a TR-interacting protein fragment.

The invention further includes analogs of any naturally occurring TR-interacting protein. Analogs can differ from the naturally occurring TR-interacting protein by amino acid sequence differences, by post-translational modifications, or by both. Analogs of the invention will generally exhibit at least 80%, more preferably 90%, and most preferably 95% or even 99%, homology with all or part of a naturally occurring TR-interacting protein sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring TR-interacting protein by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., *Current Protocols in Molecular Biology*, John Wiley & Sons, 1989, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes TR-interacting protein fragments. As used herein, the term "fragment", means at least 10 contiguous amino acids, preferably at least 30 contiguous amino acids, more preferably at least 50 contiguous amino acids, and most preferably at least 60 to 80 or more contiguous amino acids. Fragments of TR-interacting proteins can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate interaction of the peptide with a thyroid hormone receptor.

Other embodiments are within the following claims.

SEQUENCE LISTING (1) GENERAL INFORMATION:

(iii) NUMBER OF SEQUENCES:    31

(2) INFORMATION FOR SEQ ID NO:    1:

(i) SEQUENCE CHARACTERISTICS:
        (A) LENGTH:              406
        (B) TYPE:                amino acid
        (C) STRANDEDNESS:
        (D) TOPOLOGY: Not Relevant (xi) SEQUENCE DESCRIPTION: SEQ ID NO: 1:

```
Met Ala Leu Asp Gly Pro Glu Gln Met Glu Leu Glu Glu Gly Lys Ala
 1               5                  10                  15

Gly Ser Gly Leu Arg Gln Tyr Tyr Leu Ser Lys Ile Glu Glu Leu Gln
            20                  25                  30

Leu Ile Val Asn Asp Lys Ser Gln Asn Leu Arg Arg Leu Gln Ala Gln
        35                  40                  45

Arg Asn Glu Leu Asn Ala Lys Val Arg Leu Leu Arg Glu Glu Leu Gln
    50                  55                  60

Leu Leu Gln Glu Gln Gly Ser Tyr Val Gly Glu Val Val Arg Ala Met
65                  70                  75                  80

Asp Lys Lys Lys Val Leu Val Lys Val His Pro Glu Gly Lys Phe Val
                85                  90                  95

Val Asp Val Asp Lys Asn Ile Asp Ile Asn Asp Val Thr Pro Asn Cys
            100                 105                 110

Arg Val Ala Leu Arg Asn Asp Ser Tyr Thr Leu His Lys Ile Leu Pro
        115                 120                 125

Asn Lys Val Asp Pro Leu Val Ser Leu Met Met Val Glu Lys Val Pro
    130                 135                 140
```

```
Asp Ser Thr Tyr Glu Met Ile Gly Gly Leu Asp Lys Gln Ile Lys Glu
145                 150                 155                 160

Ile Lys Glu Val Ile Glu Leu Pro Val Lys His Pro Glu Leu Phe Glu
                165                 170                 175

Ala Leu Gly Ile Ala Gln Pro Lys Gly Val Leu Leu Tyr Gly Pro Pro
            180                 185                 190

Gly Thr Gly Lys Thr Leu Leu Ala Arg Ala Val Ala His His Thr Asp
            195                 200                 205

Cys Thr Phe Ile Arg Val Ser Gly Ser Glu Leu Val Gln Lys Phe Ile
        210                 215                 220

Gly Glu Gly Ala Arg Met Val Arg Glu Leu Phe Val Met Ala Arg Glu
225                 230                 235                 240

His Ala Pro Ser Ile Ile Phe Met Asp Glu Ile Asp Ser Ile Gly Ser
                245                 250                 255

Ser Arg Leu Glu Gly Gly Ser Gly Gly Ser Ser Glu Val Gln Arg Gln
            260                 265                 270

Met Leu Glu Leu Leu Asn Gln Leu Asp Gly Phe Glu Ala Thr Lys Asn
        275                 280                 285

Ile Lys Val Ile Met Ala Thr Asn Arg Ile Asp Met Leu Asp Ser Ala
290                 295                 300

Leu Leu Arg Pro Gly Arg Ile Asp Arg Lys Ile Glu Phe Pro Pro Pro
305                 310                 315                 320

Asn Glu Glu Ala Arg Leu Asp Ile Leu Lys Ile His Ser Arg Lys Met
                325                 330                 335

Asn Leu Thr Arg Gly Ile Asn Leu Arg Lys Ile Ala Glu Leu Met Pro
            340                 345                 350

Gly Ala Ser Gly Ala Glu Val Lys Gly Val Cys Thr Glu Ala Gly Met
        355                 360                 365

Tyr Ala Leu Arg Glu Arg Arg Val His Val Thr Gln Glu Asp Phe Glu
370                 375                 380

Met Ala Val Ala Lys Val Met Gln Lys Asp Ser Glu Lys Asn Met Ser
385                 390                 395                 400

Ile Lys Lys Leu Trp Lys
            405

(2) INFORMATION FOR SEQ ID NO:    2:

(i) SEQUENCE CHARACTERISTICS:
        (A) LENGTH:            405
        (B) TYPE:              amino acid
        (C) STRANDEDNESS:
        (D) TOPOLOGY: Not Relevant (xi) SEQUENCE DESCRIPTION: SEQ ID NO: 2:

Met Thr Ala Ala Val Thr Ser Ser Asn Ile Val Leu Glu Thr His Glu
1               5                   10                  15

Ser Gly Ile Lys Pro Tyr Phe Glu Gln Lys Ile Gln Glu Thr Glu Leu
            20                  25                  30

Lys Ile Arg Ser Lys Thr Glu Asn Gly Arg Arg Leu Glu Ala Gln Arg
        35                  40                  45

Asn Ala Leu Asn Asp Lys Val Arg Phe Ile Lys Asp Glu Leu Arg Leu
    50                  55                  60

Leu Gln Glu Pro Gly Ser Tyr Val Gly Glu Val Ile Lys Ile Val Ser
65                  70                  75                  80

Asp Lys Lys Val Leu Val Lys Val Gln Pro Glu Gly Lys Tyr Ile Val
                85                  90                  95
```

Asp Val Ala Lys Asp Ile Asn Val Lys Asp Leu Lys Ala Ser Gln Arg
            100                 105                 110

Val Cys Leu Arg Ser Asp Ser Tyr Met Leu His Lys Val Leu Glu Asn
            115                 120                 125

Lys Ala Asp Pro Leu Val Ser Ile Met Met Val Glu Lys Val Pro Asp
            130                 135                 140

Ser Thr Tyr Asp Met Val Gly Gly Leu Thr Lys Gln Ile Lys Glu Ile
145                 150                 155                 160

Lys Glu Val Ile Glu Leu Pro Val Lys His Pro Glu Leu Phe Glu Ser
            165                 170                 175

Leu Gly Ile Ala Gln Pro Lys Gly Val Ile Leu Tyr Gly Pro Pro Gly
            180                 185                 190

Thr Gly Lys Thr Leu Leu Ala Arg Ala Val Ala His His Thr Asp Cys
            195                 200                 205

Lys Phe Ile Arg Val Ser Gly Ala Glu Leu Val Gln Lys Tyr Ile Gly
            210                 215                 220

Glu Gly Ser Arg Met Val Arg Glu Leu Phe Val Met Ala Arg Glu His
225                 230                 235                 240

Ala Pro Ser Ile Ile Phe Met Asp Glu Ile Asp Ser Ile Gly Ser Thr
            245                 250                 255

Arg Val Glu Gly Ser Gly Gly Asp Ser Glu Val Gln Arg Thr Met
            260                 265                 270

Leu Glu Leu Leu Asn Gln Leu Asp Gly Phe Glu Thr Ser Lys Asn Ile
            275                 280                 285

Lys Ile Ile Met Ala Thr Asn Arg Leu Asp Ile Leu Asp Pro Ala Leu
            290                 295                 300

Leu Arg Pro Gly Arg Ile Asp Arg Lys Ile Glu Phe Pro Pro Pro Ser
305                 310                 315                 320

Val Ala Ala Arg Ala Glu Ile Leu Arg Ile His Ser Arg Lys Met Asn
            325                 330                 335

Leu Thr Arg Gly Ile Asn Leu Arg Lys Val Ala Glu Lys Met Asn Gly
            340                 345                 350

Cys Ser Gly Ala Asp Val Lys Gly Val Cys Thr Glu Ala Gly Met Tyr
            355                 360                 365

Ala Leu Arg Glu Arg Arg Ile His Val Thr Gln Glu Asp Phe Glu Leu
            370                 375                 380

Ala Val Gly Lys Val Met Asn Lys Asn Gln Glu Thr Ala Ile Ser Val
385                 390                 395                 400

Ala Lys Leu Phe Lys
            405

(2) INFORMATION FOR SEQ ID NO:    3:

(i) SEQUENCE CHARACTERISTICS:
        (A) LENGTH:            185
        (B) TYPE:              amino acid
        (C) STRANDEDNESS:
        (D) TOPOLOGY: Not Relevant (xi) SEQUENCE DESCRIPTION: SEQ ID NO: 3:

Met Pro Gly Pro Leu Arg Gly Gln His Phe Tyr Ala Val Glu Arg Arg
1                   5                   10                  15

Ala Tyr Cys Glu Gly Cys Tyr Val Ala Thr Leu Glu Lys Cys Ala Thr
                    20                  25                  30

Cys Ser Gln Pro Ile Leu Asp Arg Ile Leu Arg Ala Met Gly Lys Ala
            35                  40                  45

```
Tyr His Pro Gly Cys Phe Thr Cys Val Val Cys His Arg Gly Leu Asp
     50                  55                  60

Gly Ile Pro Phe Thr Val Asp Ala Thr Ser Gln Ile His Cys Ile Glu
 65                  70                  75                  80

Asp Phe His Arg Lys Phe Ala Pro Arg Cys Ser Val Cys Gly Gly Ala
                 85                  90                  95

Ile Met Pro Glu Pro Gly Gln Glu Glu Thr Val Arg Ile Val Ala Leu
             100                 105                 110

Asp Arg Ser Phe His Ile Gly Cys Tyr Lys Cys Glu Glu Cys Gly Leu
         115                 120                 125

Leu Leu Ser Ser Glu Gly Glu Cys Gln Gly Cys Tyr Pro Leu Asp Gly
     130                 135                 140

His Ile Leu Cys Lys Ala Cys Arg Pro Gly Ala Ser Arg Ser Ser Gln
145                 150                 155                 160

Pro Pro Ser Gly Leu Thr Ala Glu Ser Ser Met Lys Tyr Leu Leu Gly
                 165                 170                 175

Ser Gln Phe Gln Phe Pro Ser Phe Asp
        180                 185

(2) INFORMATION FOR SEQ ID NO:    4:

(i) SEQUENCE CHARACTERISTICS:
        (A) LENGTH:              122
        (B) TYPE:                amino acid
        (C) STRANDEDNESS:
        (D) TOPOLOGY: Not Relevant (xi) SEQUENCE DESCRIPTION: SEQ ID NO: 4:

Cys Ala Thr Cys Ser Gln Pro Ile Leu Asp Arg Ile Leu Arg Ala Met
 1               5                  10                  15

Gly Lys Ala Tyr His Pro Gly Cys Phe Thr Cys Val Val Cys His Arg
             20                  25                  30

Gly Leu Asp Gly Ile Pro Phe Thr Val Asp Ala Thr Ser Gln Ile His
         35                  40                  45

Cys Ile Glu Asp Phe His Arg Lys Phe Ala Pro Arg Cys Ser Val Cys
     50                  55                  60

Gly Gly Ala Ile Met Pro Glu Pro Gly Gln Glu Glu Thr Val Arg Ile
 65                  70                  75                  80

Val Ala Leu Asp Arg Ser Phe His Ile Gly Cys Tyr Lys Cys Glu Glu
                 85                  90                  95

Cys Gly Leu Leu Leu Ser Ser Glu Gly Glu Cys Gln Gly Cys Tyr Pro
             100                 105                 110

Leu Asp Gly His Ile Leu Cys Lys Ala Cys
         115                 120

(2) INFORMATION FOR SEQ ID NO:    5:

(i) SEQUENCE CHARACTERISTICS:
        (A) LENGTH:              114
        (B) TYPE:                amino acid
        (C) STRANDEDNESS:
        (D) TOPOLOGY: Not Relevant (xi) SEQUENCE DESCRIPTION: SEQ ID NO: 5:

Cys Ala Ala Cys Ala Gln Pro Ile Leu Asp Arg Tyr Val Phe Thr Val
 1               5                  10                  15

Leu Gly Lys Cys Trp His Gln Ser Cys Leu Arg Cys Cys Asp Cys Arg
             20                  25                  30
```

```
Ala Pro Met Ser Met Thr Cys Phe Ser Arg Asp Gly Leu Ile Leu Cys
         35                  40                  45

Lys Thr Asp Phe Ser Arg Arg Tyr Ser Gln Arg Cys Ala Gly Cys Asp
 50                  55                  60

Gly Lys Leu Glu Lys Glu Asp Leu Val Arg Arg Ala Arg Asp Lys Val
 65                  70                  75                  80

Phe His Ile Arg Cys Phe Gln Cys Ser Val Cys Gln Arg Leu Leu Asp
                 85                  90                  95

Thr Gly Asp Gln Leu Tyr Ile Met Glu Gly Asn Arg Phe Val Cys Gln
             100                 105                 110

Ser Asp
```

(2) INFORMATION FOR SEQ ID NO: 6:

(i) SEQUENCE CHARACTERISTICS:
        (A) LENGTH:         495
        (B) TYPE:           nucleic acid
        (C) STRANDEDNESS:   double
        (D) TOPOLOGY:       linear (xi) SEQUENCE DESCRIPTION: SEQ ID NO: 6:

```
AAC CCA ATT CTT ACC AGT TTG TTG CAA ATC ACA GGG AAC NGG GGG TCT      48
Asn Pro Ile Leu Thr Ser Leu Leu Gln Ile Thr Gly Asn Xaa Gly Ser
 1               5                  10                  15

ACC ATT GGC TCG AGT CCG ACC CCT CCT CAT CAC ACG CCG CCA CCT GTC      96
Thr Ile Gly Ser Ser Pro Thr Pro Pro His His Thr Pro Pro Pro Val
             20                  25                  30

TCT TCG ATG GCC GGC AAC ACC AAG AAC CAC CCG ATG CTC ATG AAC CTT     144
Ser Ser Met Ala Gly Asn Thr Lys Asn His Pro Met Leu Met Asn Leu
         35                  40                  45

CTT AAA GAT AAT CCT GCC CAG GAT TTC TCA ACC CTT TAT GGA AGC AGC     192
Leu Lys Asp Asn Pro Ala Gln Asp Phe Ser Thr Leu Tyr Gly Ser Ser
 50                  55                  60

CCT TTA GAA AGG CAG AAC TCC TCT TTC GGC TCA CCC CGC ATG GAA ATA     240
Pro Leu Glu Arg Gln Asn Ser Ser Phe Gly Ser Pro Arg Met Glu Ile
 65                  70                  75                  80

TGC TCG GGG AGC AAC AAG ACC AAG AAA AAG AAG TCA TCA AGA TTA CCA     288
Cys Ser Gly Ser Asn Lys Thr Lys Lys Lys Lys Ser Ser Arg Leu Pro
                 85                  90                  95

CCT GAG AAA CCA AAA CAA CGC GAG GAT ATA ATT GCC AAA ACC AGG CTT     336
Pro Glu Lys Pro Lys Gln Arg Glu Asp Ile Ile Ala Lys Thr Arg Leu
             100                 105                 110

GAG GTT GGT GAC TCT TGA AAG ATT TTC TTT CTT CAG GCC TAG ATC AGA     384
Glu Val Gly Asp Ser     Lys Ile Phe Phe Leu Gln Ala     Ile Arg
             115                 120                 125

AAA TTA AGT GCA GCA ATA TCA TGA ATT CTC AGA AGC CCT TTC AGG GAG     432
Lys Leu Ser Ala Ala Ile Ser     Ile Leu Arg Ser Pro Phe Arg Glu
             130                 135                 140

CCA GTG AGT CAT ACA GTA TCC ACA GTT GAG TCA CTT AAA GAT GTC AGT     480
Pro Val Ser His Thr Val Ser Thr Val Glu Ser Leu Lys Asp Val Ser
145                 150                 155                 160

ATA CGA AAC ATT ATT                                                 495
Ile Arg Asn Ile Ile
                165
```

(2) INFORMATION FOR SEQ ID NO: 7:

(i) SEQUENCE CHARACTERISTICS:
        (A) LENGTH:         885
        (B) TYPE:           nucleic acid
        (C) STRANDEDNESS:   double
        (D) TOPOLOGY:       linear (xi) SEQUENCE DESCRIPTION: SEQ ID NO: 7:

```
CTC AAA TGT AGC ACC GTC GTC TGC GTG ATC TGC TTG GAG AAG CCC AAA        48
Leu Lys Cys Ser Thr Val Val Cys Val Ile Cys Leu Glu Lys Pro Lys
1               5                   10                  15

TAC CGC TGT CCA GCC TGC CGC GTG CCC TAC TGC TCG GTA GTC TGC TTC        96
Tyr Arg Cys Pro Ala Cys Arg Val Pro Tyr Cys Ser Val Val Cys Phe
                20                  25                  30

CGG AAG CAC AAA GAA CAG TGC AAC CCT GAA ACT CGT CCT GTT GAG AAA       144
Arg Lys His Lys Glu Gln Cys Asn Pro Glu Thr Arg Pro Val Glu Lys
            35                  40                  45

AAA ATA AGA TCA GCT CTT CCT ACC AAA ACC GTA AAG CCT GTG GAA AAC       192
Lys Ile Arg Ser Ala Leu Pro Thr Lys Thr Val Lys Pro Val Glu Asn
        50                  55                  60

AAA GAT GAT GAT GAC TCT ATA GCT GAT TTT CTC AAT AGT GAT GAG GAA       240
Lys Asp Asp Asp Asp Ser Ile Ala Asp Phe Leu Asn Ser Asp Glu Glu
65                  70                  75                  80

GAA GAC AGA GTT TCT TTG CAG AAT TTA AAG AAT TTA GGG GAA TCT GCA       288
Glu Asp Arg Val Ser Leu Gln Asn Leu Lys Asn Leu Gly Glu Ser Ala
                85                  90                  95

ACA TTA AGA AGC TTA TTG CTC AAT CCA CAC CTC AGG CAG TTG ATG GTC       336
Thr Leu Arg Ser Leu Leu Leu Asn Pro His Leu Arg Gln Leu Met Val
            100                 105                 110

AAC CTC GAT CAG GGA GAA GAC AAA GCA AAG CTC ATG AGA GCT TAC ATG       384
Asn Leu Asp Gln Gly Glu Asp Lys Ala Lys Leu Met Arg Ala Tyr Met
        115                 120                 125

CAA GAG CCT TTG TTT GTG GAG TTT GCA GAC TGC TGT TTA GGA ATT GTG       432
Gln Glu Pro Leu Phe Val Glu Phe Ala Asp Cys Cys Leu Gly Ile Val
    130                 135                 140

GAG CCA TCC CAG AAT GAG GAG TCT TAA GAT GGA TTA TTG TGC TGC TTG       480
Glu Pro Ser Gln Asn Glu Glu Ser     Asp Gly Leu Leu Cys Cys Leu
145                 150                 155                 160

CTC AAG CGT GTG CTT GAC TCC TGG AAC CTG CCT GCT CCC TCT CCC AGA       528
Leu Lys Arg Val Leu Asp Ser Trp Asn Leu Pro Ala Pro Ser Pro Arg
                165                 170                 175

CCA GCT AGT TTG GGG CTG GGG AGC TCA GGC AAA AGA GGT TTC CAG GAT       576
Pro Ala Ser Leu Gly Leu Gly Ser Ser Gly Lys Arg Gly Phe Gln Asp
            180                 185                 190

GCA GAT TAG GTC ATG CAG GCC TTT ACC GGC ATT GAT GTG GCT CAT GTT       624
Ala Asp     Val Met Gln Ala Phe Thr Gly Ile Asp Val Ala His Val
        195                 200                 205

TCA GGC AGA CTT GGG GTC CTT AAG GTG GCA AGT CCT TTA TGG AGA GAA       672
Ser Gly Arg Leu Gly Val Leu Lys Val Ala Ser Pro Leu Trp Arg Glu
    210                 215                 220

AAC TTG ACA TTC AGA TGA TTG TTT TTA AAT GTT TTA CTT TTG GTA CAG       720
Asn Leu Thr Phe Arg     Leu Phe Leu Asn Val Leu Leu Leu Val Gln
225                 230                 235                 240

TTG ATA GAC ATC ATA AAC GAT ATC AAG CTT ACA CTT CAT ATG GAG TTA       768
Leu Ile Asp Ile Ile Asn Asp Ile Lys Leu Thr Leu His Met Glu Leu
                245                 250                 255

AAC TTG GTC AGT GTT AAT AAA ATC AAA ACG TGA TTC TAC TGT ACA TTG       816
Asn Leu Val Ser Val Asn Lys Ile Lys Thr     Phe Tyr Cys Thr Leu
            260                 265                 270

CAT TAT TCA TAA TTT AAT TGT TTG AAA TTA CAT TAA ATA AAT CAA CTA       864
His Tyr Ser     Phe Asn Cys Leu Lys Leu His     Ile Asn Gln Leu
        275                 280                 285

ATT AAA AAA AAA AAA AAA                                               885
Ile Lys Lys Lys Lys Lys
290                 295
```

(2) INFORMATION FOR SEQ ID NO: 8:

(i) SEQUENCE CHARACTERISTICS:
        (A) LENGTH: 201
        (B) TYPE: nucleic acid
        (C) STRANDEDNESS: double
        (D) TOPOLOGY: linear (xi) SEQUENCE DESCRIPTION: SEQ ID NO: 8:

```
TCG CTC GTG CTC GCC CGC GCC TGG CCT ACC GCG GCA CTC CCG GCT GCA      48
Ser Leu Val Leu Ala Arg Ala Trp Pro Thr Ala Ala Leu Pro Ala Ala
 1               5                  10                  15

CGC TCT GCT TGG CCT CGC ATG CCG GTG GAC CTC AGC AAG TGG TCC GGG      96
Arg Ser Ala Trp Pro Arg Met Pro Val Asp Leu Ser Lys Trp Ser Gly
                20                  25                  30

CCC TTG AGC CTG CAA GAA GTG GAC GAG CAG CCG CAG CAC CCG CTG CAT     144
Pro Leu Ser Leu Gln Glu Val Asp Glu Gln Pro Gln His Pro Leu His
            35                  40                  45

GTC ACC TAC GCC GGG GCG CGT GGA CGA GCT GGG CAA CGT GCT GAC GCC     192
Val Thr Tyr Ala Gly Ala Arg Gly Arg Ala Gly Gln Arg Ala Asp Ala
        50                  55                  60

CAC CCA GGT                                                          201
His Pro Gly
65
```

(2) INFORMATION FOR SEQ ID NO: 9:

(i) SEQUENCE CHARACTERISTICS:
        (A) LENGTH: 237
        (B) TYPE: nucleic acid
        (C) STRANDEDNESS: double
        (D) TOPOLOGY: linear (xi) SEQUENCE DESCRIPTION: SEQ ID NO: 9:

```
TCT CAA GAG ACT GAA CAG AGA TGT GAA TCT CTG AAC ACA AGA ACA GTT      48
Ser Gln Glu Thr Glu Gln Arg Cys Glu Ser Leu Asn Thr Arg Thr Val
 1               5                  10                  15

TAT TTT TCT GAA CAG TGG GTA TCT TCC TTA AAT GAA AGG GAA CAG GAA      96
Tyr Phe Ser Glu Gln Trp Val Ser Ser Leu Asn Glu Arg Glu Gln Glu
                20                  25                  30

CTT CAC AAC TTA TTG GAG GTT GTA AGC CAA TGT TGT GAG GCT TCA AGT     144
Leu His Asn Leu Leu Glu Val Val Ser Gln Cys Cys Glu Ala Ser Ser
            35                  40                  45

TCA GAC ATC ACT GAG AAA TCA GAT GGA CGT AAG GCA GCT CAT GAG AAA     192
Ser Asp Ile Thr Glu Lys Ser Asp Gly Arg Lys Ala Ala His Glu Lys
        50                  55                  60

CAG CAT AAC ATT TTT CTT GAT CAG ATG ACT ATT GAT GAA GAT AAA         237
Gln His Asn Ile Phe Leu Asp Gln Met Thr Ile Asp Glu Asp Lys
65                  70                  75
```

(2) INFORMATION FOR SEQ ID NO: 10:

(i) SEQUENCE CHARACTERISTICS:
        (A) LENGTH: 126
        (B) TYPE: nucleic acid
        (C) STRANDEDNESS: double
        (D) TOPOLOGY: linear (xi) SEQUENCE DESCRIPTION: SEQ ID NO: 10:

```
GAA GAT CAA GAT ACC TCA AAG AAT TCT AAG CTA AAC TCA CAC CAG AAA      48
Glu Asp Gln Asp Thr Ser Lys Asn Ser Lys Leu Asn Ser His Gln Lys
 1               5                  10                  15

GTA ACA CTT CTT CAA TTG CTA CTT GGC CAT AAG AAT GAA GAA AAT GTA      96
Val Thr Leu Leu Gln Leu Leu Leu Gly His Lys Asn Glu Glu Asn Val
                20                  25                  30
```

```
GAA AAA AAC ACC AGC TGC AGG TGA TGA TGA                              126
Glu Lys Asn Thr Ser Cys Arg
         35                  40
```

(2) INFORMATION FOR SEQ ID NO: 11:

(i) SEQUENCE CHARACTERISTICS:
        (A) LENGTH:         570
        (B) TYPE:           nucleic acid
        (C) STRANDEDNESS:  double
        (D) TOPOLOGY:      linear (xi) SEQUENCE DESCRIPTION: SEQ ID NO: 11:

```
CTT ACC TTA GAA AAC CAA ATT AAA GAA GAA AGA GAA CAA GAC AAC TCT       48
Leu Thr Leu Glu Asn Gln Ile Lys Glu Glu Arg Glu Gln Asp Asn Ser
1               5                   10                  15

GAA TCT CCA AAT GGC AGA ACA TCA CCT CTT GTG TCC CAG AAT AAT GAA       96
Glu Ser Pro Asn Gly Arg Thr Ser Pro Leu Val Ser Gln Asn Asn Glu
            20                  25                  30

CAA GGC TCA ACC TTA CGG GAT TTG CTG ACT ACA ACA GCT GGA AAG CTA      144
Gln Gly Ser Thr Leu Arg Asp Leu Leu Thr Thr Thr Ala Gly Lys Leu
         35                  40                  45

CGT GTG GGG TCT ACA GAT GCT GGC ATT GCC TTT GCC CCA GTA TAT GCA      192
Arg Val Gly Ser Thr Asp Ala Gly Ile Ala Phe Ala Pro Val Tyr Ala
 50                  55                  60

ATG GGA GCC CCA AGT AGC AAA AGT GGA CGG ACT ATG CCT AAC ATT CTT      240
Met Gly Ala Pro Ser Ser Lys Ser Gly Arg Thr Met Pro Asn Ile Leu
65                  70                  75                  80

GAT GAC ATA ATT GCT TCA GTT GTT GAA AAC AAA ATT CCA CCA AGT AAA      288
Asp Asp Ile Ile Ala Ser Val Val Glu Asn Lys Ile Pro Pro Ser Lys
                 85                  90                  95

ACC TCC AAG ATA AAT GTA AAA CCA GAG CTT AAA GAA GAG CCT GAA GAA      336
Thr Ser Lys Ile Asn Val Lys Pro Glu Leu Lys Glu Glu Pro Glu Glu
            100                 105                 110

AGC ATA ATA TCT GCA GTG GAT GAA AAT AAT AAA TTA TAC AGT GAT ATA      384
Ser Ile Ile Ser Ala Val Asp Glu Asn Asn Lys Leu Tyr Ser Asp Ile
        115                 120                 125

CCA CAT TCT TGG ATC TGT GAG AAG CAT ATT TTA TGG CTT AGG ATT ATA      432
Pro His Ser Trp Ile Cys Glu Lys His Ile Leu Trp Leu Arg Ile Ile
    130                 135                 140

AGA ATA GCA GTA ATT GGA AGC TTT TCA AAG AAT GTT GGA AAC AAG GAC      480
Arg Ile Ala Val Ile Gly Ser Phe Ser Lys Asn Val Gly Asn Lys Asp
145                 150                 155                 160

AGC CTG CAG TGG TTT CTG GTG TGC ATA AGA AAA TGA ACA TTA GCC TAT      528
Ser Leu Gln Trp Phe Leu Val Cys Ile Arg Lys     Thr Leu Ala Tyr
                165                 170                 175

GGA AGG CGG AAT CAA TTA GTC TTG ATT TTG GAG ACC ACC AAG              570
Gly Arg Arg Asn Gln Leu Val Leu Ile Leu Glu Thr Thr Lys
            180                 185                 190
```

(2) INFORMATION FOR SEQ ID NO: 12:

(i) SEQUENCE CHARACTERISTICS:
        (A) LENGTH:         624
        (B) TYPE:           nucleic acid
        (C) STRANDEDNESS:  double
        (D) TOPOLOGY:      linear (xi) SEQUENCE DESCRIPTION: SEQ ID NO: 12:

```
AAC CAT ACC CCT GGC GCC TTG TAC CCC GAT TCC GAC TTG GAG AAG GAA       48
Asn His Thr Pro Gly Ala Leu Tyr Pro Asp Ser Asp Leu Glu Lys Glu
1               5                   10                  15

GAA GAG GAG AGT GAG GAG GAC TGG AAG CTG CAG CTG GAG GCT GAA AAC       96
Glu Glu Glu Ser Glu Glu Asp Trp Lys Leu Gln Leu Glu Ala Glu Asn
```

```
                    20                    25                    30
TAC GAG GGC CAC ACC CCA CTC CAC GTG GCC GTT ATC CAC AAA GAT GTG         144
Tyr Glu Gly His Thr Pro Leu His Val Ala Val Ile His Lys Asp Val
         35                    40                    45

GAG ATG GTC CGG CTG CTC CGA GAT GCT GGA GCT GAC CTT GAC AAA CCG         192
Glu Met Val Arg Leu Leu Arg Asp Ala Gly Ala Asp Leu Asp Lys Pro
     50                    55                    60

GAG CCC ACG TGC GGC CGG AGC CCC TTC ATT TGG CAG TGG AGG CCA GGC         240
Glu Pro Thr Cys Gly Arg Ser Pro Phe Ile Trp Gln Trp Arg Pro Gly
 65                    70                    75                    80

AGC CGA TGT GCT GGA GCT TCT CTG AGG GCA GGC GCG AAC CCT GCT GCC         288
Ser Arg Cys Ala Gly Ala Ser Leu Arg Ala Gly Ala Asn Pro Ala Ala
                 85                    90                    95

CGC ATG TAC GGT GGC CGC ACC CCA CTC GGC AGT GCC ATG CTC CGG CCC         336
Arg Met Tyr Gly Gly Arg Thr Pro Leu Gly Ser Ala Met Leu Arg Pro
             100                   105                   110

AAC CCC ATC CTC GCC CGC CTC CTC CGT GCA CAC GGA GCC CCT GAG CCC         384
Asn Pro Ile Leu Ala Arg Leu Leu Arg Ala His Gly Ala Pro Glu Pro
         115                   120                   125

GAG GGG AAG GAC GAG AAA TCC GGC CCC TGC AGC AGC AGT AGC GAG CAC         432
Glu Gly Lys Asp Glu Lys Ser Gly Pro Cys Ser Ser Ser Ser Glu His
 130                   135                   140

GAC NAG AGA NGA CGA GGG CGA TGA ATA CGA CGA CAT TGT GGT TCA CAG         480
Asp Xaa Arg Xaa Arg Gly Arg     Ile Arg Arg His Cys Gly Ser Gln
145                   150                   155                   160

CAG CCG CAG CCA AAC CCG GCT GCC TCC CAC CCC AGC CTC AAA ACC TCT         528
Gln Pro Gln Pro Asn Pro Ala Ala Ser His Pro Ser Leu Lys Thr Ser
                 165                   170                   175

TCC TGA CGA CCC CCG CCC CGT GTG ATT TGT TTC ATT GTT AAT ATA ATT         576
Ser     Arg Pro Pro Pro Arg Val Ile Cys Phe Ile Val Asn Ile Ile
             180                   185                   190

TCC AGT TTA ATA AAC AAA ACC CTA GTT CTG ACA ACC AGA AAA AAA AAA         624
Ser Ser Leu Ile Asn Lys Thr Leu Val Leu Thr Thr Arg Lys Lys Lys
         195                   200                   205
```

(2) INFORMATION FOR SEQ ID NO:    13:

(i) SEQUENCE CHARACTERISTICS:
        (A) LENGTH:            99
        (B) TYPE:              nucleic acid
        (C) STRANDEDNESS:      double
        (D) TOPOLOGY:          linear (xi) SEQUENCE DESCRIPTION: SEQ ID NO: 13:

```
AGA CAC CCG CTG ATC AGA GAC ATG CTT CGA CGA ATT AAG GAA GAA GAG          48
Arg His Pro Leu Ile Arg Asp Met Leu Arg Arg Ile Lys Glu Glu Glu
 1               5                   10                  15

GAT CTG GGT AAA AGT AGA GAA GGA TCA AGG ACG GAT GAT GAA GTA GTA          96
Asp Leu Gly Lys Ser Arg Glu Gly Ser Arg Thr Asp Asp Glu Val Val
             20                  25                  30

CAG                                                                      99
Gln
```

(2) INFORMATION FOR SEQ ID NO:    14:

(i) SEQUENCE CHARACTERISTICS:
        (A) LENGTH:            216
        (B) TYPE:              nucleic acid
        (C) STRANDEDNESS:      double
        (D) TOPOLOGY:          linear (xi) SEQUENCE DESCRIPTION: SEQ ID NO: 14:

```
CAG GTG GAA GAA AAC ACC CCG TAC TGG CAG GCA TGG AGC CAA CAA GGA          48
```

```
    Gln Val Glu Glu Asn Thr Pro Tyr Trp Gln Ala Trp Ser Gln Gln Gly
    1               5                   10                  15

GAA CCT GGA GCT CAA CGG CAG CAT CCT GAG TGC GAG AAC TTT CAA AGG         96
Glu Pro Gly Ala Gln Arg Gln His Pro Glu Cys Glu Asn Phe Gln Arg
            20                  25                  30

CTT CCA AAT CTG ATG CTA CTT CTG GAA TCC TCA ATT CAA CCA ACA TCC         144
Leu Pro Asn Leu Met Leu Leu Leu Glu Ser Ser Ile Gln Pro Thr Ser
                35                  40                  45

AGT CCT GAG AAG CCC TGA TCA GTC AAC CAG CTG TGG CTT CCT GTG CCT         192
Ser Pro Glu Lys Pro     Ser Val Asn Gln Leu Trp Leu Pro Val Pro
            50              55                  60

AGA CTG GAC CTA ATT ATA TGG GGG                                         216
Arg Leu Asp Leu Ile Ile Trp Gly
65                  70

(2) INFORMATION FOR SEQ ID NO:     15:

(i) SEQUENCE CHARACTERISTICS:
            (A) LENGTH:                 634
            (B) TYPE:                   nucleic acid
            (C) STRANDEDNESS:           double
            (D) TOPOLOGY:               linear (xi) SEQUENCE DESCRIPTION: SEQ ID NO: 15:

TGC CGC TGC AGC AGC GCA GTT CCA GTC CGT TGC TTT ACT TTT TGC TTC         48
Cys Arg Cys Ser Ser Ala Val Pro Val Arg Cys Phe Thr Phe Cys Phe
1               5                   10                  15

ACC GAC ATA GTC ATT ATG CCG AAG AGA AAG TCT CCA GAG AAT ACA GAG         96
Thr Asp Ile Val Ile Met Pro Lys Arg Lys Ser Pro Glu Asn Thr Glu
                20                  25                  30

GGC AAA GAT GGA TCC AAA GTA ACT AAA CAG GAG CCC ACA AGA CGG TCT         144
Gly Lys Asp Gly Ser Lys Val Thr Lys Gln Glu Pro Thr Arg Arg Ser
                35                  40                  45

GCC AGA TTG TCA GCG AAA CCT GCT CCA CCA AAA CCT GAA CCC AAA CCA         192
Ala Arg Leu Ser Ala Lys Pro Ala Pro Pro Lys Pro Glu Pro Lys Pro
            50                  55                  60

AGA AAA ACA TCT GCT AAG AAA GAA CCT GGA GCA AAG ATT AGC AGA GGT         240
Arg Lys Thr Ser Ala Lys Lys Glu Pro Gly Ala Lys Ile Ser Arg Gly
65                  70                  75                  80

GCT AAA GGG AGG AAG GAG GAA AAG CAG GAA GCT GGA AAG GAA GGT ACT         288
Ala Lys Gly Arg Lys Glu Glu Lys Gln Glu Ala Gly Lys Glu Gly Thr
                85                  90                  95

GCA CCA TCT GAA AAT GGT GAA ACT AAA GCT GAA GAG GCA CAG AAA ACT         336
Ala Pro Ser Glu Asn Gly Glu Thr Lys Ala Glu Glu Ala Gln Lys Thr
                100                 105                 110

GAA TCT GTA GAT AAC GAG GGA GAA TGA ATT GTC ATG AAA AAT TGG GGT         384
Glu Ser Val Asp Asn Glu Gly Glu     Ile Val Met Lys Asn Trp Gly
            115                 120                 125

TGA TTT TAT GTA TCT CTT GGG ACA ACT TTT AAA AGC TAT TTT TAC CAA         432
    Phe Tyr Val Ser Leu Gly Thr Thr Phe Lys Ser Tyr Phe Tyr Gln
    130                 135                 140

GTA TTT TGT AAA TGC TAA TTT TTT AGG ACT CTA CTA GTT GGC ATA CGA         480
Val Phe Cys Lys Cys     Phe Phe Arg Thr Leu Leu Val Gly Ile Arg
145                 150                 155                 160

AAA TAT ATA AGG ATG GAC ATT TAT CGT CTC ATA GTC ATG CTT TTT GGA         528
Lys Tyr Ile Arg Met Asp Ile Tyr Arg Leu Ile Val Met Leu Phe Gly
                165                 170                 175

ATT TNN NNN NNN NNN NNN NNN NNN NNN NCA GGA AGT TTG CCC CAA             576
Ile Xaa Xaa Xaa Xaa Xaa Xaa Xaa Xaa Xaa Gly Ser Leu Pro Gln
                180                 185                 190

GAT GCT CAG TGT GCC GTG GGG CCA TAA CTG CCT GAG CCA GGT CAG GAG         624
Asp Ala Gln Cys Ala Val Gly Pro     Leu Pro Glu Pro Gly Gln Glu
```

```
                195                 200                  205
GAG ACT GCT G                                                                634
Glu Thr Ala
        210

(2) INFORMATION FOR SEQ ID NO:    16:

(i) SEQUENCE CHARACTERISTICS:
        (A) LENGTH:            638
        (B) TYPE:              nucleic acid
        (C) STRANDEDNESS:      double
        (D) TOPOLOGY:          linear (xi) SEQUENCE DESCRIPTION: SEQ ID NO: 16:

AAA CAT CCT ATC ATC TGT AGG CTC ATT CAT TTC TCT AAC AGC AGC AGC               48
Lys His Pro Ile Ile Cys Arg Leu Ile His Phe Ser Asn Ser Ser Ser
1                5                  10                  15

AAC AGC GCA TCA CAG GAC ACC AAG GAG AGC TCT GAA GAG CCT CCC TCA               96
Asn Ser Ala Ser Gln Asp Thr Lys Glu Ser Ser Glu Glu Pro Pro Ser
                20                  25                  30

GAA GAG AGC CAG GAC ACC CCC ATT TAC ACG GAG TTT GAT GAG GAT TTC              144
Glu Glu Ser Gln Asp Thr Pro Ile Tyr Thr Glu Phe Asp Glu Asp Phe
            35                  40                  45

GAG GAG GAA CCC ACA TCC CCC ATA GGT CAC TGT GTG GCC ATC TAC CAC              192
Glu Glu Glu Pro Thr Ser Pro Ile Gly His Cys Val Ala Ile Tyr His
        50                  55                  60

TTT GAA GGG TCC AGC GAG GGC ACT ATC TCT ATG GCC GAG GGT GAA GAC              240
Phe Glu Gly Ser Ser Glu Gly Thr Ile Ser Met Ala Glu Gly Glu Asp
65                  70                  75                  80

CTC AGT CTT ATG GAA GAA GAC AAA GGG GAC GGC TGG ACC CGG GTC AGG              288
Leu Ser Leu Met Glu Glu Asp Lys Gly Asp Gly Trp Thr Arg Val Arg
                85                  90                  95

CGG AAA GAG GGA GGC GAG GGC TAC GTG CCC ACC TCC TAC CTC CGA GTC              336
Arg Lys Glu Gly Gly Glu Gly Tyr Val Pro Thr Ser Tyr Leu Arg Val
            100                 105                 110

ACG CTC AAT TGA ACC CTG CCA GAG ACG GGA AGA GGG GGG CTG TCG GCT              384
Thr Leu Asn     Thr Leu Pro Glu Thr Gly Arg Gly Gly Leu Ser Ala
        115                 120                 125

GCT GCT TCT GGG CCA CGG GGA GCC CCA GGA CCT ATG CAC TTT ATT TCT              432
Ala Ala Ser Gly Pro Arg Gly Ala Pro Gly Pro Met His Phe Ile Ser
130                 135                 140

GAC CCC GTG GCT TCG GCT GAG ACC TGT GTA ACC TGC TGC CCC CTC CAC              480
Asp Pro Val Ala Ser Ala Glu Thr Cys Val Thr Cys Cys Pro Leu His
145                 150                 155                 160

CCC CAA CCC AGT CCT ACC TGT CAC ACC GGA CGG ACC CGC TGT GCC TTC              528
Pro Gln Pro Ser Pro Thr Cys His Thr Gly Arg Thr Arg Cys Ala Phe
                165                 170                 175

TAC CAT CGT TCC ACC ATT GAT GTA CAT ACT CAT GTT TTA CAT CTT TTC              576
Tyr His Arg Ser Thr Ile Asp Val His Thr His Val Leu His Leu Phe
            180                 185                 190

TTT CTG CGC TCG GCT CCG GCC ATT TTG TTT TAT ACA AAA ATG GGA AAA              624
Phe Leu Arg Ser Ala Pro Ala Ile Leu Phe Tyr Thr Lys Met Gly Lys
        195                 200                 205

AAA AAA AAA AAA AA                                                           638
Lys Lys Lys Lys
        210

(2) INFORMATION FOR SEQ ID NO:    17:

(i) SEQUENCE CHARACTERISTICS:
        (A) LENGTH:            862
        (B) TYPE:              nucleic acid
        (C) STRANDEDNESS:      double
```

(D) TOPOLOGY: linear (xi) SEQUENCE DESCRIPTION: SEQ ID NO: 17:

```
GGC ACG AGG CGT GAC GTC CGA CAA GAA ATG CTG GAT GAT GTA CAA AAG        48
Gly Thr Arg Arg Asp Val Arg Gln Glu Met Leu Asp Asp Val Gln Lys
1               5                  10                  15

AAA TTG ATG AGC TTA GCA AAC AGC TCA GAA GGA AAA GTA GAC AAA GTC        96
Lys Leu Met Ser Leu Ala Asn Ser Ser Glu Gly Lys Val Asp Lys Val
            20                  25                  30

CTA ATG AGA AAC CTC TTC ATT GGT CAT TTC CAC ACA CCG AAA AAT CAG       144
Leu Met Arg Asn Leu Phe Ile Gly His Phe His Thr Pro Lys Asn Gln
        35                  40                  45

CGT CAT GAA GTG TTA CGG TTA ATG GGG AGC ATC CTG GGC GTC AGA AGG       192
Arg His Glu Val Leu Arg Leu Met Gly Ser Ile Leu Gly Val Arg Arg
50                  55                  60

GAG GAG ATG GAG CAG TTG TTT CAT GAC GAT CAG GGC AGT GTT ACC AGG       240
Glu Glu Met Glu Gln Leu Phe His Asp Asp Gln Gly Ser Val Thr Arg
65                  70                  75                  80

TGG ATG ACT GGG TGG CTT GGA GGA GGA TCA AAA AGT GTT CCC AAC ACA       288
Trp Met Thr Gly Trp Leu Gly Gly Gly Ser Lys Ser Val Pro Asn Thr
                85                  90                  95

CCT TTG AGA CCA AAT CAG CAA TCT GTG GTT AAT AGT TCT TTT TCA GAA       336
Pro Leu Arg Pro Asn Gln Gln Ser Val Val Asn Ser Ser Phe Ser Glu
            100                 105                 110

CTT TTT GTT AAA TTT CTA GAA ACA GAA TCT CAT CCA TCC ATT CCA CCA       384
Leu Phe Val Lys Phe Leu Glu Thr Glu Ser His Pro Ser Ile Pro Pro
        115                 120                 125

CCA AAG CTT TCT GTT CAT GAT ATG AAA CCT CTG GAT TCA CCA GGA AGA       432
Pro Lys Leu Ser Val His Asp Met Lys Pro Leu Asp Ser Pro Gly Arg
    130                 135                 140

AGA AAA AGA GAT ACA AAT GCA CCA GAA AGT TTT AAA GAT ACA GCA GAA       480
Arg Lys Arg Asp Thr Asn Ala Pro Glu Ser Phe Lys Asp Thr Ala Glu
145                 150                 155                 160

TCC AGG TCT GGT AGA AGA ACA GAT GTA AAT CCG TTT TTG GCT CCT CGC       528
Ser Arg Ser Gly Arg Arg Thr Asp Val Asn Pro Phe Leu Ala Pro Arg
                165                 170                 175

TCG GCA GCT GTA CCT CTT ATT AAC CCA GCT GGA CTT GGA CCT GGT GGG       576
Ser Ala Ala Val Pro Leu Ile Asn Pro Ala Gly Leu Gly Pro Gly Gly
            180                 185                 190

CCG GGC ATC TTC TTC TGA AAC CCA TCT CAG ATG TTT TGC CCA CAT TTA       624
Pro Gly Ile Phe Phe     Asn Pro Ser Gln Met Phe Cys Pro His Leu
        195                 200                 205

CAC CTT TGC CAG CGT TAC CTG ACA ACA GTG CTG GGG TTG TGC TGA AAG       672
His Leu Cys Gln Arg Tyr Leu Thr Thr Val Leu Gly Leu Cys     Lys
    210                 215                 220

CCT TTT AAA GCA ATA GAT GAT TCT CAA GCC AGA GAC AAT CTA GCA CTT       720
Pro Phe Lys Ala Ile Asp Asp Ser Gln Ala Arg Asp Asn Leu Ala Leu
225                 230                 235                 240

TAA AGA AAC CAT GAA CAC TAT ATG TAT GTA CTT TAT CAC AAA GTG GCC       768
    Arg Asn His Glu His Tyr Met Tyr Val Leu Tyr His Lys Val Ala
                245                 250                 255

TTT GGG GAG AAA GTC ATG TAT TTG TTC GCA ATT ATG CTT TCT CTG AAT       816
Phe Gly Glu Lys Val Met Tyr Leu Phe Ala Ile Met Leu Ser Leu Asn
            260                 265                 270

TTA ATA AAA ATA TTC CTA ATG CTT TTA GAA AAA AAA AAA AAA A             862
Leu Ile Lys Ile Phe Leu Met Leu Leu Glu Lys Lys Lys Lys Lys
        275                 280                 285
```

(2) INFORMATION FOR SEQ ID NO: 18:

(i) SEQUENCE CHARACTERISTICS:

```
        (A) LENGTH:            247
        (B) TYPE:              nucleic acid
        (C) STRANDEDNESS:      double
        (D) TOPOLOGY:          linear (xi) SEQUENCE DESCRIPTION: SEQ ID NO: 18:

GGC ACG AGG CGA GTT CTC CCA CCT GAG CAG AAA TAT GAC CAT GCA GCG      48
Gly Thr Arg Arg Val Leu Pro Pro Glu Gln Lys Tyr Asp His Ala Ala
1               5                   10                  15

CAC CAT GAA GCT CTA CCG ACT GCC AGA GAC TCC CAA GAC AGC TGG GCT      96
His His Glu Ala Leu Pro Thr Ala Arg Asp Ser Gln Asp Ser Trp Ala
                20                  25                  30

GCG ACC AAT GGA AAC AAA GGA CAT TCC AGT AGT GCA CCA GCT CCT CAC     144
Ala Thr Asn Gly Asn Lys Gly His Ser Ser Ser Ala Pro Ala Pro His
            35                  40                  45

CAG GTA CTT GAA GCA ATT TCA CCT TAC GCC CGT CAT GAG CCA GGA GGA     192
Gln Val Leu Glu Ala Ile Ser Pro Tyr Ala Arg His Glu Pro Gly Gly
        50                  55                  60

GGT GGA GCA CTG GTT CTA CCC CCA GGA GAA TAT CAT CGA CAC TTT CGT     240
Gly Gly Ala Leu Val Leu Pro Pro Gly Glu Tyr His Arg His Phe Arg
65                  70                  75                  80

GGT GGA G                                                           247
Gly Gly (2) INFORMATION FOR SEQ ID NO:    19:

(i) SEQUENCE CHARACTERISTICS:
        (A) LENGTH:            102
        (B) TYPE:              nucleic acid
        (C) STRANDEDNESS:      double
        (D) TOPOLOGY:          linear (xi) SEQUENCE DESCRIPTION: SEQ ID NO: 19:

AGG GCG CAC CTG GAG CTG TTC TGG TCT AGA GTG AAT ATC CCC AAG GTG      48
Arg Ala His Leu Glu Leu Phe Trp Ser Arg Val Asn Ile Pro Lys Val
1               5                   10                  15

CTA AGA GCT GCA GAA CAA GCT CAT CTT TGG GCA GAC TGG TGT TTT TGT      96
Leu Arg Ala Ala Glu Gln Ala His Leu Trp Ala Asp Trp Cys Phe Cys
                20                  25                  30

ATG ACA                                                             102
Met Thr (2) INFORMATION FOR SEQ ID NO:    20:

(i) SEQUENCE CHARACTERISTICS:
        (A) LENGTH:            219
        (B) TYPE:              nucleic acid
        (C) STRANDEDNESS:      double
        (D) TOPOLOGY:          linear (xi) SEQUENCE DESCRIPTION: SEQ ID NO: 20:

GTT AGC TCT AGA GGC CAT TCT TTT GCT GAT CCT GCC AGT AAT CTT GGG      48
Val Ser Ser Arg Gly His Ser Phe Ala Asp Pro Ala Ser Asn Leu Gly
1               5                   10                  15

CTG GAA GAC ATT ATC AGG AAG GCT CTC ATG GGA AGC TTT GAT GAC AAA      96
Leu Glu Asp Ile Ile Arg Lys Ala Leu Met Gly Ser Phe Asp Asp Lys
                20                  25                  30

GTT GAG GAT CAT GGA GTT GTC ATG TCC CAG CCT ATG GGA GTA GTG CCT     144
Val Glu Asp His Gly Val Val Met Ser Gln Pro Met Gly Val Val Pro
            35                  40                  45

GGT ACT GCC AAC ACC GAT TGC ATG TGC TCC CTC TGC GGT GAA CCA AGC     192
Gly Thr Ala Asn Thr Asp Cys Met Cys Ser Leu Cys Gly Glu Pro Ser
        50                  55                  60

AGC TCC TCA CCA ACA GAA CAG GAT CTG                                 219
```

```
Ser Ser Ser Pro Thr Glu Gln Asp Leu
 65                  70
```

(2) INFORMATION FOR SEQ ID NO:     21:

(i) SEQUENCE CHARACTERISTICS:
        (A) LENGTH:            553
        (B) TYPE:              nucleic acid
        (C) STRANDEDNESS:      double
        (D) TOPOLOGY:          linear (xi) SEQUENCE DESCRIPTION: SEQ ID NO: 21:

```
AAT ATC GAA CTG AAG AAA GGA GGG AAG GAT ATA CCA GTC ACT ATC CAC        48
Asn Ile Glu Leu Lys Lys Gly Gly Lys Asp Ile Pro Val Thr Ile His
 1               5                  10                  15

AAT TTA GAG GAG TAT CTA AGA CTG GTT ATA TTC TGG GCA CTA AAT GAA        96
Asn Leu Glu Glu Tyr Leu Arg Leu Val Ile Phe Trp Ala Leu Asn Glu
             20                  25                  30

GGC GTT TCT AGG CAA TTT GAT TCG TTC AGA GAT GGA TTT GAA TCA GTC       144
Gly Val Ser Arg Gln Phe Asp Ser Phe Arg Asp Gly Phe Glu Ser Val
         35                  40                  45

TTC CCA CTC AGT CAT CTT CAG TAC TTC TAC CCG GAG GAA CTG GAT CAG       192
Phe Pro Leu Ser His Leu Gln Tyr Phe Tyr Pro Glu Glu Leu Asp Gln
 50                  55                  60

CTC CTT TGT GGC AGT AAA GCA GAC ACT TGG GAT GCA AAG ACA CTG ATG       240
Leu Leu Cys Gly Ser Lys Ala Asp Thr Trp Asp Ala Lys Thr Leu Met
 65                  70                  75                  80

GAA TGC TGT AGG CCT GAT CAT GGT TAT ACT CAT GAC AGT CGG GCT GTG       288
Glu Cys Cys Arg Pro Asp His Gly Tyr Thr His Asp Ser Arg Ala Val
                 85                  90                  95

AAG TTT TTG TTT GAG ATT CTC AGT AGT TTT GAT AAT GAG CAG CAG AGG       336
Lys Phe Leu Phe Glu Ile Leu Ser Ser Phe Asp Asn Glu Gln Gln Arg
            100                 105                 110

TTA TTT CTC CAG TTT GTG ACT GGT AGC CCA AGA TTG CCT GTT GGA GGA       384
Leu Phe Leu Gln Phe Val Thr Gly Ser Pro Arg Leu Pro Val Gly Gly
        115                 120                 125

TTC CGG AGT TTG AAT CCA CCT TTG ACA ATT GTC CGA AAG ACG TTT GAA       432
Phe Arg Ser Leu Asn Pro Pro Leu Thr Ile Val Arg Lys Thr Phe Glu
    130                 135                 140

TCA ACA GAA AAC CCA GAT GAC TTC TTG CCC TCT GTA ATG ACT TGT GTG       480
Ser Thr Glu Asn Pro Asp Asp Phe Leu Pro Ser Val Met Thr Cys Val
145                 150                 155                 160

AAC TAT CTT AAG TTG CCG GAC TAT CAA GCA TTG AGA TAT GCG TGA AAA       528
Asn Tyr Leu Lys Leu Pro Asp Tyr Gln Ala Leu Arg Tyr Ala     Lys
                165                 170                 175

ACT GTT GAT AGC AGC AAG AGA AGG G                                     553
Thr Val Asp Ser Ser Lys Arg Arg
            180
```

(2) INFORMATION FOR SEQ ID NO:     22:

(i) SEQUENCE CHARACTERISTICS:
        (A) LENGTH:            186
        (B) TYPE:              nucleic acid
        (C) STRANDEDNESS:      double
        (D) TOPOLOGY:          linear (xi) SEQUENCE DESCRIPTION: SEQ ID NO: 22:

```
GAA GCA AAA AAC GAG CCC TGG AAG AAG AAA AAC CAC GCC GGG AAA TCC        48
Glu Ala Lys Asn Glu Pro Trp Lys Lys Lys Asn His Ala Gly Lys Ser
 1               5                  10                  15

TGG AAA AAC GAT TAC AGG AAG AAA CTA GCC AGA GGA GAA GTT AAT AGA        96
Trp Lys Asn Asp Tyr Arg Lys Lys Leu Ala Arg Gly Glu Val Asn Arg
             20                  25                  30
```

```
AAA GGA AGT AAA AAT AAG GGA GAG ACA AAG GGC ACA GGC TCG TCC TTT      144
Lys Gly Ser Lys Asn Lys Gly Glu Thr Lys Gly Thr Gly Ser Ser Phe
         35                  40                  45

GAC ACG CTA CCT GCC TGT CCG GAA GAA GAC TTT GAT TTG CGG              186
Asp Thr Leu Pro Ala Cys Pro Glu Glu Asp Phe Asp Leu Arg
 50                  55                  60
```

(2) INFORMATION FOR SEQ ID NO:     23:

(i) SEQUENCE CHARACTERISTICS:
        (A) LENGTH:              66
        (B) TYPE:                nucleic acid
        (C) STRANDEDNESS:        double
        (D) TOPOLOGY:            linear (xi) SEQUENCE DESCRIPTION: SEQ ID NO: 23:

```
AGG GTA CGG GAA GCT GCT GAA AAG GCT AAG TCT GAA CTC TCC TCA TCT       48
Arg Val Arg Glu Ala Ala Glu Lys Ala Lys Ser Glu Leu Ser Ser Ser
 1               5                  10                  15

GTG CAG ACT GAC ATC AAT                                               66
Val Gln Thr Asp Ile Asn
             20
```

(2) INFORMATION FOR SEQ ID NO:     24:

(i) SEQUENCE CHARACTERISTICS:
        (A) LENGTH:              192
        (B) TYPE:                nucleic acid
        (C) STRANDEDNESS:        double
        (D) TOPOLOGY:            linear (xi) SEQUENCE DESCRIPTION: SEQ ID NO: 24:

```
CAT TTG AAT ATG AAG TTG ACC CGT GCT CAA TTT GAA GGG ATT GTC ACT       48
His Leu Asn Met Lys Leu Thr Arg Ala Gln Phe Glu Gly Ile Val Thr
 1               5                  10                  15

GAT CTA ATC AGA AGG ACT ATC GCT CCA TGC CAA AAA GCT ATG CAA GAT       96
Asp Leu Ile Arg Arg Thr Ile Ala Pro Cys Gln Lys Ala Met Gln Asp
                 20                  25                  30

GCA GAA GTC AGC AAG AGT GAC ATA GGA GAA GTG ATT CTT GTG GGT GGC      144
Ala Glu Val Ser Lys Ser Asp Ile Gly Glu Val Ile Leu Val Gly Gly
         35                  40                  45

ATG ACT AGG ATG CCC AAG GTT CAG CAG ACT GTA CAG GAC TTT TTG GCA      192
Met Thr Arg Met Pro Lys Val Gln Gln Thr Val Gln Asp Phe Leu Ala
 50                  55                  60
```

(2) INFORMATION FOR SEQ ID NO:     25:

(i) SEQUENCE CHARACTERISTICS:
        (A) LENGTH:              582
        (B) TYPE:                nucleic acid
        (C) STRANDEDNESS:        double
        (D) TOPOLOGY:            linear (xi) SEQUENCE DESCRIPTION: SEQ ID NO: 25:

```
GGG GGC AGT GGA CGA GGC CGT GGC GAC CTG AAG CAG GCG CTT CCC TGT       48
Gly Gly Ser Gly Arg Gly Arg Gly Asp Leu Lys Gln Ala Leu Pro Cys
 1               5                  10                  15

GTG GCC GAG TCG CCA ACG TCC CAC GTG GAG GTG CAT CAG CGC GGC AGC       96
Val Ala Glu Ser Pro Thr Val His Val Glu Val His Gln Arg Gly Ser
                 20                  25                  30

AGC ACT GCA AAG AAA GAA GAC ATA AAC CTG AGT GTT AGA AAG CTA CTC      144
Ser Thr Ala Lys Lys Glu Asp Ile Asn Leu Ser Val Arg Lys Leu Leu
         35                  40                  45

AAC AGA CAT AAT ATT GTG TTT GGC GAT TAC ACA TGG ACT GAG TTT GAT      192
Asn Arg His Asn Ile Val Phe Gly Asp Tyr Thr Trp Thr Glu Phe Asp
```

```
            50                  55                  60
GAA CCT TTT TTG ACC AGA AAT GTG CAG TCT GTG TCT ATT ATT GAC ACA                 240
Glu Pro Phe Leu Thr Arg Asn Val Gln Ser Val Ser Ile Ile Asp Thr
65                  70                  75                  80

GAA TTA AAG GTT AAA GAC TCA CAG CCC ATC GAT TTG AGT GCA TGC ACT                 288
Glu Leu Lys Val Lys Asp Ser Gln Pro Ile Asp Leu Ser Ala Cys Thr
                85                  90                  95

GTT GCA CTT CAC ATT TTC CAG CTG AAT GAA GAT GGC CCC AGC AGT GAA                 336
Val Ala Leu His Ile Phe Gln Leu Asn Glu Asp Gly Pro Ser Ser Glu
            100                 105                 110

AAT CTG GAG GAA GAG ACA GAA AAC ATA ATT GCA GCA AAT CAC TGG GTT                 384
Asn Leu Glu Glu Glu Thr Glu Asn Ile Ile Ala Ala Asn His Trp Val
            115                 120                 125

CTA CCT GCA GCT GAA TTC CAT GGG CTT TGG GAC AGC TTG GTA TAC GAT                 432
Leu Pro Ala Ala Glu Phe His Gly Leu Trp Asp Ser Leu Val Tyr Asp
        130                 135                 140

GTG GAA GTC AAA TCC CAT CTC CTC GAT TAT GTG ATG ACA ACT TTA CTG                 480
Val Glu Val Lys Ser His Leu Leu Asp Tyr Val Met Thr Thr Leu Leu
145                 150                 155                 160

TTT TCA GAC AAG AAC GTC AAC AGC AAC CTC ATC ACC ATA GAG GGG TTC                 528
Phe Ser Asp Lys Asn Val Asn Ser Asn Leu Ile Thr Ile Glu Gly Phe
                165                 170                 175

CTC CAG GCC CTG TCT CTG GCA GTG GAC AAG CAG TTT GAA GAG AGA AAG                 576
Leu Gln Ala Leu Ser Leu Ala Val Asp Lys Gln Phe Glu Glu Arg Lys
            180                 185                 190

AAG CTT                                                                         582
Lys Leu (2) INFORMATION FOR SEQ ID NO:    26:

(i) SEQUENCE CHARACTERISTICS:
          (A) LENGTH:              487
          (B) TYPE:                nucleic acid
          (C) STRANDEDNESS:        double
          (D) TOPOLOGY:            linear (xi) SEQUENCE DESCRIPTION: SEQ ID NO: 26:

TTC ACC ACT GTG ATG GAC CTG CTC CTG GAG TAT GAA GTC ATC TGT ATC                 48
Phe Thr Thr Val Met Asp Leu Leu Leu Glu Tyr Glu Val Ile Cys Ile
1                   5                   10                  15

TAC TGG ACC AAG TAC TAC ACA CTC CAC AAT GCA ATC ATT GAG GAT TGT                 96
Tyr Trp Thr Lys Tyr Tyr Thr Leu His Asn Ala Ile Ile Glu Asp Cys
                20                  25                  30

GTC AGA AAA CAG CTC AAA AAA GAG AGG CCC ATC ATC CTG GAT CCG GCC                 144
Val Arg Lys Gln Leu Lys Lys Glu Arg Pro Ile Ile Leu Asp Pro Ala
            35                  40                  45

GAC CCC ACC CTC AAC GTG GCA GAA GGG TAC AGA TGG GAC ATC GTT GCT                 192
Asp Pro Thr Leu Asn Val Ala Glu Gly Tyr Arg Trp Asp Ile Val Ala
        50                  55                  60

CAG AGG GCC TCC CAG TGC CTG AAA CAG GAC TGT TGC TAT GAC AAC AGG                 240
Gln Arg Ala Ser Gln Cys Leu Lys Gln Asp Cys Cys Tyr Asp Asn Arg
65                  70                  75                  80

GAG AAG GGG ATC TCC AGC TGG AAC GTG AAG AGG GCA CGA GAC ATC CAC                 288
Glu Lys Gly Ile Ser Ser Trp Asn Val Lys Arg Ala Arg Asp Ile His
                85                  90                  95

TTG ACA GTG GAG CAG AGG GGT TAC CCA GAT TTC AAC CTC ATC GTG AAC                 336
Leu Thr Val Glu Gln Arg Gly Tyr Pro Asp Phe Asn Leu Ile Val Asn
            100                 105                 110

CCT TAT GAG CCC ATA AGG AAG GTT AAA GAG AAA ATC CGG AGA CCA GGG                 384
Pro Tyr Glu Pro Ile Arg Lys Val Lys Glu Lys Ile Arg Arg Pro Gly
        115                 120                 125
```

```
GCT ACT CTG GCC TGC AGC GTC TGT CCT TCC AGG TTC CTG GCA GTG AGA       432
Ala Thr Leu Ala Cys Ser Val Cys Pro Ser Arg Phe Leu Ala Val Arg
    130                 135                 140

GGC AGC TTC TCA GCA GCA GGT GCT CCT TAG CCA AAT ATG GGA TCT TCT       480
Gly Ser Phe Ser Ala Ala Gly Ala Pro     Pro Asn Met Gly Ser Ser
145                 150                 155                 160

CCC ACA C                                                             487
Pro Thr
```

(2) INFORMATION FOR SEQ ID NO: 27:

(i) SEQUENCE CHARACTERISTICS:
        (A) LENGTH: 768
        (B) TYPE: nucleic acid
        (C) STRANDEDNESS: double
        (D) TOPOLOGY: linear (xi) SEQUENCE DESCRIPTION: SEQ ID NO: 27:

```
ATG GAG GAT GAT TTC ATG TGC GAT GAT GAG GAG GAC TAC GAC CTG GAA        48
Met Glu Asp Asp Phe Met Cys Asp Asp Glu Glu Asp Tyr Asp Leu Glu
1               5                   10                  15

TAC TCT GAA GAT AGT AAC TCC GAG CCA AAT GTG GAT TTG GAA AAT CAG        96
Tyr Ser Glu Asp Ser Asn Ser Glu Pro Asn Val Asp Leu Glu Asn Gln
                20                  25                  30

TAC TAT AAT TCC AAA GCA TTA AAA GAA GAT GAC CCA AAA GCG GCA TTA       144
Tyr Tyr Asn Ser Lys Ala Leu Lys Glu Asp Asp Pro Lys Ala Ala Leu
            35                  40                  45

AGC AGT TTC CAA AAG GTT TTG GAA CTT GAA GGT GAA AAA GGA GAA TGG       192
Ser Ser Phe Gln Lys Val Leu Glu Leu Glu Gly Glu Lys Gly Glu Trp
50                  55                  60

GGA TTT AAA GCA CTG AAA CAA ATG ATT AAG ATT AAC TTC AAG TTG ACA       240
Gly Phe Lys Ala Leu Lys Gln Met Ile Lys Ile Asn Phe Lys Leu Thr
65                  70                  75                  80

AAC TTT CCA GAA ATG ATG AAT AGA TAT AAG CAG CTA TTG ACC TAT ATT       288
Asn Phe Pro Glu Met Met Asn Arg Tyr Lys Gln Leu Leu Thr Tyr Ile
                85                  90                  95

CGG AGT GCA GTC ACA AGA AAT TAT TCT GAA AAA TCC ATT AAT TCT ATT       336
Arg Ser Ala Val Thr Arg Asn Tyr Ser Glu Lys Ser Ile Asn Ser Ile
            100                 105                 110

CTT GAT TAT ATC TCT ACT TCT AAA CAG ATG GAT TTA CTG CAG GAA TTC       384
Leu Asp Tyr Ile Ser Thr Ser Lys Gln Met Asp Leu Leu Gln Glu Phe
        115                 120                 125

TAT GAA ACA ACA CTG GAA GCT TTG AAA GAT GCT AAG AAT GAT AGA CTG       432
Tyr Glu Thr Thr Leu Glu Ala Leu Lys Asp Ala Lys Asn Asp Arg Leu
    130                 135                 140

TGG TTT AAG ACA AAC ACA AAG CTT GGA AAA TTA TAT TTA GAA CGA GAG       480
Trp Phe Lys Thr Asn Thr Lys Leu Gly Lys Leu Tyr Leu Glu Arg Glu
145                 150                 155                 160

GAA TAT GGA AAG CTT CAA AAA ATT TTA CGC CAG TTA CAT CAG TCG TGC       528
Glu Tyr Gly Lys Leu Gln Lys Ile Leu Arg Gln Leu His Gln Ser Cys
                165                 170                 175

CAG ACT GAT GAT GGA GAA GAT GAT CTG AAA AAA GGT ACA CAG TTA TTA       576
Gln Thr Asp Asp Gly Glu Asp Asp Leu Lys Lys Gly Thr Gln Leu Leu
            180                 185                 190

GAA ATA TAT GCT TTG GAA ATT CAA ATG TAC ACA GCA CAG AAA AAT AAC       624
Glu Ile Tyr Ala Leu Glu Ile Gln Met Tyr Thr Ala Gln Lys Asn Asn
        195                 200                 205

AAA AAA CTT AAA GCA CTC TAT GAA CAG TCA CTT CAC ATC AAG TCT GCC       672
Lys Lys Leu Lys Ala Leu Tyr Glu Gln Ser Leu His Ile Lys Ser Ala
    210                 215                 220

ATC CCT CAT CCA CTG ATT ATG GGA GTT ATC AGA GAA TGT GGT GGT AAA       720
Ile Pro His Pro Leu Ile Met Gly Val Ile Arg Glu Cys Gly Gly Lys
```

```
ATT GCA CTT GGG GGA GGT GAA TTT GAA AAG GCA CAC ACT GAT TTT TTT        768
Ile Ala Leu Gly Gly Gly Glu Phe Glu Lys Ala His Thr Asp Phe Phe
                    245                 250                 255
```

(2) INFORMATION FOR SEQ ID NO: 28:

(i) SEQUENCE CHARACTERISTICS:
        (A) LENGTH: 1121
        (B) TYPE: nucleic acid
        (C) STRANDEDNESS: double
        (D) TOPOLOGY: linear (xi) SEQUENCE DESCRIPTION: SEQ ID NO: 28:

```
GCA GAG GTT AAA ACA CCT TTT GAT TTG GCC AAG GCA CAA GAG AAC AGC         48
Ala Glu Val Lys Thr Pro Phe Asp Leu Ala Lys Ala Gln Glu Asn Ser
1                   5                   10                  15

AAC TCC GTA AAG AAG AAG ACA AAG TTT GTC AAT TTA TAC ACA AGA GAA         96
Asn Ser Val Lys Lys Lys Thr Lys Phe Val Asn Leu Tyr Thr Arg Glu
                20                  25                  30

AGA CAG GAC AGG CTT GCA GTC CTG CTC CCT GGT CGT CAC CCT TGT GAT        144
Arg Gln Asp Arg Leu Ala Val Leu Leu Pro Gly Arg His Pro Cys Asp
            35                  40                  45

TGC CTG GGC CAG AAG CAC AAG CTC ATC AAT AAC TGT CTG ATC TGT GGG        192
Cys Leu Gly Gln Lys His Lys Leu Ile Asn Asn Cys Leu Ile Cys Gly
        50                  55                  60

CGC ATT GTC TGT GAA CAA GAA GGC TCA GGC CCT TGC TTA TTC TGT GGC        240
Arg Ile Val Cys Glu Gln Glu Gly Ser Gly Pro Cys Leu Phe Cys Gly
65                  70                  75                  80

ACT CTG GTG TGT ACT CAT GAG GAA CAA GAT ATT TTA CAG CGT GAC TCA        288
Thr Leu Val Cys Thr His Glu Glu Gln Asp Ile Leu Gln Arg Asp Ser
                85                  90                  95

AAC AAG AGC CAG AAA CTG CTA AAG AAA CTC ATG TCA GGA GTG GAG AAT        336
Asn Lys Ser Gln Lys Leu Leu Lys Lys Leu Met Ser Gly Val Glu Asn
            100                 105                 110

TCT GGA AAG GTG GAC ATC TCT ACC AAG GAC CTT CTT CCT CAT CAA GAA        384
Ser Gly Lys Val Asp Ile Ser Thr Lys Asp Leu Leu Pro His Gln Glu
        115                 120                 125

TTG CGA ATT AAG TCT GGT CTG GAG AAG GCT ATC AAG CAT AAA GAC AAA        432
Leu Arg Ile Lys Ser Gly Leu Glu Lys Ala Ile Lys His Lys Asp Lys
    130                 135                 140

CTG TTA GAG TTT GAC AGA ACT AGT ATT CGA AGG ACC CAA GTC ATT GAT        480
Leu Leu Glu Phe Asp Arg Thr Ser Ile Arg Arg Thr Gln Val Ile Asp
145                 150                 155                 160

GAT GAG TCA GAT TAC TTT GCC AGT GAT TCT AAC CAA TGG TTG TCC AAA        528
Asp Glu Ser Asp Tyr Phe Ala Ser Asp Ser Asn Gln Trp Leu Ser Lys
                165                 170                 175

CTT GAG CGG GAA ACC TTG CAG AAG CGA GAG GAG GAG CTG AGA GAA CTT        576
Leu Glu Arg Glu Thr Leu Gln Lys Arg Glu Glu Glu Leu Arg Glu Leu
            180                 185                 190

CGA CAC GCC TCT CGA CTT TCT AAG AAG GTC ACC ATT GAC TTT GCA GGA        624
Arg His Ala Ser Arg Leu Ser Lys Lys Val Thr Ile Asp Phe Ala Gly
        195                 200                 205

AGG AAG ATC CTG GAA GAA GAA AAT TCA CTA GCA GAG TAT CAT AGC AGA        672
Arg Lys Ile Leu Glu Glu Glu Asn Ser Leu Ala Glu Tyr His Ser Arg
    210                 215                 220

CTA GAT GAG ACA ATA CAG GCC ATT GCC AAT GGA ACC TTG AAC CAG CCA        720
Leu Asp Glu Thr Ile Gln Ala Ile Ala Asn Gly Thr Leu Asn Gln Pro
225                 230                 235                 240

CTG ACC AAA TTG GAT AGA TCT TCT GAA GAG CCT TTG GGA GTT CTG GTA        768
Leu Thr Lys Leu Asp Arg Ser Ser Glu Glu Pro Leu Gly Val Leu Val
                245                 250                 255
```

```
AAT CCC AAC ATG TAC CAG TCC CCT CCC CAG TGG TTG ACC ACA CAG GTG         816
Asn Pro Asn Met Tyr Gln Ser Pro Pro Gln Trp Leu Thr Thr Gln Val
            260                 265                 270

CAG CCT CAC AGA AGA AGG CTT TCC GTT CTT CAG GAT TTG GAC TAG AGT         864
Gln Pro His Arg Arg Arg Leu Ser Val Leu Gln Asp Leu Asp     Ser
        275                 280                 285

TCA ACT CAT TTC AGC ACC AGT TGC GAA TCC AGG ATC AAG AAT TTC AGG         912
Ser Thr His Phe Ser Thr Ser Cys Glu Ser Arg Ile Lys Asn Phe Arg
        290                 295                 300

AAG GCT TTG ATG GTG GCT GGT GCC TCT CTG TAC ATC AGC CCT GGG TTC         960
Lys Ala Leu Met Val Ala Gly Ala Ser Leu Tyr Ile Ser Pro Gly Phe
305                 310                 315                 320

TCT GCT TGT CAG AGG GAT TAA AAG GGT GGA GGG CAG ATC CTG GTA CAC        1008
Ser Ala Cys Gln Arg Asp     Lys Gly Gly Gly Gln Ile Leu Val His
            325                 330                 335

CCC CCA CAG AGG ACG ACT TTG GAT AGC AGC CAC AGC TAA AAA ATC CCT        1056
Pro Pro Gln Arg Thr Thr Leu Asp Ser Ser His Ser     Lys Ile Pro
            340                 345                 350

CCC CTC AAG AAG TCT CAG AAC TCC AGG CTA CAT ATC GTC TTC TTC GTT        1104
Pro Leu Lys Lys Ser Gln Asn Ser Arg Leu His Ile Val Phe Phe Val
            355                 360                 365

GGG AAG ATG TGG AAT TT                                                 1121
Gly Lys Met Trp Asn
    370

(2) INFORMATION FOR SEQ ID NO:    29:

(i) SEQUENCE CHARACTERISTICS:
        (A) LENGTH:         108
        (B) TYPE:           nucleic acid
        (C) STRANDEDNESS:   double
        (D) TOPOLOGY:       linear (xi) SEQUENCE DESCRIPTION: SEQ ID NO: 29:

GAA AGG GCC CTG ACA GCA CAC ACA CTT AAA CAC AGT TTT CTG ATA ACT          48
Glu Arg Ala Leu Thr Ala His Thr Leu Lys His Ser Phe Leu Ile Thr
1               5                   10                  15

TTG GAA TTC ACA CCG TTG GAC TAG TTA AAA ACT TCT AAA ATA ATT TTT         96
Leu Glu Phe Thr Pro Leu Asp     Leu Lys Thr Ser Lys Ile Ile Phe
            20                  25                  30

TAA AAT CTA ATA                                                        108
    Asn Leu Ile
        35

(2) INFORMATION FOR SEQ ID NO:    30:

(i) SEQUENCE CHARACTERISTICS:
        (A) LENGTH:         219
        (B) TYPE:           nucleic acid
        (C) STRANDEDNESS:   double
        (D) TOPOLOGY:       linear (xi) SEQUENCE DESCRIPTION: SEQ ID NO: 30:

CCA GGA ACT GAG ATC TTT AAT CTG CCA GCA GTT ACT ACG TCA GGC TCA          48
Pro Gly Thr Glu Ile Phe Asn Leu Pro Ala Val Thr Thr Ser Gly Ser
1               5                   10                  15

GTT AGC TCT AGA GGC CAT TCT TTT GCT GAT CCT GCC AGT AAT CTT GGG         96
Val Ser Ser Arg Gly His Ser Phe Ala Asp Pro Ala Ser Asn Leu Gly
            20                  25                  30

CTG GAA GAC ATT ATC AGG AAG GCT CTC ATG GGA AGC TTT GAT GAC AAA        144
Leu Glu Asp Ile Ile Arg Lys Ala Leu Met Gly Ser Phe Asp Asp Lys
            35                  40                  45

GTT GAG GAT CAT GGA GTT GTC ATG TCC CAG CCT ATG GGA GTA GTG CCT        192
Val Glu Asp His Gly Val Val Met Ser Gln Pro Met Gly Val Val Pro
```

-continued

```
Val Glu Asp His Gly Val Val Met Ser Gln Pro Met Gly Val Val Pro
 50              55                  60

GGT ACT GCC AAC ACC TCA GTT GTG ACC                                 219
Gly Thr Ala Asn Thr Ser Val Val Thr
 65              70
```

(2) INFORMATION FOR SEQ ID NO: 31:

(i) SEQUENCE CHARACTERISTICS:
        (A) LENGTH:           223
        (B) TYPE:             amino acid
        (C) STRANDEDNESS:
        (D) TOPOLOGY:         Not Relevant (xi) SEQUENCE DESCRIPTION: SEQ ID NO: 31:

```
Leu Gln Leu Glu Ala Glu Asn Tyr Glu Gly His Thr Pro Leu His Val
  1               5                  10                  15

Ala Val Ile His Lys Asp Val Glu Met Val Arg Leu Leu Arg Asp Ala
                 20                  25                  30

Gly Ala Asp Leu Asp Lys Pro Glu Pro Thr Cys Gly Arg Ser Pro Phe
                 35                  40                  45

Ile Trp Leu Asp Leu Glu Ala Arg Asn Tyr Asp Gly Leu Thr Ala Leu
 50                  55                  60

His Val Ala Val Asn Thr Glu Cys Gln Glu Thr Val Gln Leu Leu Leu
 65                  70                  75                  80

Glu Arg Gly Ala Asp Ile Asp Val Asp Ile Lys Ser Gly Arg Ser Pro
                 85                  90                  95

Leu Ile His Gln Trp Arg Pro Gly Ser Arg Cys Ala Gly Ala Ser Leu
                100                 105                 110

Arg Ala Gly Ala Asn Pro Ala Ala Arg Met Tyr Gly Gly Arg Thr Pro
                115                 120                 125

Leu Gly Ser Ala Met Leu Arg Pro Asn Pro Ile Leu Ala Arg Leu Leu
                130                 135                 140

Arg Ala Val Glu Asn Asn Ser Leu Ser Met Val Gln Leu Leu Leu Gln
145                 150                 155                 160

His Gly Ala Asn Val Asn Ala Gln Met Ser Gly Ser Ser Ala Leu His
                165                 170                 175

Ser Ala Ser Gly Arg Gly Leu Leu Pro Leu Val Arg Thr Leu Val Ala
                180                 185                 190

His Gly Ala Pro Glu Pro Glu Gly Lys Asp Glu Lys Ser Gly Pro Arg
                195                 200                 205

Ser Gly Ala Asp Ser Ser Leu Lys Asn Cys His Asn Asp Thr Pro
                210                 215                 220
```

What is claimed is:

1. Purified DNA comprising a sequence encoding a protein having the amino acid sequence of JL1 shown in FIG. 2 (SEQ ID NO: 1) or an amino acid sequence that is at least 80% identical to SEQ ID NO: 1, and which protein specifically and physically interacts with a thyroid hormone receptor in an in vivo interaction trap assay.

2. The DNA of claim 1 comprising a sequence encoding the amino acid sequence of JL1 shown in FIG. 2 (SEQ ID NO: 1).

3. The purified DNA of claim 1 or 2, wherein said DNA is cDNA.

4. The purified DNA of claim 1, wherein said DNA encodes a human protein.

5. A vector comprising the purified DNA of claim 1.

6. A cell containing the purified DNA of claim 1.

7. A method of producing a recombinant protein which specifically and physically interacts with a thyroid hormone receptor in an in vivo interaction trap assay comprising, providing a cell transformed with the DNA of claim 1 positioned for expression in said cell;

culturing said transformed cell under conditions for expressing said DNA; and isolating said recombinant protein.

* * * * *

UNITED STATES PATENT AND TRADEMARK OFFICE
CERTIFICATE OF CORRECTION

PATENT NO. : 5,962,256
DATED : October 5, 1999
INVENTOR(S) : David D. Moore et al.

It is certified that error appears in the above-identified patent and that said Letters Patent is hereby corrected as shown below:

Column 6,
Line 19, replace "FIG. 3 shows" with -- FIG. 3A shows --;

Column 10,
Line 2, replace "hormone-" with -- hormone⁻ --.

Signed and Sealed this

Twenty-first Day of May, 2002

Attest:

Attesting Officer

JAMES E. ROGAN
Director of the United States Patent and Trademark Office